(12) United States Patent
Elzufon et al.

(10) Patent No.: US 12,274,727 B2
(45) Date of Patent: Apr. 15, 2025

(54) CANNABIGEROL (CBG) PRODUCTS AND METHODS OF USE

(71) Applicant: Bazelet Health Systems, Inc., Orlando, FL (US)

(72) Inventors: Michael Elzufon, Maple Grove, MN (US); Howard Hoffberg, Reisterstown, MD (US)

(73) Assignee: Bzelet Health Systems, Inc., Orlando, FL (US)

( * ) Notice: Subject to any disclaimer, the term of this patent is extended or adjusted under 35 U.S.C. 154(b) by 0 days.

(21) Appl. No.: 18/433,252

(22) Filed: Feb. 5, 2024

(65) Prior Publication Data

US 2024/0180987 A1 Jun. 6, 2024

Related U.S. Application Data

(62) Division of application No. 17/990,637, filed on Nov. 18, 2022, now Pat. No. 11,890,311.

(60) Provisional application No. 63/280,865, filed on Nov. 18, 2021.

(51) Int. Cl.

| | |
|---|---|
| *A61K 36/185* | (2006.01) |
| *A61K 31/00* | (2006.01) |
| *A61K 31/05* | (2006.01) |
| *A61K 31/12* | (2006.01) |
| *A61K 31/16* | (2006.01) |
| *A61K 31/164* | (2006.01) |
| *A61K 31/165* | (2006.01) |
| *A61K 31/19* | (2006.01) |
| *A61K 31/4525* | (2006.01) |
| *A61K 31/5685* | (2006.01) |
| *A61K 36/068* | (2006.01) |
| *A61K 36/28* | (2006.01) |
| *A61K 36/9066* | (2006.01) |

(52) U.S. Cl.
CPC ............ *A61K 36/185* (2013.01); *A61K 31/05* (2013.01); *A61K 31/12* (2013.01); *A61K 31/16* (2013.01); *A61K 31/164* (2013.01); *A61K 31/165* (2013.01); *A61K 31/19* (2013.01); *A61K 31/4525* (2013.01); *A61K 31/5685* (2013.01); *A61K 31/658* (2023.05); *A61K 36/068* (2013.01); *A61K 36/28* (2013.01); *A61K 36/9066* (2013.01)

(58) Field of Classification Search
None
See application file for complete search history.

(56) References Cited

FOREIGN PATENT DOCUMENTS

WO    WO 2009001081    * 12/2008

OTHER PUBLICATIONS

Leafly, 6 pages, 2020.*

* cited by examiner

*Primary Examiner* — Michael V Meller
(74) *Attorney, Agent, or Firm* — Hoffberg & Associates; Steven M. Hoffberg

(57) ABSTRACT

A cannabinoid composition having antiinflammatory and antineoplastic activity, comprising a full spectrum extract of a plant of genus *Cannabis* comprising at least 5% by weight cannabigerol, comprising *Cannabis* terpenes and *Cannabis* flavonoids, and substantially without cannabidiol and tetrahydrocannabinol. The composition may be a pharmaceutically acceptable formulation for oral, sublingual, inhaled, vaporized, or smoked administration. The formulation may include absorption or pharmacological enhancers e.g., curcumin, resveratrol, quercitin, piperine and/or N-alkylamides. The composition has anti-inflammatory properties beneficial as a prophylaxis or therapy of symptoms due to viral infection, and tumor growth.

18 Claims, 3 Drawing Sheets

CANNABIGEROL (CBG) PRODUCTS AND METHODS OF USE

CROSS REFERENCE TO RELATED APPLICATIONS

Figure 1:
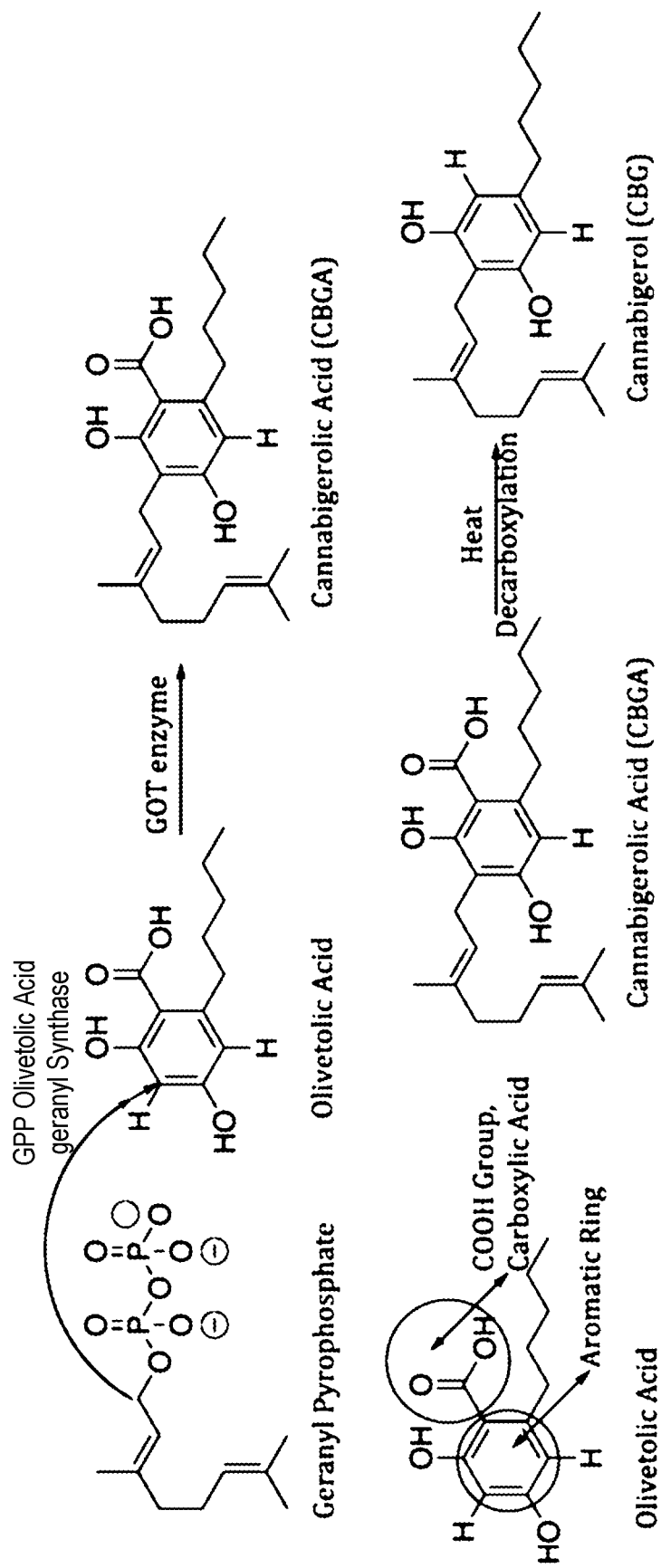

The present application is a Divisional of U.S. patent application Ser. No. 17/990,637, filed Nov. 18, 2022, now U.S. Pat. No. 11,890,311, issued Feb. 6, 2024, which is a Non-provisional of, and claims benefit of priority from, U.S. Provisional Patent Application No. 63/280,865, filed Nov. 18, 2021, the entirety of which are expressly incorporated by reference.

FIELD OF THE INVENTION

The present invention relates to the field of cannabinoids, and more particularly to cannabigerol (CBG), a cannabinoid, in new formulations and with new uses.

BACKGROUND OF THE INVENTION

Each reference and document cited herein is expressly incorporated herein by reference in its entirety, for all purposes.

Cannabis Species and Background

*Cannabis* refers to a genus of annual herbaceous plants in the Cannabaceae family. Humans have cultivated *Cannabis* throughout recorded history as a source of industrial fiber, seed oil, food, and medicine, and for religious, spiritual and recreational purposes.

The *Cannabis* genus of plants has been cultivated and used for its medicinal and industrial benefits dating back to ancient times. *Cannabis* comprises various strains termed *Cannabis sativa, Cannabis ruderalis*, and *Cannabis* indica. *Cannabis* has more than 550 different components, of which about 150 belong to $C_{21}$ or $C_{22}$ terpenophenolic phytochemicals, which are predominantly expressed in the *Cannabis* plant and thus, they are termed cannabinoids. The other 400 components are terpenes and phenolic compounds, known as flavonoids and terpenes. The most abundant cannabinoid, tetrahydrocannabinol (THC), is well known for its psychoactive properties. A psychoactive drug or psychotropic substance is a chemical substance that acts primarily upon the central nervous system where it alters brain function, resulting in temporary changes in perception, mood, consciousness and behavior, with additional properties of being potentially habit-forming, causing chemical dependency and/or withdrawal symptoms, and may lead to a substance use disorder. Cannabidiol (CBD) as the second-most abundant, and cannabigerol (CBG) as the third most abundant, are both essentially non-psychoactive.

Many different cultures have used the *Cannabis* plant to treat a plethora of ailments. Practitioners in ancient China targeted malaria, menstrual symptoms, gout, and constipation. During medieval times, *Cannabis* was used for pain, epilepsy, nausea, and vomiting, and in Western medicine it was commonly used as an analgesic. In the US, physicians prescribed *Cannabis sativa* for a multitude of illnesses until restrictions were put in place in the 1930s and then finally stopped using it in 1970 when the federal government listed marijuana as a DEA (drug enforcement agency) classified Schedule I substance, claiming it an illegal substance with no medical value. California was the first state to go against the federal ban and legalize medical marijuana in 1996. Now, most states have approved medical *Cannabis* for intrastate commerce, and some have even legalized recreational marijuana. The Farm Bill in 2018 defined hemp as cultivars of *Cannabis* that contain less than 0.3% THC, by dry weight, and allowed the widespread cultivation of hemp (*sativa*) plants in the US, and its derivatives, which can be legally extracted as supplements. Δ8-THC (some states have classified this as a DEA Schedule I illicit substance) can be synthesized from CBD, but cannot be synthesized from CBG. Pharmaceutical formulations of CBD have FDA approval for certain pediatric patients with seizures have been classified as DEA Schedule V drug.

*Cannabis sativa* and variants thereof, including *Cannabis* chemovars (varieties characterized by virtue of their chemical composition as the result of genetic crosses, self-crosses or hybrids thereof) naturally contain different amounts of the individual cannabinoids.

Different strains of other *Cannabis* plants contain varying amounts of THC (mainly found in indica) and CBD (found in both indica and *sativa*, except *Panakeia*), and much lower quantities of other phytocannibinoids including CBG.

*Cannabis sativa* L. is a prolific, but not exclusive, producer of a diverse group of isoprenylated resorcinyl polyketides collectively known as cannabinoids (Hanuš et al. 2016).

Phytocannabinoid Synthesis

Cannabinoids and terpenoids are produced and stored in the secretory cells of glandular trichomes, which are found in the aerial parts of *Cannabis* plants and are especially dense on the top surfaces of seedless female flowers. CBGA is primarily found in the plant's trichomes (fine outgrowths or "hair" on plants). Cannabinoid production in *Cannabis* plants begins when an enzyme causes geranyl pyrophosphate and olivetolic acid to condense to form cannabigerolic acid (CBGA), a ringed structure. Both CBGA (which has been found in animal studies to be more effective for seizures triggered by a febrile event than CBD, and the acidic form CBGA has greater neuron permeability), and Cannabigerovarinic acid (CBGVA) are considered to be "stem cell" cannabinoids from either species, as they are the carboxylic acid precursors of all other cannabinoids. In regular *sativa* L hemp plants, CBG usually constitutes no more than 10% of the entire cannabinoid profile, with predominant CBD content, while in some CBG-dominant strains, this value can go up to 94% (the remainder has other cannabinoids including CBD), especially if grown at high altitudes.

Figure 2:
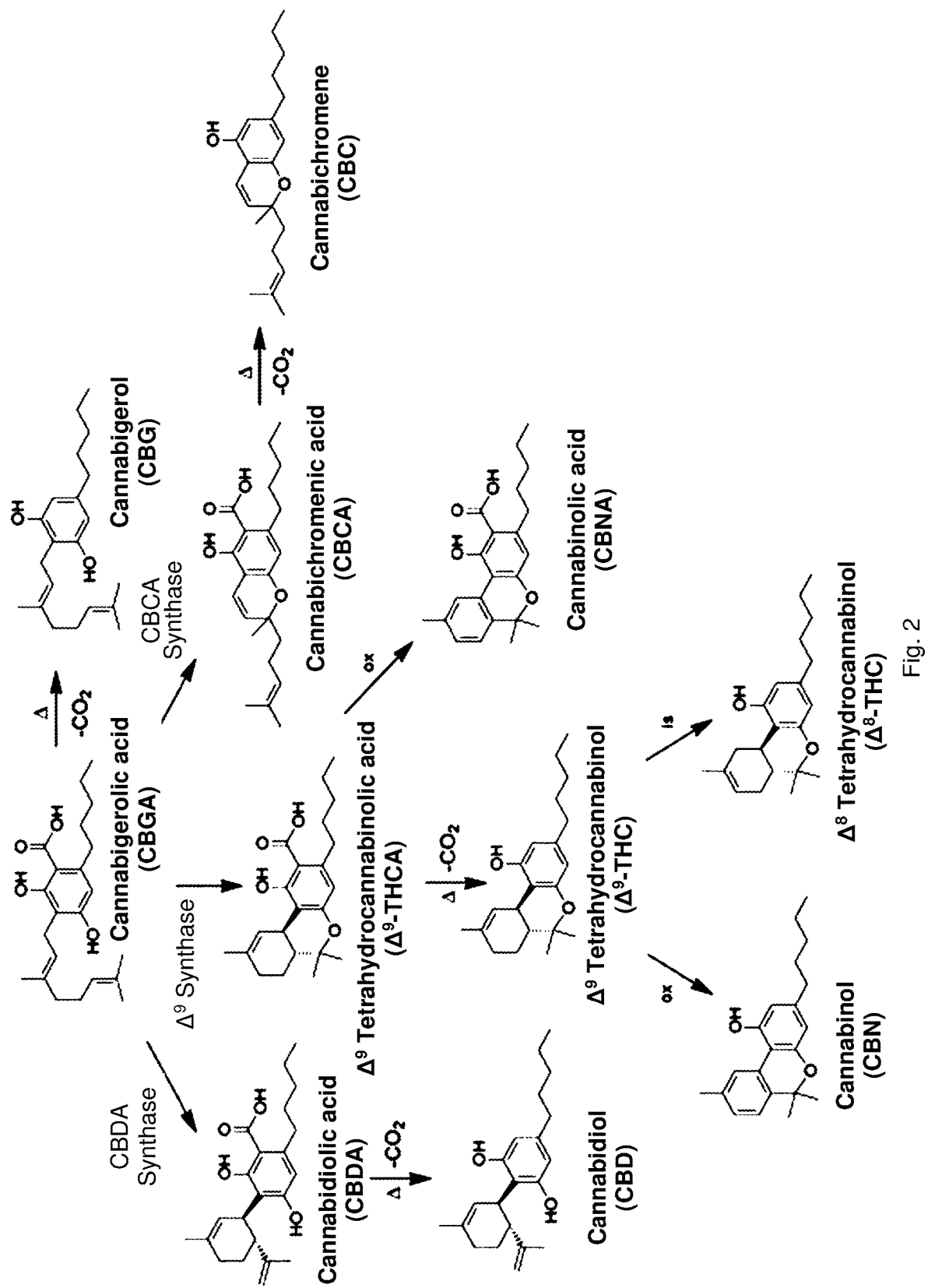
Figure 3:
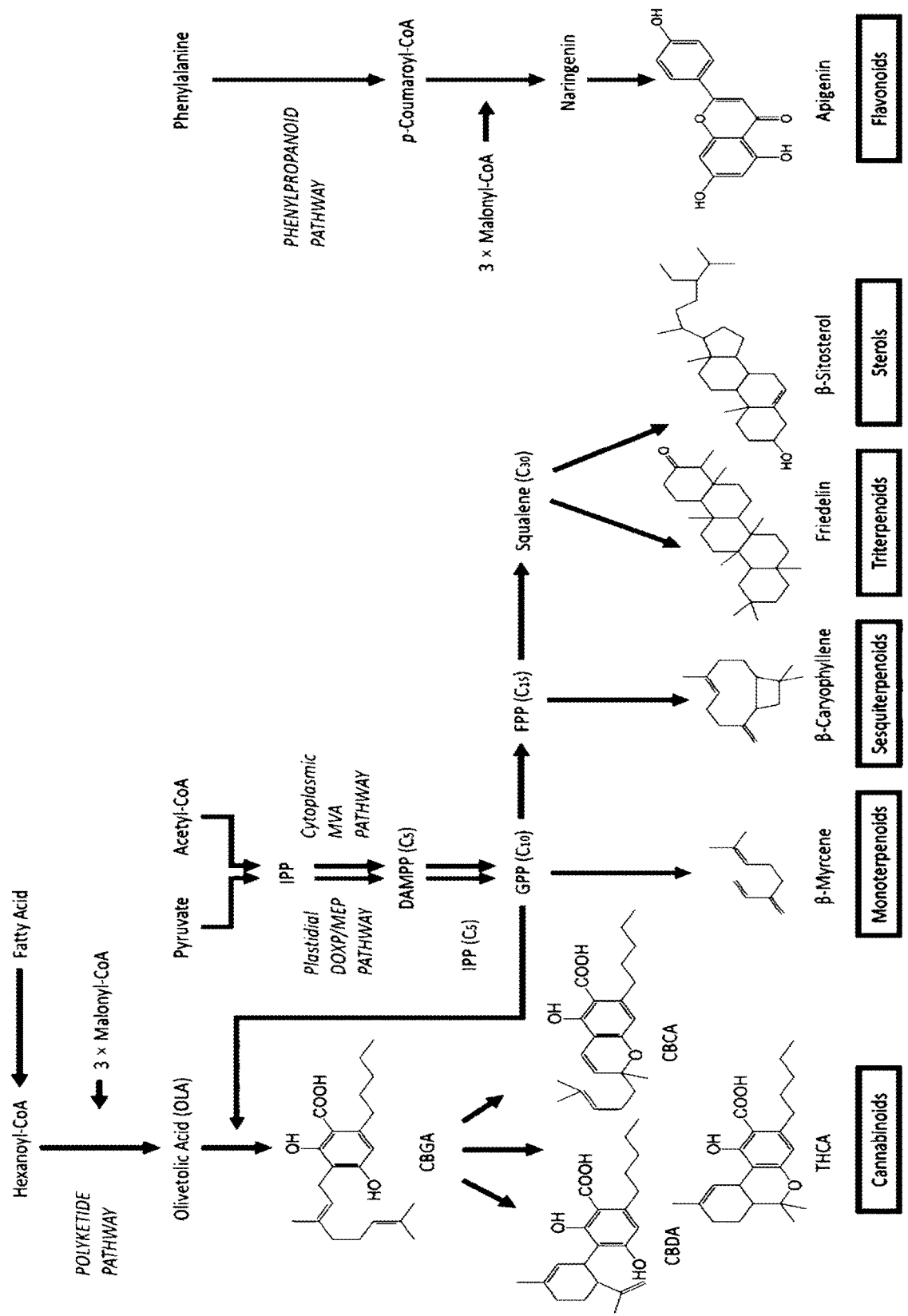

Currently, there is a novel, proprietary unique strain of Hemp, called *Panakeia*, (US PP32,725 P2, Jan. 5, 2021) or *Cannabis sativa* L., that produces CBGA (also with CBGVA), which has been genetically modified at chromosome 6, to be have structural mutations of tetrahydrocannabinolic synthase or cannabidiolic acid synthase that effectively prevent the CBGA from forming either tetrahydrocannabinolic acid (THCA) and cannabidiolic acid (CBDA), respectively, but still has intact cannabigerolic acid synthase to form CBG. See FIG. 2.

Therefore, in the Panekeia™ strain, CBGA (or CBVGA) can ONLY convert into CBG (or CBGV, respectively), and uniquely contains CBGA (5-19%), 0.00% THC (includes no Δ-8, Δ-9, Δ-10, or Δ-0 isomers), and 0.0% CBD. Panekeia™ plants have cultivation parameters (climate, light exposure, soil milieu/fertilizer content, time of harvest), which can be optimized for higher yields of flower (or seeds for regermination), and the growing conditions can result in variable ranges of CBGA, as well as different distribution of terpenes and flavonoids constituents. The chemical composition of *Cannabis* is largely determined by plant genetics, but is also affected by cultivation, harvesting, drying, and other manufacturing factors. Accordingly, the substance profile of any one product will likely differ qualitatively and quantitatively from the next.

CBGA also produces other major cannabinoid lines with all other *Cannabis* species:

THCA (not generally found in *Panakeia*), is mostly found in indica plants, and in a much lower concentration in *sativa*; CBDA (not generally found in *Panakeia*), and CBCA (cannabichromenic acid) are found in *sativa* plants, and to a lesser extent in indica. These unstable molecules are converted to active product via enzymatic processes through decarboxylation through cannabinoid synthase enzymes or by heating, and rapidly converted to THC (not generally found in *Panakeia*), CBD (not generally found in *Panakeia*), or CBC respectively. There are a variety of other THC analogues, iso-tetrahydrocannabinol-type (isomers of THC, not generally found in *Panakeia*™), and Cannabitriol (CBT), which is an oxidation product of THC (not generally found in *Panakeia*), which may act as an antiestrogen and aromatase inhibitor. WO/2020/249184, expressly incorporated herein by reference discloses synthesis and purification of cannabigerol.

CBD Pharmacologic Effects

CBD (non-psychoactive product and not generally found in *Panakeia*), along with its homologue, cannabidiphorol (CBDP and not generally found in *Panakeia*) is an allosteric modulator, which attaches to the cell's ligand, wherein, it indirectly effects endocannabinoid system (EDS), as well as direct binding to cannabinoid (CB)2 receptors. Cannabidiol dimethyl ether (CBDD and not generally found in *Panakeia*) is a trace component from CBD; it may also be made synthetically. It is a potent and selective inhibitor of the enzyme 15-lipoxygenase and inhibits oxygenation of linoleic acid, a process involved in the development of atherosclerosis; Cannabimovone (CBM, which is thought to be a rearrangement product of CBD, and may not be present in *Panakeia*) lacks affinity for cannabinoid receptors, but acts as an agonist at both Transient receptor potential vanilloid subtype 1 (TRPV1) and Peroxisome proliferators-activated receptor γ (PPARγ); CBD is an antagonist of G protein-coupled receptor 55 (GPR55), another cannabinoid receptor, blocking its function and altering brain activity in a way that may protect against seizures. When administered in higher doses, though, the benefits of lower concentrations may be lost. Anti-anxiety effects, for instance, seem to be obstructed while higher concentrations of CBD work to block GPR55 receptors. CBD is capable of killing cancer cells by acting like apigenin; it triggers apoptosis and reverses the effects of drug resistance of cancer cells. CBD can be hepatically metabolized to cannabielsoin (CBE and not generally found in *Panakeia*) which in turn, exhibited catalepsy, hypothermia and pentobarbitone-induced sleep prolongation in mice.

Exposure to CBD is associated with a reduction in mammalian testis size, the number of germ and Sertoli cells in spermatogenesis, fertilization rates, and plasma concentrations of hypothalamic, pituitary and gonadal hormones. Moreover, chronic doses of CBD have impaired sexual behavior in mice.

CBD has known metabolism through the genotypic hepatic cytochrome (CYP) P450 system mainly CYP3A4 and CYP2C19 (with lesser metabolism through CYP 2C8, CYP 2C9, CYP 1A2, CYP 2B6), which can result in a multitude of drug interactions (sometimes unpredictable), with greater CYP metabolism than THC.

Medical *Cannabis* (MC, including THC and CBD products) should not be used in combination with CNS depressant drugs including barbiturates, benzodiazepines, lithium, opioids, buspirone, antihistamines, muscle relaxants and other sedating medications or illicit substances/cocaine, as well as alcohol because MC can potentiate the sedative, psychomotor, respiratory, and other dangerous effects, resulting in reduced alertness, including impaired driving or operating machinery.

Potential drug interactions mediated by Cytochrome P450 drug interactions (2C9, 3A4); dose adjustments may be necessary:

MC may reduce the effects of the following medications: aminophylline, caffeine, clozapine, duloxetine, estradiol, estrogens, flutamide, fluvoxamine, frovatriptan, lidocaine, melatonin, mexiletine, mirtazapine, olanzapine, propranolol, ramelteon, rasagiline, ropinirole, theophylline, tizanidine, triamterene, zolmitriptan. MC may increase the effects of the following medications: amphotericin B, antipyrine, barbiturates, cyclosporine, warfarin. The following drugs may reduce the effects of MC: barbiturates, carbamazepine, clobazam, enzalutamide, fosphenytoin, phenobarbital, phenytoin, primidone, rifabutin, rifampin, rifapentine, St. John's wort. The effects of MC may be increased by amiodarone, chloramphenicol, cimetidine, clarithromycin, clopidogrel, darunavir, delavirdine, desmethylclobazam, disulfiram, efavirenz, eslicarbazepine, esomeprazole, felbamate, fluconazole, fluorouracil, fluoxetine, fluvoxamine, gemfibrozil, grapefruit juice, isoniazid, itraconazole, ketoconazole, lopinavir, metronidazole, modafinil, mifepristone, naltrexone, nefazodone, nelfinavir, ombitasvir, omeprazole, oxcarbazepine, paritaprevir, phenytoin, posaconazole, ritonavir, rufinamide, saquinavir, sulfadiazine, sulfamethoxazole, ticlopidine, telaprevir, telithromycin, tolbutamide, topiramate, verapamil, valproic acid, voriconazole, warfarin, and zonisamide.

When simultaneously using anticholinergics, antihistamines, cocaine, tricyclic antidepressants (also amoxapine), or sympathomimetic agents, it can further enhance tachycardic and hypertensive effects of MC.

Patients are advised to avoid taking metronidazole and disulfiram for 14 days before or 7 days after starting MC (may cause abdominal cramps, nausea, vomiting, headaches and flushing) Reference: www.me0dscape.com/viewarticle/881059?src=wnl_edit_tpal&uac=23154PN.

CBD has potential cytochrome P450 drug interactions CYP3A4 and CYP2C19 (with lesser metabolism through CYP 2C8, CYP 2C9, CYP 1A2, CYP 2B6 CYP2D6 and to a lesser extent, CYP3 family). CBD (based on pharmaceutical grade cannabidiol FDA approved for treatment of certain childhood seizure disorders) may cause fatigue, nausea, vomiting, decreased or increased appetite, somnolence or wakefulness, diarrhea or upper respiratory infection.

CBD may increase levels of clobazam, eslicarbazepine, rufinamide, topiramate, zonisamide. CBD may further increase liver enzyme elevations with valproate www.medpagetoday.com/Neurology/Seizures/67107?xid=nl_mpt_Weekly_Education_2017-08-16&eun=g5118765dlr.

All anticonvulsants (including prescription CBD drugs) have a warning about potential suicidal ideation as mandated by the FDA.

CBD is a promoter of DDI (drug-drug interactions) and potentiates the action of many drugs. CBD has known metabolism through the genotypic microsomal hepatic cytochrome (CYP) P450 system mainly CYP3A4 and CYP2C19 (with lesser metabolism through CYP 2C8, CYP 2C9, CYP 1A2, CYP 2B6), which can result in a multitude of drug interactions (sometimes unpredictable), with greater CYP metabolism and DDI than THC; The metabolism of CBD to OH-CBD, an active metabolite, occurs through CYP2D6, and CBD acts as an inhibitor of THC, which is metabolized itself by CYP1A2, CYP2C9, or CYP3A. Furthermore, CBD, following oxidative reactions at phase 1 metabolism (CYP system), is then subject to phase II glucuronidation reactions by the enzymes UGT1A9 UGT2B7 and UGT1A7. Competitive binding for these enzymes between drugs also presents another point at which drug metabolite levels could be altered metabolism through this pathway.

CBG Metabolism

The cannabigerol-type cannabinoid group contains seven related molecules including CBG itself. As well as CBG and CBGA, the CBG group contains cannabigerovarin (CBGV), cannabinerolic acid A (CBNA), cannabigerovarinic acid A (CBNVA), and the monomethyl esters of CBG and CBGA, CBGM and CBGAM respectively.

In 2021, the United States Patent and Trademark Office has granted the Nextleaf Solutions LTD, a patent pertaining to a novel process for acetylating (an organic esterification reaction) Cannabigerol ("CBG"), and subsequent refinement of CBG-O-Acetate as a pro-drug, which can be activated by hepatic metabolism.

CBGA may be considered as a "pro-drug" for CBG, but it also possesses pharmacologic activity. In some of the commercially available product literature, there is often no distinction made between CBG and its parent CBGA (usually, for those products the CBGA is converted to CBDA/THCA because the hemp plant has the intact active enzyme)

In animals, 12 metabolites were identified. The major metabolites were monohydroxy compounds or epoxidation.

CBG metabolism appeared to be similar to the metabolism of CBC. Hydroxylation reactions are catalyzed by microsomal fractions, but particular CYPs responsible for the reactions were not identified.

CYP2J2, the primary CYP of cardiomyocytes but also found in the liver, is responsible for the metabolism of the endocannabinoid, anandamide (AEA) and for CBG.

This pathway is less significant with many other drug or supplements metabolic pathways, so there would be predictable less drug-drug interactions.

CBG and *Panakeia* extracts would predictably have minimal drug interactions due to its limited CYP metabolism, although there is considerable overlap for its therapeutic benefits.

Pharmacology of Other Cannabinoids

Cannabichromene (CBC) is a non-psychoactive product, and may be useful for treating anxiety and stress, inflammation, pain relief; it has both anti-viral and anti-tumor activity, and stimulates the growth of bone tissue, which can covert to cannabicyclol (CBL) on exposure to light, which are found in larger proportions with hemp (*sativa*) strains, and it may be a small component of *Panakeia*. It is reported to have a similar metabolic pathway as CBG.

As described, CBGA also converts to CBG (a stable, phenolic, lipid soluble, cannabinoid, non-psychoactive product found in the *sativa* plant, but more exclusively found in *Panakeia* in high proportions), as an acidic form which is predominantly found in hemp strains. When the side chain is a pentyl (5-carbon) chain the compound produced will be CBG. However, if the pentyl chain is replaced with a propyl (3-carbon) chain the CBG-type varin compound formed is CBGV (cannabigeroldivarin). The propyl variant will be formed if a 10-carbon precursor is reacted at the first stage of the biosynthetic pathway rather than a 12-carbon compound. CBGVA, in turn, converts to tetrahydrocannabivarin (THCV, found mainly in indica or special strains of *sativa* and not generally found in *Panakeia* due to lack of decarboxylation enzyme, synthase), Cannabidivarin (CBDV and not generally found in *Panakeia* due to lack of decarboxylation enzyme, cannabidiol synthase). THCV and CBDV have neutral antagonist activity at cannabinoid receptor 1 (CB1), which is a primarily binding site receptor for THC, which can be used as anorexic agent in rats. Cannabichromevarin (CBCV) are considered homologous, varin cannabinoids (with smaller carbon side chains) and may be contained in *Panakeia*; Similarly, cannabigerovarin (CBGV) from CBGVA, has been researched for both its anti-inflammatory and anti-cancer effects and is minor component of most strains of *Cannabis sativa*, is also contained in the *Panakeia* biomass extract; it contributes to the entourage effect. Although these later two varins are chemically distinct from their associated cannabinoids, they probably have similar biologic effects as their conventional cannabinoid counterparts.

Other minor cannabinoid contents which may be found in *Panakeia*™: cannabicyclol acid (CBLA), with anti-inflammatory and antineoplastic properties, heat stable, and resistant to decarboxylation may convert to very small quantities to CBL, which is also formed when CBC is exposed to light); Cannabinolic Acid (CBNA), an anti-inflammatory, and likely anti-biological; although it can theoretically convert to Cannabinol (CBN) by the hemp plant, but it is most likely, that detected CBN is actually as an oxidation product of THC, and cannabicitran (CBT), which is non-psychoactive, has been found to reduce intraocular pressure in tests on rabbits possibly due to agonist activity at the N-Arachidonyl glycine (NAGly) receptor, which is also known as G protein-coupled receptor 18 (GPR18).

Other cannabinoid products found in *Cannabis* species, but not *Panakeia*: In most indica plants, THCA eventually becomes THC (9-A, which is hepatically metabolized to 11-OH-THC, which is even more potent; along with other THC isomers), as a psychoactive product, as well as CBN, which is minimally psychoactive, as an oxidative degradation product of aged THC, or is produced when THC is exposed to ultraviolet light; it is supposed to be more sedating, but less potent than THC. CBN interacts with CB1 receptors to promote sedation and relaxation. It also directly interacts with CB2 receptors to encourage more optimal immune system function. CBN also seems to have some antioxidant and anti-inflammatory benefits, suggesting it could play a neuroprotective role. CBD can be used as a substrate to synthesize the mildly psychoactive 8-A THC, which also binds to CB1, and can be abused.

The conversion of THCA, CBDA, CBGA, and CBCA to THC, CBD, CBN, CBG, and CBG, respectively, through decarboxylation is usually necessarily before any biological effect can be observed. Decarboxylation may occur from enzymes, light or heating the plant above 105° C., which can be achieved, during the smoking or baking process.

Composition of Cannabinoids in *Cannabis*

In *Cannabis* indica, or marijuana, an average analysis of compounds reveals less than 1% of CBG (generally found primarily in immature plants) is present, compared to 20 to 25% of CBD, or 25 to 30% of THC, along with other minor phytocannabinoids, terpenes and flavonoids.

Hemp plants (*sativa*) are grown for their fibers (to make rope and textiles) have higher content of CBD that can be extracted to make oil from the biomass, or hemp seed oil; per federal law, industrial or cultivated hemp must contain less than 0.3% THC (dry weight) to be considered for interstate commerce; and it is from this *sativa* plant that CBD full spectrum oil is extracted (which is legal in most states; however, this threshold concentration of THC cannot be exceeded at any time during the entire extraction or distillation process). CBD is considered to have a wide scope of potential medical applications-due to clinical reports showing the lack of side effects (as is typically associated with A9-THC), and non-interference with several psychomotor learning and psychological functions. Proportions of CBD (isolated or full spectrum) may be added into the *Panakeia* extract for additional benefit and/or synergy as another variation of this proprietary patented product.

*Cannabis* including cannabinoids, terpenes/terpenoids, flavonoids, sterols and its secondary metabolite content have recently seen a surge in research interest. *Cannabis* terpenes and terpenoids, in particular, are increasingly the focus of research efforts due to the possibility of their contribution to the overall therapeutic effect of medicinal *Cannabis*. Current methodology to quantify terpenes in *Cannabis* biomass mostly relies on large quantities of biomass, long extraction protocols, and long gas or liquid chromatography (LC/GC) gradient times, often exceeding 60 min. They are therefore not easily applicable in the high-throughput environment of a *Cannabis* breeding program. The method presented here, however, is based on a simple hexane extract from 40 mg of biomass, with 50 µg/mL dodecane as internal standard, and a gradient of less than 30 min. The method can detect 48 individual terpenes and terpenoids and was validated for selectivity, linearity, lowest analyte concentration likely or lowest concentration at which the analyte can not only be reliably detected (LOD/LOQ), precision, intermediate precision, and accuracy (recovery) for 22 terpenes and terpenoids. The validation parameters are comparable to previously published studies that employ significantly longer runtimes and/or more complex extraction protocols. It is currently being applied to medicinal *Cannabis* precision breeding programs. For these products to be standardized and utilized in clinical trials, one could consider cultivating indoors ('greenhouse') with a controlled environment. Using data driven cultivation techniques (soil tests, sap tests, leaf temps etc.) to dial in a cultivar of interest, monitoring parameters such as varying photoperiods, Photosynthetic Photon Flux Density (PPFD). temperature, humidity, altitude, soil pH/salinity, pest and pathogens pressure, watering regimen, pruning, plant density, etc.

Panakeia™ Constituents

A sample analysis performed by Crest Lab 10/20/21 on recently harvested *Panakeia* reveals water content 11.7%, with CBGA 6.8%, CBG 0.1%, without detectable THCA, THC, THCV, CBDA, CBD, CBDV, CBC, CBN, heavy metals, pesticides, mycotoxins, below threshold aerobic bacteria, fungi and yeast, bile tolerant gram negative, *E coli*, *Salmonella*, Another sample analysis from Americanna Laboratories using a "dry" *Panakeia*™ 81000 mg flower reveals 5.4% moisture, with 6.52% total of available CBG (based detected CBGA=7.22% which converting by a factor of 0.877 to CBG, in addition to pure CBG=0.192%).

Other Phytochemicals in *Cannabis*

The *Cannabis* plant can contains >200 terpenes that have been identified. Three mono-terpenes, (myrcene, D-limonene and pinene), and sesquiterpenoid, (beta-caryophyllene), have been shown to have biological importance. However, there are roughly 30 terpenes (10 primary and 20 secondary) that are consistently found in high concentrations in most *Cannabis* varieties. The biologic effects of terpene in full-spectrum *Cannabis* extract is usually detectable above 0.05% v/w threshold including, β-myrcene (0.47% v/w), β-caryophyllene (0.05% v/w), -limonene (0.14% v/w) and α-pinene (0.049% v/w). Some of the terpenes, flavonoids and phytochemicals contained in *Panakeia* extract: Terpinolene, Linalool, Myrcene, Limonene, Beta Caryophyllene (Humulene), flavonoids, Apigenin (a phytoestrogen), and polyphenols, phytoestrogens, α-tocopherol (acetylated product may contribute to acute lung disease with inhalation products), and polyphenols.

The terpene/flavonoid content of any hemp plant can vary based on the growing milieu including geographics (altitude, temperature, humidity, light exposure, watering), and plant variety. The lots tend to be quite homogenous (e.g., if one lot is cultivated outdoors in certain conditions vs in greenhouse in a different lot).

Terpenes

Limonene strong lemony scent also found in citrus fruits, citrus scent responsible for Lemon Skunk. Limonene is thought to have anti-cancer and anti-depression abilities, to name a couple. Immune potentiator Antidepressant Antimutagenic fast acting mood-enhancing effects, reduced social anxiety, boost confidence, but with body relaxation, anti-inflammatory, dissolves gallstones, improves digestion, GERD and peristalsis, possible anti-breast cancer.

β-Myrcene is very abundant in nature; also found in hops, mangos, sweet basil, lemongrass, parsley bay leaves and wild thyme; This terpene has an earthy, musky, almost fruity tone. Its biggest benefit is that it can increase the effects of THC. It possesses Analgesic, Anti-inflammatory, Antibiotic (by enhancing transdermal absorption and is an effective antimicrobial agent), Antimutagenic and sedating/relaxing. β-myrcene demonstrates antinociceptive activity (i.e., induces insensitivity to pain) in rodents. The analgesic activity of β-myrcene acts at both central and peripheral sites and may involve the mediation of endogenous opioids. β-myrcene to inhibit certain forms of the cytochrome P-450 (2B subfamily) enzymes. In humans, dermatitis, conjunctivitis, and somnolence have all been reported following exposure to β-myrcene. In a single case report, chronic exposure to β-myrcene fumes caused severe and lingering asthma-like symptoms in hops inspector for a brewery. β-Myrcene, when administered orally to pregnant Wistar rats, induced a significant reduction in maternal weight gain, with additional effects for visceral malformations and delayed ossification. ntp.niehs.nih.gov/ntp/htdocs/chem_background/exsumpdf/beta-myrcene_508be.pdf β-myrcene is currently being studies as a possible human carcinogen and genotoxic effects especially after metabolic activation using human hepatic HepG2/C3A cells.

www.tandfonline.com/doi/abs/10.1080/15287394.2019.1577195.

The FDA took regulatory action in 2018 to no longer allow the use of the food additive, myrcene, a synthetic flavoring agent, based on results from National Toxicology Program carcinogenicity studies in rats (kidney cancer).

Mog, Steven R., and Yu Janet Zang. "Safety assessment of food additives: case example with myrcene, a synthetic flavoring agent." *Toxicologic pathology* 47, no. 8 (2019): 1035-1037.

Linalool relaxing scent, also found in lavender, The medical upsides of this floral terpene are its supposed sedative effects, helpful for aiding sleep, psychosis, epilepsy, and anxiety. Sedative Antidepressant Anxiolytic Immune potentiator antibacterial, antifungal, anti-anxiety, antidepressant, analgesic, flatulence relieving, as well as to have beneficial immunomodulatory effects on wound healing, anticancer with higher exposures, may cause eye and skin irritant with 7% of people found to be allergic undergoing patch testing in Europe were to the oxidized form of linalool, GRAS.

Pinene pine-like scent found in pine nuts, orange peels, rosemary, dill, and basil pine odor and acts as a bronchodilator (that is, it opens up airways). Anti-inflammatory Bronchodilator Stimulant Antibiotic Antineoplastic AChE inhibitor antianxiety, anti-inflammatory, analgesic, anesthetic-like effects, inhibits melanoma non-small cell lung carcinoma ovarian cancer neuroblastoma lymphoma and hepatocellular carcinoma, antioxidant benefits, anticoagulant properties, gastrointestinal benefits including pancreatitis, dental pain some guidance on inhalation hazards but not in concentrations you could expect to find in *Cannabis*, GRAS.

Alpha Caryophyllene (or Humulene, an isomer of β-caryophyllene) spicey taste, found in hops, sage, *Ginseng*, and cloves Also found in caraway cinnamon, oregano lavender rosemary basil and black pepper, this terpene has a spicy flavor and fights anxiety, inflammation, and tumors by acting on the body's CB2 pathways. Anti-inflammatory Cytoprotective (gastric mucosa) appetite suppressant Antimalarial anti-inflammatory analgesic, potentiates opioids, without causing psychoactive side effects, anti-aging protective role in a number of nervous system-related disorders including pain, anxiety, spasm, convulsions, depression, alcoholism, and Alzheimer's disease potential anticancer, may help gut and bowel disorders (such as IBS, colitis) to inhibit transient receptor potential melastatin 8 (TRPM8), an archetypical cold-activated ion channel of mammals, GRAS Caryophyllene oxide, in which the alkene group of caryophyllene has become an epoxide, is the component responsible for *Cannabis* identification by drug-sniffing dogs and is also an approved food flavoring. humulene's anti-inflammatory, anti-cancer, and anti-appetite forces amplify when combined with its cousin, beta-caryophyllene (β-caryophyllene), the "dietary cannabinoid" of terpenes.

Terpinene exotic, smells like turpentine, found in spices marjoram and cardamom, may increase anxiety, has antibacterial and antimicrobial properties that may make it an ideal addition to for topical application and as a treatment of acne or atopic dermatitis.

Guaiol sweet fruity flavor similar to plums pine-like aroma, found in cypress pines ginger, *Ginseng*, and valerian, is actually sesquiterpenoid alcohol instead of an oil, with anti-inflammatory and anti-bacterial properties, but may increase significant anxiety-causing effects (also seen with other minor terpenes in *Cannabis*—phellandrene, carene, and sabinene). There is also current controversy whether it also extolls anti-analgesic effects (avoid if you're taking CBD or *Cannabis* for pain relief). Guaiol is also a diuretic. It may lower high blood pressure, has anti-tussive effects, anticancer benefits for non-small cell lung cancer with anti-inflammatory effect, antioxidant, antiparasitic/microbial bacterial fungal effects, and insect repellent, it reduces inflammation in the lungs to treat coughing as well as in your limbs and other organs, making it above average at treating inflammatory conditions as diverse as arthritis, constipation, gout, sore throat, and even syphilis. It can strengthen the effects of chemotherapy and potentially reduce tumors and possibly stimulate menstruation and was even used as an abortifacient. Melting Point: 91.00 to 93.00° C. @ 760.00 mm Hg Boiling Point: 309.00 to 310.00° C. @ 760.00 mm Hg Vapor Pressure: 0.000054 mmHg @ 25.00° C. (est) Flash Point:236.00° F. TCC (113.33° C.) log P (o/w):4.782 (estimated) Shelf Life: 12 month(s) or longer if stored properly. Storage: refrigerate in tightly sealed containers. Soluble in: alcohol, water, 3.61 mg/L @ 25° C. (est.), Insoluble in: water.

Nerolidol sweet and flowery scent, tastes similar to citrus found in jasmine, ginger, lavender, and the tea-tree antioxidant effects "in counterbalancing the effect of radical free oxygen (ROS) by protecting the cells against oxidative damage to lipids, proteins, and DNA, significant anti-anxiety cross the skin barrier up to 1956% more efficiently, making it more effect if used in analgesic topical creams, anti-microbial and antifungal effects possible anti-cancer properties.

Bisabolol flowery scent with a mild and sweet taste found in chamomile anti-inflammatory and anti-microbial effects which make it a useful addition to creams eczema and psoriasis anti-irritant and skin healing benefits but may cause contact allergies.

Carene has fresh piney, with bitter after taste and fir needles, musky earth, and damp woodlands combination scent found in basil, anti-inflammatory, antifungal, and antibacterial treat acute skin inflammation may improve bone health used in cosmetics. natural antihistamine effect significant anxiety-causing effects.

Eucalyptol (makes up less than 0.06% of the complete terpene profile): minty smell that is also slightly spicy and cooling taste, found in sweet basil, bay leaves, wormwood, rosemary, and common sage, pain-relieving as an agonist of TRPM8 channels and anti-inflammatory properties increase in gastric mucus production which can be protective of the stomach and intestines respiratory effects significant anxiety-causing effects insecticidal properties antimicrobial antifungal toxic if ingested in larger quantities. It has the properties of: AChE inhibitor, Increases cerebral blood flow, Stimulant, Antibiotic, Antiviral, Anti-inflammatory, Antinociceptive.

Camphene (found in small quantities) musky earth damp woodland smell and can be found in ginger camphor oil and citronella oil antitumor melanoma and antioxidant properties lung inflammatory diseases where oxidative stress lower triglycerides and cholesterol with topical use may help inflammatory skin conditions such as psoriasis and eczema.

Borneol taste and smell are spicy and minty helps ovarian cancer help regain consciousness after TBI used as an adjunct to cross BBB digestive aid, help with heart function and aid in circulation, at higher concentrations, is an eye and skin irritant.

Terpineol sweet and slightly fruity flavor floral scent similar to lilacs strong sedative effect cytotoxic activity in the small cell lung carcinoma anti-inflammatory and pain-relieving effects, antifungal natural food preservative for fresh fruits.

Valencene Fruity smelling found in Valencia oranges used in cosmetics and perfumes antimicrobial insect repellant for ticks and mosquitoes.

Geraniol fruity taste, found in rose oil and citronella oil, antioxidant potential, exceptionally high bioavailability 92% after 30 min ingestion, Sedating, may help protect the brain from neurological disorders such as dementia or Alzheimer's "multi-target agent" against cancer scenting agent in bath products sweet-smelling insect repellent for mosquitos Bees use geraniol to mark the location of nectar-producing flowers.

Ocimene sweet, herbaceous, and woody aroma, found in a wide variety of fruits and herbs, including mint, parsley, pepper, basil, mangoes, orchids anti-inflammatory effects strong antifungal and antiviral properties.

γ-Eudesmol sweet and waxy tasting compound antiproliferative, antioxidant and antibacterial properties and can be found in a number of food items such as rosemary, *Ginkgo* nuts, mango, and common thyme).

α-Eudesmol antimicrobial activities found in orange mint and wild celery) both in the methanol family.

Guaienol expectorant, antiseptic, and local anesthetic. from woodsmoke, celery seeds, tobacco leaves, orange leaves, and lemon peels flavor of many substances such as whisky[5] and roasted coffee and can be synthesized to vanillin).

γ-Curcumene antifeedant and antifungal one of the major chemical constituents of turmeric found pepper (spice), lovage, wild carrot, and rosemary.

Pulegone (may also be obtained from the essential oils of a variety of plants such as *Nepeta cataria* (catnip), *Mentha piperita*, pennyroyal and spearmint) may be beneficial for IBS and other digestive conditions, as well as pain relief. Peppermint oil is generally safe, but it can be toxic when taken in very large doses. It is a carcinogen that causes hepatic carcinomas, pulmonary metaplasia, and other neoplasms on oral administration in rodents.

Trans-caryophyllene sharp smell that rises from cracked pepper found in oil of *Mentha longifolia* and *Commiphora gileadensis* antibacterial, anti-inflammatory, antimicrobial, Antileishmanial Compound and antioxidant properties Anxiety Relief Cholesterol Reduction Osteoporosis Prevention Seizure Management has anti-spasmodic activity on rat tracheal smooth muscle.

Flavonoids

Quercetin might be one of the more versatile flavonoids found in *Cannabis*, with studies indicating that it could have anticancer, anti-inflammatory, and antioxidant properties.

Beta-sitosterol includes foods such as rice bran, wheat germ, corn oils, soybeans, and peanuts and have a structure like the cholesterol and reduce the risk of some cancers, cholesterol metabolism lower cholesterol levels or anti-inflammatory It also is said to relieve symptoms of benign prostatic hyperplasia (BPH).

Other terpenes identified in CBD full spectrum extract: CBD (93.5% of phytocannabinoids, 61.7% of total product), CBG (6.1% of phytocannabinoids, 4.0% of total), THCV (0.4% phytocannabinoids, 0.3% of total); terpenes: Butylated hydroxytoluene (2.6% of terpenes, 0.3% total), antioxidant with potential anticancer properties, F.D.A.—which considers BHT to be "generally recognized as safe"-allow small amounts to be added to foods but the World Health Organization discussed a possible link between BHT and cancer risk and potential worsening of asthma and behavioral issues in children; Center for Science in the Public Interest puts BHT in its "caution" column and recommends avoiding it), 1,6-Dioxacyclododecane-7,12-dione (1%. 0.1%, may be harmful if swallowed, eye, skin and respiratory irritation and Specific target organ toxicity, single exposure), Guaiol (10.4%, 1.2%), γ-Eudesmol (2.3%, 0.3%) and α-Eudesmol (5.6%, 0.6%) (both in the methanol family), Guaienol (1.3%, 0.2%) γ-Curcumene (75.6%, 8.7%).

It would be anticipated that CBG full spectrum oil derived from hemp will have a similar distribution of terpenes, without any THC, THCV, CBD and CBDV.

Endocannabinoid Science and Clinical Effects

The endocannabinoid system (ECS) as a rather complex lipid signaling network in which different proteins play distinct roles in the control or in the modulation of numerous physiological and pathophysiological processes (Pertwee, 2005; Di Marzo, 2008). The ECS comprises classical cannabinoid receptors (CB1 and CB2), potentially also the orphan receptor GPR55, and arachidonic acid-derived ligands, which, however, also promiscuously target other receptors like, e.g., TRPV1 and PPAR-gamma (O'Sullivan, 2007; De Petrocellis and Di Marzo, 2010; Ross, 2009; Pertwee, 2010). More recently, the PPARγ has been reported as target of the CBG (Ki=11.7 µM) that at high concentrations, in the 10-25 µM range, may enhance the PPARγ transcriptional activity (Granja et al., 2012; Nadal et al., 2017) which stops metabolic reprogramming, aborting the transition to pain chronicity. Our body's endogenous cannabinoids, anandamide and 2-arachidonoyl glycerol, are present at very low levels and has a very short half-life due to the action of the enzyme fatty acid amide hydrolase (FAAH) which converts anandamide into ethanolamine and arachidonic acid. Monoacylglycerol lipase (MAGL) degrades 2-arachidonoyl glycerol. FAAH activity has been linked with arousability and aversive-memories extinction. Anandamide may help memory by helping us forget. The brain's ability to weaken unimportant memories and experiences enables it to function more efficiently. Both these enzymes have been shown to be promising therapeutic targets (Di Marzo, 2008). Finally, there appears to be an anandamide cellular reuptake mechanism that can be blocked by specific inhibitors (Di Marzo, 2008). Both cannabinoid receptor agonists and antagonists have actual or potential therapeutic applications (Di Marzo, 2008; Oesch and Gertsch, 2009; Pertwee, 2009), including its role in post-traumatic stress disorder (PTSD). The EDS consists of the endogenous cannabinoids (endocannabinoids), cannabinoid receptors and the enzymes that synthesize and degrade endocannabinoids that can maintain homeostasis. Many of the effects of cannabinoids and endocannabinoids are mediated by two G protein-coupled receptors (GPCRs), CB1 and CB2. CB1 receptors are present in very high levels in several brain regions and in lower amounts in a more widespread fashion. These receptors mediate many of the psychoactive effects of cannabinoids. CB2 receptors have a more restricted distribution, being found in a number of immune cells and in a few neurons. Both CB1 and CB2 couple primarily to inhibitory G proteins and are subject to the same pharmacological influences as other GPCRs. Thus, partial agonism, functional selectivity and inverse agonism all play important roles in determining the cellular response to specific cannabinoid receptor ligands.

Cannabinoids are defined as the terpeno-phenolic constituents of *Cannabis sativa* L and until recently, the phenyl-terpenoid Δ9-THC and some of its naturally occurring derivatives were the only plant natural products known to directly interact with cannabinoid receptors. By integrating with the EDS, exogenous cannabinoids, such ones from *Cannabis*, are used to reduce nausea and vomiting during chemotherapy, to improve appetite in people with HIV/AIDS, and to treat chronic pain and muscle spasms. *Cannabis*, its constituent cannabinoids, and terpenes are used to treat conditions or improve symptoms. Cannabinoids have been researched for their potential to affect stroke or children's epilepsy.

CB1 receptors are abundant and widely expressed throughout the central nervous system (CNS, i.e., the cerebellum, basal ganglia, hippocampus, cerebral cortex, and spinal cord) and they are responsible for the psychopharmacological and analgesic effects of THC. Of particular interest, CB1 receptors have high expression level in areas of the brain that are implicated in nociceptive perception, such as the thalamus and amygdala, the midbrain periaqueductal grey matter cells, basal ganglia and in the limbic system, including the hippocampus and the substantia gelatinosa of the spinal cord. They are also found in the cerebellum, spinal cord, peripheral nervous system, spleen, white blood cells, endocrine glands, gastrointestinal and urinary tracts and in both male and female reproductive systems. CB1 receptors are absent in the medulla oblongata, the part of the brain stem responsible for respiratory and cardiovascular functions, so its binding does not cause respiratory depression. The presynaptic localization of CB1 receptors enables cannabinoids to modulate neurotransmitter release such as dopamine, noradrenaline, glutamate, Gamma-aminobutyric acid (GABA), serotonin and acetylcholine. The activation of the CB1 receptors in the aforementioned brain areas modulates nociceptive thresholds and produces multiple biological effects by regulating the balance between excitatory and inhibitory neurotransmitters.

CB2 receptors have limited expression in peripheral nervous system (somatic and enteric autonomic sensory dorsal root ganglia, with some effect on wide dynamic range neurons), and CNS cells (microglia primarily in the cerebellum and brainstem); it is mainly expressed in peripheral tissues, including keratinocytes and the immune/lymphatic system, with the greatest density in the spleen, as well as in the pulmonary endothelial cells, bone (in osteocytes, osteoblasts and osteoclasts), cardiomyocytes, gastrointestinal, reproductive, adipose cells, keratinocytes (may release beta-endorphin with CB2 stimulation), eye trabecular meshwork cells, hepatic myofibroblasts (with cirrhosis), The distribution of CB2 receptors makes ligands less likely to be psychoactive. The CB2 receptor was shown to contribute to analgesia through suppressing the release of inflammatory mediators by cells located adjacent to nociceptive nerve terminals. In addition, activation of peripheral CB2 receptors blocks the transduction of pain signals into the CNS. Given that CB2 receptors are expressed in several types of inflammatory cells and immunocompetent cells, it is reasonable to assume that the activation of peripheral CB2 receptors may contribute to analgesic effect in conditions of inflammatory hyperalgesia and neuropathic pain with nocioplastic pain. Consistent with this notion, increased numbers of microglia/macrophage cells expressing CB2 receptor have been reported in spinal cords derived from multiple sclerosis (MS) patients, suggesting the involvement of CB2 receptor in the regulation of pain and CNS inflammation in MS patients. A potential mechanism through which CBG produces anxiolytic effects is due to the action of the endogenous cannabinoid anandamide (EAE) in the brain, which has been associated with the "runner's high."

A recent review substantiates the complexity of the field and highlight that other players, GPR55 for instance, are also targeted by cannabinoids (Solymosi and Kofalvi, 2017). G protein-coupled receptors (GPCRs) mediate the cellular response to neurotransmitters and hormones and are mostly responsible for taste, vision, and olfaction. The most prominent GPCRs that mediate endo- and phytocannabinoid signaling believed to be involved in signal transduction of the immune system are CB1, CB2, N-Arachidonyl glycine receptor (NAGly receptor, also known as GPCR18 associated with anti-inflammatory and other beneficial effects attributed to omega-3 fatty acid-rich diets), and GPCR55 (increases intracellular calcium and inhibits M currents), N-methyl-D-aspartate (NMDA) receptors (a glutamate receptor class, affecting breathing, locomotion, learning, memory formation, and neuroplasticity) and, α1-adrenoreceptors (selectively bind the catecholamines, norepinephrine and epinephrine in the sympathetic autonomic nervous system regulating blood pressure) and the activation of adenosine A2 (regulating myocardial oxygen consumption, coronary blood flow, and CNS neurotransmitters, which is similar to caffeine), and the peroxisome proliferator-activated gamma (PPAR-γ) receptors (which are linked to cellular differentiation, apoptosis, anticancer and anti-inflammatory responses).

Non-Psychoactive Cannabinoids

CBD and CBG may increase cannabinoid receptor activation indirectly by elevating endocannabinoid levels through its action on endocannabinoid (ECS) metabolism, which is homeostatic. Both CBD and CBG have the ability to inhibit fatty acid amide hydrolase (FAAH) enzyme, which metabolizes arachidonic acid-derived endocannabinoid anandamide (AEA), resulting in indirectly increasing CB1 receptor activation (this effect has been measurable, but it is believed that CBG has minimal direct binding of CB1 receptors), which may also have a favorable effect on lipid metabolism (inhibiting lipogenesis and boosting metabolism through increased number of intracellular mitochondria with increased activity), and insulin sensitivity; it may also reduce cardiac contractility and lower blood pressure in animals. CB1 receptor activation has been thought to mediate the ability of CBD and CBG to regulate long-term learned fear processing. ECS signaling is part of an endogenous anxiolytic neuro-modulatory system, thus inhibition of FAAH activity is a potentially promising therapeutic approach for reducing anxiety-related symptoms including post-traumatic stress disorder (PTSD). Moreover, CBD and CBG have been shown to block low-voltage-activated (T-type) Ca+2 channels, stimulate the glycine-receptor, and modulate the activity of FAAH. The action of CBD via these pathways may be responsible for the suppression of neuronal excitability and pain perception.

The acute anxiolytic effects of CBG at lower doses are also thought to involve serotonergic (5-HT 1A) activation (which is less of an effect with CBD). The activity of CBG at 5-HT1A receptors may drive its neuroprotective, antidepressive, and anxiolytic benefits, although the mechanism of action by which CBG decreases anxiety and increases the duration of sleep is still unclear.

The analgesic effect of CBD or CBG may be due to the modulation of the transient receptor potential vanilloid 1 (TRPV1), which is reversed by a TRPV1 activator. This receptor is a signal transduction of numerous chemical and physical stimuli and regulate many neural signaling processes and other physiological functions such as temperature sensation, smell, taste, vision, pressure, or pain perception, and dysfunctions can cause channelopathies. TRPs that are putative cannabinoid receptors are TRPV1-4, TRPA1, and TRPM8. This effect appears to be unique to CBG and CBD as well as a few other minor cannabinoids, whereas THC does not interact with this receptor channel.

In addition, Cannabinoids are positive allosteric modulators of the μ- and δ-opioid receptors (which modulate pain and immunologic function), suggesting the involvement of these receptors for an anti-nociceptive effect. In addition, there is evidence that CBD and CBG inhibits synapto-somal uptake of dopamine, noradrenaline, GABA (with anti-seizure and anti-anxiety effects), serotonin in addition to cellular uptake of anandamide (an endocannabinoid). The modulation of these neurotransmitters might explain the neuroprotective and the anti-nociceptive effects of CBD and CBG.

Moreover, cannabinoids have been shown to inhibit the cycloxygenase-2 enzyme and the production of arachidonic acid metabolites, prostaglandins, suggesting anti-inflammatory effects. Of note, the inhibition of cy-cloxygenase-2 was associated with an increase in the level of endocannabinoids, anandamide and 2-arachidonoyl glycerol (2-AG). This observation suggests that the suppression of cycloxygenase-2 enzyme by cannabinoids may not only decrease nociceptive and inflammatory prostaglandins but it may produce an indirect increase in the level of endocannabinoids, anandamide and 2-AG.

The appetite-stimulating properties of *Cannabis* are well documented and have been predominantly attributed to the hyperphagic activity of the psychoactive phytocannabinoid, Δ9-THC. However, other studies have shown cannabinoid products devoid of THC still stimulates appetite, indicating that other phytocannabinoids also elicit hyperphagia. The non-psychoactive CBG, which has affinity for several molecular targets with known involvement in the regulation of feeding behavior in rodents. CBG also elicits hyperphagia, by reducing latency to feed and increasing meal frequency, without producing negative neuromotor side effects.

Synthetic dimethylheptyl homolog of cannabigerol (CBG-DMH) displays hypotensive potential.

Interestingly, oral administration of *Lactobacillus acidophilus* was shown to combat inflammation and nociception through increasing the expression of the CB2 receptor in intestinal epithelial cells, suggesting that probiotics and cannabinoids might work together to halt inflammation and nociception. In support of this, it has recently been shown that THC reduces inflammation and adiposity in mice by increasing the accumulation of mucin-degrading bacteria, *Akkermansia municiphila*. Of relevance, *Akkermansia municiphila* supplementation was shown to reduce systemic inflammation in mice, further supporting the notion that microbiota contributes to the anti-inflammatory and analgesic effects of oral cannabinoids.

CBD has been shown to strengthen and increase bone growth preventing dental bone loss, as well potentially reversing or stabilizing minor tooth decay and alleviating tooth sensitivity that accompany eroding enamel. CBD can reduce inflammation and sensitivity to pain as well as minimize damage caused by gum disease gingivitis/periodontitis, which has been tested in animals so far. It can also reduce dental care anxiety. CBG can improve dental hygiene as it also has known effects to promote bone health, has anti-inflammatory, analgesic, antimicrobial against dental plaque and anxiolytic effects. This concept may be used as an ingredient for topical toothpaste applications or oral rinses.

THC also binds to CB2, but with less affinity than CB1. CBG and CBD bind primarily to CB2 receptors. Therefore, the pharmacological profile of CBG is very different from THC. CBG appears to hold benefits for neurologic disorders, especially degenerative and/or inflammatory conditions, in part, based on its CB2 binding. CBG is also known to have interactions with several other receptors in both the central and peripheral nervous systems. CBG has also shown some promise in colorectal polyps, as an antineoplastic, as well as with endometriosis. Reviews of the pre-clinical literature have also shown some preliminary ability to ameliorate cancer tumors, substance use disorder, pain, depression, as well as acting as an anti-inflammatory, antioxidant, analgesic, anti-arthritic, neuroprotective with cognitive enhancing properties, antidepressant, antidiabetic, as well as other clinical effects.

CBG given to mice with experimentally induced inflammatory bowel disease (IBD) showed therapeutic benefit in murine colitis, reduced nitric oxide production in macrophages (effect being modulated by the CB2 receptor) and reduced radical oxygen (ROS) formation in intestinal epithelial cells.

Borrelli, Francesca, Ines Fasolino, Barbara Romano, Raffaele Capasso, Francesco Maiello, Diana Coppola, Pierangelo Orlando et al. "Beneficial effect of the non-psychotropic plant cannabinoid cannabigerol on experimental inflammatory bowel disease." *Biochemical pharmacology* 85, no. 9 (2013): 1306-1316.

The ECS contributes to the control of intraocular pressure (IOP), by modulating both production and drainage of aqueous humor. CB1 receptors are located in the eye (McIntosh et al., 2007) and that functional CB2 receptors are also expressed in the retina and trabecular meshwork. There is a growing body of evidence of the involvement of this system in mechanisms leading to the death of retinal ganglion cells, which is the end result of glaucoma. Molecules capable of interfering with the ocular endocannabinoid system could offer valid alternatives to the treatment of this disease, based not only on the reduction of IOP but also on neuroprotection Nucci, Carlo, Monica Bari, Arnoldo Spanò, MariaTiziana Corasaniti, Giacinto Bagetta, Mauro Maccarrone, and Luigi Antonio Morrone. "Potential roles of (endo) cannabinoids in the treatment of glaucoma: from intraocular pressure control to neuroprotection." *Progress in brain research* 173 (2008): 451-464.

The presence of endocannabinoid receptors in structures of the eye responsible for formation and outflow of aqueous humor is an explanation for effectiveness of cannabinoids including CBG, when administered in topical form.

Contractions in mouse bladder that were induced by acetylcholine without significantly modifying the contractions induced by electrical stimulation were studied. The rank order of efficacy was CBG=THCV>CBD>CBDV, but not CBC. In depth studies on CBG showed that acetylcholine-induced contractions were not affected by CB1 or CB2 receptor antagonists. Additionally, CBG also reduced acetylcholine-induced contractions in the human bladder.

Interactions between moderate doses of CBG (as an antagonist) and CBD (as an agonist) may oppose one another at the 5-HT1A receptor in the regulation of nausea and vomiting in shrews.

Using CBG or CBD in combination with THC may mitigate some of the adverse effects of THC. There appears to be a growing reference for *Cannabis* products by shifting from dried herb (smoking) to *Cannabis* oil (which can be orally or sublingually ingested, vaporized or topically applied). For many "full spectrum" cannabinoid oils (including other phytochemicals) that are commercially available that contain CBG, an equal ratio of CBD/CBG is often available to consumers.

The absence of psychoactive THC components in the *Panakeia Cannabis sativa* L. reduces regulatory risk, and also reduces adverse impact on humans and animals that may come into contact with, or consume, the plant. In addition, adulterations of CBD can synthesize THC.

Psychoactive Cannabinoids

*Cannabis* products have been taken for thousands of years, and by tens of millions of Americans on a monthly basis. Due to federal and international regulations, the data on CBG has been thus far, limited. Current research indicates that any *Cannabis* usage, including experience with medical marijuana containing THC, in general, has a low overall risk of adverse events with short-term use. Unlike CBG, THC-containing products can result in psychoactive, cognitive or motor effects, and over time, a *Cannabis* use disorder and hyperemesis may occur.

These adverse events can potentially also occur with higher dosed CBD (due to accumulations of <0.3% THC content) as well as, if CBD is converted to Δ8-THC, which is now commonplace, resulting in detectable THC by drug toxicology testing. CBD has been also been converted to Δ9-THC in a patented process with a quantitative yield using boron trifluoride etherate as a Lewis acid in anhydrous CH2Cl2. The sensitivity of CBD to acidic conditions has led to the hypothesis that conversion of CBD to THC under the gastric acidic environment in vivo can cause adverse pharmacological effects from CBD-based marketed products. Two in vitro studies have used simulated gastric fluid to test the plausibility of this conversion. The first study reported the formation of THC in 2.9% yield along with other cannabinoid products in artificial gastric fluid without pepsin; and in another study, about 49% conversion into THC (both 8 and 9 isomers).

CBG Attributes

CBG is a supplement (not currently FDA classified as a drug) that can quality for the FDA's safety standard as "reasonable certainty of no harm" that has been hypothesized to have anti-inflammatory, antimicrobial, and anti-oxidant properties that binds to receptors of the brain, skin and immune system that can potentially benefit (improve or modulate) a host of serious conditions including those with circulatory problems and psychological distress. It was shown by Elsohly et al. in 1992 that CBG had antimicrobial properties (including antiviral) and more recently in 2005 Maor et al. described a synthetic analogue of CBG, CBG-dimethyl heptyl which possessed hypotensive and vasorelaxant properties.

CBG is non-psychoactive and not known to cause any euphoria or dependency and is devoid of withdrawal symptoms. It has minimal side effects (which can potentially be attributed to the other components of the product including minor cannabinoids, terpenes, flavonoids and the carrier oil) but may include gastrointestinal (GI) upset, appetite changes, constipation, diarrhea, lightheadedness, dry mouth, dry eyes, sedation, insomnia, lower heart rate, itching and possible serotonergic effects including tremors and mild agitation, male fertility problems and transient liver enzyme elevation; most of these possible side effects are most likely reversible within 1-2 days after discontinuation.

In a 2021 published clinical study, of 127 patient surveys using a CBG product (>50% in formulation): 73.9% claimed the superiority of CBG-predominant *Cannabis* over conventional medicines for chronic pain, 80% for depression, 73% for insomnia, and 78.3% for anxiety; 44% reported no adverse events, with 16.5% noting dry mouth, 15% sleepiness, 11.8% increased appetite, and 8.7% dry eyes. Around 84.3% reported no withdrawal symptoms, with sleep difficulties representing the most frequently endorsed withdrawal symptom (endorsed by two respondents).

Russo, Ethan B., Carrie Cuttler, Ziva D. Cooper, Amanda Stueber, Venetia L. Whiteley, and Michelle Sexton. "Survey of Patients Employing Cannabigerol-Predominant *Cannabis* Preparations: Perceived Medical Effects, Adverse Events, and Withdrawal Symptoms." *Cannabis and Cannabinoid Research* (2021).

CBG has minimal adverse effects due to its limited cytochrome P450 hepatic metabolism pathways, and therefore, it has less predicted drug to drug interactions than CBD. It appears that CBG with chronic use and at higher doses is nontoxic, does not induce changes in food intake or catalepsy, does not affect physiological measures, and does not alter psychomotor or psychological functions. Thus far, CBG demonstrates no potential for abuse or dependence in humans; hence it is not "psychoactive," and their products or derivatives cannot be adulterated.

CBGA (along with CBGVA, found in lower titers) is the precursor to all cannabinoids in legal hemp (*sativa*) and predominantly converts to unstable CBDA (CBDVA), which has generally similar (but not the same) pharmacologic properties as CBD (CBDV), through heating or hydrolysis. Through an extraction process, the smaller concentration of CBG as found in the full spectrum CBD oil can be isolated, and is used as a supplement, but it still may contain THC (<0.3%), as allowable through Federal standards. CBG, with higher yields, can now be derived from a proprietary legal hemp plant, *sativa* L., "*Panakeia*", in which there is no THC and no CBD content.

CBG is now considered a dietary supplement which has recently been included in European Union cosmetics database as "generally recognized as being safe" (GRAS), although clinical studies are currently being performed to evaluate its tolerability, dosing and side effects profile. There is a greater experience with CBG is Israel, without reports or warnings of any significant toxicity. CBG, whether isolated or full spectrum content, is commercially available in the *Cannabis* market, and is federally legal if derived from a hemp plant.

A consensus for the maximum accepted medical *Cannabis* dose is usually 120 grams per month (with a maximum of 30% THC content=36000 mg/month or 1200 mg/day) in many states, of which there is an estimated a maximum content of 1% CBG in classified products from these dispensaries. This would extrapolate to 12 mg/day (recently FDA has considered cannabinoid products in 5 mg increments, which would represent 2.5 units) of CBG, which is considered safe by state dispensaries, and has been recommended by licensed and approved providers and dispensaries. Alternatively, there are published contents of full spectrum CBD oil which can contain CBG at 4%, which is GRAS. If oral intake is 200 mg/day of this product, it would include 8 mg/d of CBG (1.8 units). Some patients may consume high dose full spectrum CBD oil at 2500 mg/d (CBG=100 mg/d or 20 units) without adverse events. There have been clinical and animal studies conducted at higher CBG dose ranges, in which side effects were minimal and no toxicity was observed.

Various patents and scientific publications are available providing different dosages of phytocannabinoids for disease or symptoms treatment. For instance, Epidiolex-CBD is used to treat childhood epilepsy (GB2548873) within the recommended FDA dosage range of 5-25 mg/kg/day, using a gradual titration formula. With maximum titration, in a 50 kg weight person, this would be 1250 mg/day of CBD (=12.5 ml/day of, or 250 units, given in 2 divided doses), which is a significant quantity to be consumed.

For the food additive safety evaluation, an acceptable daily intake (ADI) level is based on the highest no observable adverse effect level (NOAEL) for the most sensitive non-cancer toxicity end point as determined from any pivotal nonclinical study with application of an appropriate safety factor, and determination of the estimated daily intake (EDI) level. Comparing the ADI to the EDI, a safety determination (reasonable certainty of no harm) can be made.

Full Spectrum *Cannabis sativa* L (Hemp)-Derived Oil

In addition to cannabinoids, hemp or *Cannabis* biomass contains various terpenes such as terpineol, limonene, myrcene, terpinolene, humulene and sesquiterpenes. When terpenes are modified chemically, by oxidation or rearrangement of the carbon skeleton, the resulting compounds are generally referred to as terpenoids. All cannabinoids are terpenoids, but not all terpenoids are cannabinoids. Terpenes and terpenoids, including cannabinoids, are generally non-polar substances and hence soluble in lipids. Some authors use the term "terpene" more broadly, to include terpenoids.

Terpenes display unique therapeutic effects that may contribute meaningfully to the entourage effects of *Cannabis*-based medicinal extracts. It has been hypothesized that some terpenes could attenuate undesirable effects of THC (Russo, 2011). Terpenes, not cannabinoids, are responsible for the aroma and flavor of *Cannabis*. Monoterpenes usually predominate (limonene, myrcene, pinene), but these headspace volatiles (Hood et al., 1973), while only lost at a rate of about 5% before processing (Gershenzon, 1994), do suffer diminished yields with drying and storage (Turner et al., 1980; Ross and ElSohly, 1996), resulting in a higher relative proportion of sesquiterpenoids (especially caryophyllene), as also often occurs in extracts.

The *Cannabis* "entourage effect" is believed to increase the effectiveness of all cannabinoids as a synergistic therapy, which incorporates the interaction of different cannabinoids and terpenes, and was introduced in cannabinoid science in 1998 by S. Ben-Shabat, with Raphael Mechoulam, to represent a novel endogenous cannabinoid molecular regulation route.

Other Non-*Cannabis* Derived Phytochemicals Affecting ECS

In the last few years, in an emerging field of research has recognized numerous non-cannabinoid plant natural products have been reported to act as cannabinoid receptor ligands.

"Phyto-cannabinoids" can be defined as any plant-derived natural product capable of either directly interacting with cannabinoid receptors or sharing chemical similarity with cannabinoids or both. Direct cannabinoid receptor ligands are compounds that show high binding affinities (in the lower nM range) for cannabinoid receptors and exert discrete functional effects (i.e., agonism, neutral antagonism or inverse agonism). By contrast, indirect ligands target either key proteins within the ECS that regulate tissue levels of endocannabinoids or allosteric sites on the CB1 receptor, which modulate the ECS. Certain plant natural products, including some cannabinoids, possess at least some of these properties.

Despite the fact that N-acyl-ethanolamines (NAEs) from plants do not directly interact with CB receptors (plants do not generally produce arachidonic acid, which is the acyl scaffold favored for CB interaction) they have been shown to inhibit FAAH, thus leading to an increase in endocannabinoid tone. N-linoleoyl-ethanolamide and N-oleoyl-ethanolamide, which are found not only in chocolate (*Theobroma cacao* L.) but also other plants (Di Marzo et al., 1998), and the widespread NAE palmitoyl-ethanolamide, inhibit anandamide breakdown (Maurelli et al., 1995; Di Tomaso et al., 1996).

Certain N-alkylamides (alkamides) from *Echinacea* spp. have been shown to interact functionally with the human CB2 receptor with low nM to µM Ki values (Gertsch et al., 2006). These N-isobutylamides selectively act at the CB2 receptor over the CB1 receptor, leading to an increase in intracellular calcium which could be blocked by the selective CB2 receptor inverse agonist SR144528 ((1S-endo)-5-(4-Chloro-3-methylphenyl)-1-((4-methylphenyl)methyl)-N-(1,3,3-trimethylbicyclo(2.2.1)hept-2-yl)-1H-pyrazole-3-carboxamide), but they do not modulate the Gαi signaling pathway. Intriguingly, CB2 receptor-binding N-alkylamides show similar anti-inflammatory effects as anandamide (e.g., inhibition of TNF-α) at low nM concentrations (Raduner et al., 2006). Certain *Echinacea* N-alkylamides inhibit anandamide reuptake in vitro (Chicca et al., 2009). Like anandamide, N-alkylamides also target PPAR-gamma (Spelman et al., 2009). Different *Echinacea* N-isobutylamides are orally bioavailable resulting in nM plasma levels in humans (Woelkart et al., 2008).

The polyacetylenic polyyne falcarinol, which is found in different plants of the Apiaceae family (e.g., in carrots) shows significant binding interactions with both cannabinoid receptors, but appears to selectively undergo an alkylation reaction with the CB1 receptor (Ki value<1 µM), leading to relatively potent inverse agonistic and pro-inflammatory effects in human skin (Leonti et al., 2010).

Finally, it has been proposed that certain dietary fatty acids, which can also be found in plants, can modulate the ECS by influencing the availability of phospholipid biosynthetic precursors of endocannabinoids (Banni and Di Marzo, 2009).

The bicyclic sesquiterpene, β-caryophyllene (trans-isomer), which is a plant volatile, and very frequently found in plants, has been shown to selectively target the CB2 receptor at nM concentrations (Ki=155 nM) and to act as a full agonist (Gertsch et al., 2008). Remarkably, β-caryophyllene is also a major compound in *Cannabis sativa* L. essential oil. Thus, *Cannabis* produces two entirely different chemical scaffolds able to differentially target CB receptors. While studies on the pharmacokinetics of β-caryophyllene are still ongoing, it is already clear that this cyclobutane-ring containing terpene is readily bioavailable, and, unlike many polyphenolic natural products, is not metabolized immediately but shows a Tmax>1 h after one single oral administration (J. G., unpublished data). Orally administered β-caryophyllene (<5 mg·kg-1) produces strong anti-inflammatory and analgesic effects in wild-type mice but not in CB2 receptor knockout mice, which is a clear indication that it may be a functional CB2 ligand. Ongoing studies show that β-caryophyllene is effective at reducing neuropathic pain in a CB2 receptor-dependent manner (Zimmer et al., 2009). Therefore, the FDA approved food additive β-caryophyllene has the potential to become an attractive candidate for clinical trials targeting the CB2 receptor (Gertsch, 2008). Interestingly, the diterpene salvinorin A from *Salvia divinorum* Epling & Jativa-M (Table 1) has been reported to be a selective high-affinity kappa-opioid receptor (KOP) agonist, but recent data also suggest that it may interact with a putative CB receptor/KOP heterodimer which may be formed during inflammatory conditions (Fichna et al., 2009). To date, binding experiments have shown that salvinorin A has very low affinity for homomeric cannabinoid receptors and does not inhibit endocannabinoid degradation (Capasso et al., 2008).

More recently, two naturally occurring quinonoid triterpenoids, pristimerin and euphol, were found to inhibit acylglycerol lipase, MAGL, with high potency (IC50=93 nM and 315 nM respectively) through a reversible mechanism (King et al., 2009). As this class of triterpenes is relatively frequent in nature, it may not be unusual to find 'indirect' rather than 'direct' agonists of cannabinoid receptors among plant secondary metabolites. Several distinct triterpenes are known to modulate immune functions through yet unknown mechanisms (Rios, 2010) and it will thus be interesting to see in a more systematic study whether other similar triterpenoids are also able to inhibit MAGL.

Catechin-derivatives (e.g., epigallocatechin 3-gallate and (−)-epigallocatechin) were shown to bind to human cannabinoid receptors rather non-selectively at high µM concentrations (Korte et al., 2010). Catechins are very widespread plant secondary metabolites which may provide nutritional health benefits.

Plant polyphenols, such as phenylpropanoids (e.g., epigallocatechin 3-O-gallate, curcumin, resveratrol) possess chemical scaffolds which at µM concentrations bind to protein targets in vitro with limited specificity. This is clearly reflected by numerous reports on protein binding interactions that such compounds undergo in the µM range (Anand et al., 2008; Bisht et al., 2009). At the macroscopic level, polyphenols (i.e., tannins) have been used to tan leather by denaturing of proteins, and at the microscopic level µM concentrations of polyphenols interact with multiple protein binding sites (via their hydroxyl groups) non-specifically and therefore such compounds score as frequent hitters in vitro. The great majority of established cannabinoid receptor ligands are highly lipophilic, which reflects the nature of the active site within cannabinoid receptors. Thus, hydrophilic polyphenols like catechins and anthocyanidins would clearly be atypical cannabinoid receptor ligands.

Certain flavonoids inhibit fatty acid amide hydrolase (FAAH), which is the enzyme responsible for the breakdown of the endogenous CB receptor ligand anandamide (Thors et al., 2007; 2008). Both the isoflavonoid, genistein, and the flavonoids: kaempferol, 7-hydroxyflavone and 3,7-dihydroxyflavone have been shown to concentration-dependently inhibit anandamide hydrolysis in rat brain homogenates, albeit at relatively high concentrations (IC50 values between 2 and 10 µM). A preliminary structure-activity relationship shows 7-hydroxyflavone being the most potent inhibitor ($IC_{50}$ value<1 µM).

An abundant literature is devoted to mechanisms underlying the biological activity of plant polyphenols (Landis-Piwowar and Dou, 2008; Bisht et al., 2009). However, although most beneficial and potentially therapeutic effects of trans-resveratrol, curcumin, catechins and kaempferol-type flavonoids are typically detected in the low µM range in vitro, all such compounds show limited bioavailability and poor pharmacokinetics in vivo with reported plasma concentrations in the low nM range (DuPont et al., 2004; Garcea et al., 2004; Boocock et al., 2007).

There are other natural plant products have been shown to bind weakly to the CB2 receptor. These include the coumarin derivative rutamarin from the medicinal plant *Ruta graveolens* L. (Rollinger et al., 2009) and 3,3'-diindolylmethane (DIM) (Table 2), which is an anticarcinogenic metabolite generated by ingestion of indole-3-carbinol. Indole-3-carbinol is commonly found in *Brassica* vegetables. DIM has been shown to be a weak CB2 receptor partial agonist (Yin et al., 2009).

Plants produce fatty acid amides, some of which are able to inhibit the degradation of anandamide but do not generally bind with significant affinity to CB receptors (Gertsch et al., 2006; Di Marzo et al., 2007). At present, the only phytocannabinoid that has been discovered to also exist in plants other than *Cannabis* is β-caryophyllene, which is among the most abundant plant essential oil components, and could be considered as a true CB2 receptor-selective *Cannabis* constituent.

Palmitoylethanolamide (PEA, N-(2-hydroxyethyl) hexadecamide, palmidrol; has a structure that belongs to the family of N-acylethanolamines (NAEs), an endogenous biologically active lipids including the endogenous cannabinoid receptor ligand anandamide and the satiety factor oleoylethanolamide. PEA was first identified in the 1950s as being an active anti-inflammatory agent in chicken egg yolk, and also found in peanuts. It is primarily an endogenous lipid agonist of the nuclear receptor peroxisome proliferator-activated receptor-α (PPAR-α) and its degradation is catalyzed by cysteine hydrolase N-acylethanolamine acid amidase (NAAA). The activation of PPAR-α by exogenous PEA attenuates pain and inflammation, and stimulates mitochondrial respiration. PEA shows efficacy in a variety of pain models in animals including carrageenan- and prostaglandin-induced hyperalgesia the formalin test of persistent pain, visceral hyperalgesia produced by instillation of nerve growth factor into the bladder and the sciatic nerve ligature model of neuropathic pain, whereas the acute thermal pain response is not affected. It may mitigate the transformation from acute to chronic pain states. Other proposed mechanism(s) of action of PEA involve effects upon mast cells, CB2-like cannabinoid receptors, adenosine triphosphate (ATP)-sensitive potassium (K+)-channels, TRP channels, and Nuclear Factor kappa-light-chain-enhancer of activated B cells (NFkB) family of proteins, It is also an agonist with G protein-coupled receptor 119 (GPR119), an orphan receptor expressed predominantly in the pancreas (β-cells) and gastrointestinal tract (enteroendocrine cells involved in glucagon-like peptide-1 secretion) and will, at least in theory, affect endocannabinoid signaling by acting as a competing substrate for the endocannabinoid homologue anandamide (N-arachidonoylethanolamine); these actions are shared by the endogenous N-oleoylethanolamine N-stearoylethanolamine (NAEs). The pharmacokinetic properties of PEA suggests that the compound has a high volume of distribution. Perhaps the most intriguing finding was the concentration of label in the hypothalamus after oral dosing of PEA tritiated in the acyl side chain in rodents. PEA may potentially be useful in a wide range of therapeutic areas, including eczema, pain and neurodegeneration and at the same time to be essentially devoid of unwanted effects in humans veterinary use (skin conditions, Redonyl™, [Innovet]) and as a nutraceutical in humans (Normast™, Pelvilen™ [Epitech]), PeaPure™ [JP Russel Science Ltd]) in some European countries (e.g. Italy, Spain; it is sold as a food supplement in other countries, such as the Netherlands). It also is a constituent of a cream (Physiogel AI™, Stiefel) marketed for dry skin.

Epitech (the makers of Normast and other PEA preparations) researchers, obtained raw data from corresponding authors of 12 studies (six published in journals, two published abstracts and four manuscripts either in preparation or submitted for publication) that met the inclusion criteria (including availability of raw data and comparable methods for assessing pain intensity). The authors concluded on the basis of their analyses that PEA, (primarily from ultra-micronized or micronized PEA) was an effective treatment for pain with no registered serious adverse effects. Their analysis was based upon 12 studies that met their inclusion criteria (three placebo-controlled double-blind studies, two open-label randomized vs. standard therapy and seven open-label studies without a comparator) in patients with a variety of etiologies. Several outcomes were presented, of which a key finding was the difference in the number of patients achieving <3 in the pain assessment using numeric rating scale/visual analog scale (NRS/VAS) scores (55/263 [20.9%] for the controls, 760/1138 [66.7% of the PEA treatment groups). The fact that approximately half of the included patients came from the open-label studies (703/30 PEA/control vs. 266/485 PEA/control for the double blind studies) is perhaps a weakness of the study, although a Cox survival analysis (reduction in pain intensity to <3 on an NRS/VAS scale as endpoint) favored both PEA over control and the double blind over the open-label studies (other factors with modest, but significant effects in this analysis were gender and age (<65 vs. >65); pain etiology did not contribute significantly to the analysis). The only adverse event (not necessarily drug-related) that has been reported was for a patient treated with 300 mg Normast™ following impacted third molar extraction and appears coincidental. In a well powered study, Guida et al. found with lumbo-sciatic algias using 300 or 600 mg Normast, there was a significant reduction of VAS scores on day 21 from 6.6±1.7 (means±SD) to 4.6±1.7 for placebo; 6.5±1.9→3.6±1.8 for 300 mg PEA and 7.1±1.8→2.1±1.7 for 600 mg PEA. Similar results were found for Roland-Morris disability questionnaire (measures back pain and functional deficits), with few treatment dropouts. All in all, the data point to efficacy of PEA over placebo (assuming no publication bias), but more information is needed to be able to gauge this efficacy vs. current treatment regimes.

Linda Gabrielsson, Sofia Mattsson, and Christopher J. Fowler Palmitoyl-ethanolamide for the treatment of pain: pharmacokinetics, safety and efficacy Br J Clin Pharmacol. 2016 October; 82(4): 932-942, 2016 Jun. 29. doi: 10.1111/bcp.13020.

Cannabinoid Bioavailability

CBD, a lipophilic molecule, when concomitantly consumed with a balanced diet, becomes more bioavailable, especially with a fatty meal. CBD bioavailability from smoked product may be around 31% (range=11%-45%). Oral absorption has more variability and lower bioavailability approximately 6% in humans (with extensive first pass enterohepatic metabolism and its metabolites are mostly excreted via the kidneys), with sublingual bioavailability of 13-19% (avoids first pass effect, with higher absorption through the oral mucosa, but some of the product is also swallowed), and about 10% transdermal absorption (bypasses first pass). Acute effects may proceed on a time scale, but CBD has also been reported to have a long terminal elimination half-life, with the average half-life post inhalation of 31±4 hours and from 2 to 5 days after repeated daily oral administration.

Potential avenues to overcome these issues with CBD include self-emulsifying drug delivery systems, improved crystal formulations and other solid-state delivery formulations. High fat meals also potentially inhibit the activity of drug efflux transporters present on the apical membrane of enterocytes, and stimulate the release of biliary secretion, which further inhibits efflux transporter activity.

Medium-chain triglycerides (MCT) oil is completely devoid of any lipid oxidation products, and tend to be less susceptible to oxidative degradation than olive oil or hemp seed oil. Oxidation causes rancidity and deterioration of fats, as well as decreased concentrations of cannabinoids and terpenes. The high oral doses that are required for efficacy may impact the occurrence of adverse events (AEs), as well as increasing drug costs to the healthcare provider or patient. In one randomized controlled trial in treatment resistant epilepsy, AEs were reported in 93% of patients taking pharmaceutical CBD and included vomiting and diarrhea, while 86% of patients in another trial reported similar AEs; in other clinical studies, there are mild side effects reported in 33% of those surveyed taking CBD-rich extracts. It is unclear whether CBD-rich extracts demonstrate a more favorable side effect profile due to the presence of non-standardized herbal compositions, improved absorption of the CBD in the more complex mixture of compounds or whether it is due to the lower doses of individual cannabinoids reportedly consumed, as well as the procurement of data (controls vs reports).

Bioavailability can be enhanced with self-emulsifying drug delivery systems (SEDDS). These involve mixtures of oils, surfactants, and solvents that produce nano or micro sized droplets when they come into contact with an aqueous solution such as in the gut demonstrated greater bioavailability (about 31-34% higher compared to a reference oromucosal spray), solubility, and faster time to peak plasma concentrations in humans, with high inter-individual variations.

VESIsorb® is a novel lipid-based delivery system which self-assembles on contact with an aqueous phase into a colloidal delivery system, which solubilizes the drug and improves diffusion and absorption and thus bioavailability. In rats, testing of a nano-emulsion (NE) formulation increased absorption and bioavailability (21% higher). Echo Pharmaceuticals (Arvisol, using their lipophilic compound delivery technology Alitra®) and Ananda Scientific (Ananda's Liquid Structure™ Enhanced CBD) are also investigating formulations which claim to enhance bioavailability and consistency in PK profiles by increasing CBD's water solubility.

Another encapsulated form of CBD is APH-1501 (produced by Aphios), which are time-released capsules in which CBD is encapsulated in biodegradable polymer nanospheres as a lyophilized powder. A novel crystalline CBD: (R,R)-(−)-crystalline cannabidiol has a melting point of 37-50° C., compared with a melting point of 66-67° C. for CBD which may increase aqueous solubility. Artelo Biosciences have patented a co-crystal with CBD using tetramethylpyrazine (TMP), a plant-derived compound from the *Ligusticum* species, by acting synergistically and changing the physiochemical properties that are associated with ineffective absorption is currently in the nonclinical phase of pharmaceutical development targeted towards post-traumatic stress disorder (PTSD), inflammatory bowel disease (IBD), stroke and rare diseases.

Co-crystals can be "fine-tuned" using various inert or pharmacologically active co-formers, which may provide a more predictable pharmacokinetic profile and subsequently reduce side effects associated with high intra- and interpersonal variability.

"TurboCBD" claims to result in increased circulating CBD levels compared to control CBD, and contains American *Ginseng, Ginkgo biloba*, and organic hemp oil, produced using DehydraTECH™ delivery technology.

Preveceutical's "Sol-Gel" is exploring an intranasal CBD formulation to increase bioavailability.

A CBD gel, "Zygel" is being promoted for transdermal application in phase 2 trials.

Botanix pharmaceuticals are exploring a number of gel formulations for transdermal application in indications such as acne, psoriasis and dermatitis.

Kalytera has developed an L-valine-ester derivative of CBD for topical delivery, which is in pre-clinical stages, as well as a bi-sulphate derivative of CBD for oral delivery which claims to be water soluble, a bi-phosphate CBD derivative aimed for intra-tracheal delivery via a novel aerosolised formulation, and an intravenous (IV) formulation.

GW Pharmaceuticals list an IV formulation in phase 1 trial for neonatal hypoxic-ischemic encephalopathy (NHIE).

A sublingual formulation by Diverse Biotech Inc., and an oral liquid by Emerald Health Pharmaceuticals containing a pure synthetic CBD are being studied.

Complexation of CBD with cyclodextrins (CD) has also been investigated as a potential method to increase the water solubility and subsequently improve the bioavailability of sublingually delivered CBD, which has been comparable to CBD delivered in an ethanol solution sublingually.

Two formulations of CBD and CDs are currently in development by Medexus pharmaceuticals and Vireo health LLC. These companies propose complexes of CBD and CDs will increase the aqueous solubility and subsequently improve bioavailability.

A nanoemulsion preparation of CBD (CBD-NE) consisted of vitamin E acetate, ethanol, Tween-20, and distilled water, to improve the poor solubility and absorption of CBD compared in an olive oil solution. The pharmacokinetic profiles of CBD in rats were evaluated after oral administrations of CBD-NE successfully improved the absorption of CBD regardless of bile secretion, especially with the time of onset and the amount absorbed.

These technologies to improve CBD bioavailability can be applied to CBG products.

The bioavailability of CBD can be increased by using supplemental terpenes (Limonene, Alpha-pinene, Menthol, Myrcene and Beta-caryophyllene). However, when consumed with some supplemental herbs (Chamomile flowers; Spicey peppers-capsaicin; turmeric and black pepper-piperine), the compound's bioavailability increases even more. Today, nanotechnology is used to create new types of CBD products, which are essentially emulsified. The process of emulsification breaks down CBD molecules into small ones. In short, the process micronizes them. It is carried out using an oil or water-based product. The tinier and more dispersed the CBD molecules become, the more bioavailable CBD is, with up to 35% sublingually absorbed.

Piperine is an alkaloid naturally found in black pepper (fruit or berries of *Piper nigrum* L with a 2.5%-3.0% yield) with a myriad of pharmacological attributes. Piperine's most far reaching indication is drug absorption enhancement, with supportive data regarding its ability to inhibit first pass effect mechanisms and secondarily as a metabolic inducer. There was no significant difference in piperine's effect, when given chronically or in a single dose regimen. Both groups resulted in approximate 2.5-fold increase in oral bioavailability of CBD compared to control group without piperine. There is limited data on CBG/CBGA bioavailability. However, based on its chemical structure and lipophilicity, it can be anticipated that similar bioavailability properties can be extrapolated to full spectrum or isolated CBG products. See, Dvora Izgelov, Abraham J Domb, Amnon Hoffman, The effect of piperine on oral absorption of cannabidiol following acute vs. chronic administration, doi: 10.1016/j.ejps.2020.105313. Epub 2020 Mar. 19, 2020 May 30; 148:105313. PMID: 32198013DOI: 10.1016/j.ejps.2020.105313

White pepper contains a chemical called piperine (consists of approximately 4.0-4.5%, with at least 98% purity). Piperine as an active chemical constituent, which seems to have many effects in the body with diverse biological activities, such as anti-inflammatory, analgesic, anti, 35r, antiviral, anti-larvicidal, pesticide, anti-Alzheimer's, antidepressant, improve breathing, hypotension, vascular cell modulation, antipyretic, anti-ulcer/anti-emetic, anti-spasmotic, antidiabetic, improves lipid metabolism and may improve weight loss, anti-vitiligo agents, anti-allergic agent (by reducing mast cell activation), antidepressant and most importantly, as the bioavailability enhancer, including inhibition of the gastric emptying of solid and/or liquid diets and the gastrointestinal transit; has been studied to improve seizure control with anticonvulsants (CBD and CBGA, which has known anti-seizure activity). The ripe berries for white pepper are processed using a procedure known as "retting." Color is only a superficial difference between black and white pepper. The flavor profile of white pepper differs from black pepper with a distinctive earthy, barnyard-like flavor and aroma that is not typically found in black pepper.

There are newly synthesized CBG derivatives: 1",1"-Dimethylheptyl-monomethoxycannabigerol (HUM-223) by substituting dimethylheptyl pentyl (DMH) at position 5 of CBG resulting in a monomethoxy CBG-DMH; and Monomethoxycannabigeroyl-3-morpholinoproprionate (HUM-234) is synthesized by substituting morpholinopropionic acid from monomethoxy-CBG (a derivative of HUM-223). They possess anti-inflammatory and analgesic properties in animal models. In addition, unlike CBG, HUM-234 also prevents obesity in mice fed a high-fat diet (HFD) suggesting that HUM-234 and related compounds may have potential to treat metabolic disorders including liver disease. Maleic acid converts HUM-234 oil into Monomethoxycannabigeroyl-3-morpholinopropraonate Maleate (HUM-233), a solid salt at room temperature, which also increases its bioavailability. HUM-233 was able to reduce TNF-$\alpha$ levels; however, HUM-234 showed an opposite trend at elevated doses.

Cannabinoid Science and Covid-19

COVID-19, the disease caused by SARS-Cov-2, a novel coronavirus first reported in Wuhan China in 2019, causes significant morbidity and mortality, and has triggered a global pandemic.

Binding of the SARS-CoV-2 virus to angiotensin-converting enzyme 2 (ACE2) leads to the internalization of ACE2 and activation of angiotensin II resulting in the activation of nuclear factor kappa B (NF-$\kappa$B). Subsequently, cytokines IL-6, TNF$\alpha$, IL-1$\beta$, and IL-10 will be produced which might lead to local lung dysfunction with severe T-lymphocyte apoptosis, with lymphocytopenia, as well as a rise in blood pressure, which contributes to lung injury and deterioration of pulmonary function, as occurs in acute respiratory distress syndrome (ARDS). Researchers from Italy in 2017 examined the potential of a hemp seed protein isolate that was prepared from defatted hemp seed by alkaline solubilization/acid precipitation as inhibitors for angiotensin-converting enzyme 2 (ACE-2). All four peptides extracted from hemp seed oil had ACE-inhibitory activity a potential agent to inhibit entry of SARS-CoV2 into the cells.

It was reported that exogenously added 2-AG leads to the attenuation of lymphocyte proliferation through the decrease of lymphocytes T helper cells (Th)1- and Th17-associated cytokines IL-6, IL-2, and tumor necrosis factor (TNF)$\alpha$. Moreover, activated lymphocytic B and T cells that produce high levels of 2-AG inhibit in a feedback loop T cell activation and proliferation, making exogenously applied 2-AG a putative candidate for therapeutic usage in Th1- or TH17-dependent diseases. Upon antigen activation by pathogens, macrophages, and dendritic cells produce and release 2-AG, which results in the upregulation of 2-AG levels in the serum and lymph nodes of mice during vaccination CB2 dependently. In a murine immunization model, transient administration of CB2 antagonist AM630 or inverse antagonist JTE907 increased the intensity of antigen-specific immune responses by upregulation of immunomodulatory genes in secondary lymphoid tissue. AEA inhibited macrophage-mediated killing of the TNF$\alpha$-sensitive mouse alveolar macrophage cell line L929. Correa et al. presented evidence that AEA inhibited expression of pro-inflammatory cytokines like IL-12 and IL-23 in in vitro models of immune disorders and increased the anti-inflammatory cytokine IL-10 in activated mouse microglia. In a model of acute intestinal inflammation, it was shown that the transporter p-glycoprotein helped the influx of endocannabinoids into the intestinal lumen, which inhibited the migration of neutrophils by counteracting the pro-inflammatory neutrophil chemoattractant eicosanoid hepoxilin A3. Similarly, the migration-related transcriptional profile of neutrophils was enhanced in $CB2^{-/-}$ mice.

Endocannabinoid receptors CB1 and CB2 were expressed by bone marrow derived hematopoietic stem cells and $CD34^+$ cells. AEA and 2-AG were detected in the microenvironment of peripheral blood and bone marrow, which were secreted by bone marrow mesenchymal stem cells. Migration of hematopoietic stem cells was stimulated by AEA and 2-AG and blocked by CB receptor antagonists rendering endocannabinoids putative candidates for the enhancement of the migration of hematopoietic stem cells extracts of the phyto-cannabinoids CBD and THC could attenuate the proliferation of activated lymphocytes and the secretion of pro-inflammatory IL-17, thereby increasing secretion of the anti-inflammatory IL-10. Additionally, the endocannabinoid AEA and the phyto-cannabinoid THC could also induce immunosuppression in B cells as was examined in both primary and secondary in vitro plaque-forming cell assays of antibody formation. Many reports have shown that exogenously applied CBD suppresses transcription factors involved in inflammation like Nuclear Factor of activated T-cells (NFAT), Activator protein 1 (AP-1), and NF-κB, which results in a broad repression of cytokines like interleukin (IL)-6, IL-1β, IL-1α, granulocyte-macrophage colony-stimulating factor (GM-CSF), and TNFα in diverse cells and tissues. These cytokines have a central role in the development of cytokine release storm (CRS) in COVID-19. IL-6 promotes the differentiation of Th17 cells, which was shown to be suppressed by CBD. Moreover, CBD was shown to inhibit type II interferon (IFNγ).

In murine models of chronic asthma, cytokine levels of IL-4, IL-5, IL-6, IL-13, and TNFα were decreased by CBD, probably exerting its effect via the CB1 receptor. This led to the reduction of airway inflammation and fibrosis. Moreover, the production of regulatory T cells was increased in murine models of inflammatory diseases.

These anti-inflammatory actions of *Cannabis* might be beneficial for the prevention of CRS before the host inflammatory response turns pathological during the transition from mild to critical disease in COVID-19 patients.

Thus, full spectrum *Panakeia* extract, administered through the use of alternative routes of *Cannabis* administration like vaporizing or edibles, is a novel anti-inflammatory therapy, predicted to prevent infection with SARS-Cov2, or mitigate symptoms of Covid-19, both in the respiratory and digestive tracts via inhibition of hyperinflammation.

Researchers have reported that *Cannabis sativa*, especially extracts high in the anti-inflammatory cannabinoid cannabidiol (CBD), has been found to alter gene expression and inflammation and harbor anti-cancer and anti-inflammatory properties. The Canadian researchers, from a range of institutions including the University of Lethbridge and University of Calgary, developed over 800 new *C. sativa* cultivars and hypothesized that high-CBD rich *C. sativa* extracts may be used to down-regulate ACE2 expressions in target COVID-19 tissues. The ACE2 receptor that SARS-CoV-2 and other coronaviruses use to access host cells is expressed in a range of tissues, including the lung, nasal mucosa, kidney and gastrointestinal tract. One recent study reported high levels of ACE2 expression in oral epithelial tissues and suggested that the oral cavity could be an important target for prevention strategies. Some *C. sativa* extracts down-regulate serine protease Transmembrane Serine Protease 2 (TMPRSS2), another critical protein required for SARS-CoV-2 (the virus that causes Covid-19 infection) entry into host cells.

"In search of preventive strategies: novel high-CBD *Cannabis sativa* extracts modulate ACE2 expression in COVID-19 gateway tissues" by Bo Wang, Anna Kovalchuk, Dongping Li, Rocio Rodriguez-Juarez, Yaroslav Ilnytskyy, Igor Kovalchuk and Olga Kovalchuk, 22 Nov. 2020, Aging-US.

CBD and its metabolite, 7-OH-CBD by CYP2D6, but not congeneric cannabinoids, potently 5 block SARS-CoV-2 replication in lung epithelial cells. CBD acts after cellular infection, inhibiting viral gene expression and reversing many effects of SARS-CoV-2 on host gene transcription. CBD induces interferon expression and up-regulates its antiviral signaling pathway. A cohort of human patients previously taking CBD had significantly lower SARS-CoV-2 infection incidence.

An extract fraction from *C. sativa* Arbel strain (designated as Full spectrum CBD=FCBD) substantially reduced (dose dependently) interleukin (IL)-6 and -8 levels in an alveolar epithelial (A549) cell line. FCBD contains cannabidiol (CBD), cannabigerol (CBG) and tetrahydrocannabivarin (THCV), and multiple terpenes. Treatments with FCBD and a FCBD formulation using phytocannabinoid standards (FCBD: std (with isolated CBD)) reduced IL-6, IL-8, C—C Motif Chemokine Ligands (CCLs) 2 and 7, and angiotensin I converting enzyme 2 (ACE2) expression in the A549 cell line. Treatment with FCBD induced macrophage (differentiated KG1 cell line) polarization and phagocytosis in vitro, and increased CD36 (a marker of human adipocyte progenitors stem cells, which is found in immune cells). and type II receptor for the Fc region of Immunoglobulin (Ig)G (FcγRII) expression. FCBD treatment also substantially increased IL-6 and IL-8 expression in macrophages. FCBD: std, while maintaining anti-inflammatory activity in alveolar epithelial cells, led to reduced phagocytosis and pro-inflammatory IL secretion in macrophages in comparison to FCBD. The phytocannabinoid formulation may show superior activity versus the *Cannabis*-derived fraction (isolated CBD) for reduction of lung inflammation. This study suggested that the "entourage effect" was more effective with a validated dose response curve, whereas pure CBD extract only allowed a narrow therapeutic range, with lower and higher dosing having less of an effect.

*Melaleuca cajuputi* essential oil (TA) extracted from fresh cajeput leaves through steam distilling. The inhibitory capability of active compounds in the TA over the Angiotensin-Converting Enzyme 2 (ACE2) protein in human body—the host receptor for SARS-CoV-2 and the main protease (PDB6LU7) of the SARS-CoV-2 using docking simulation has been studied. The results indicate that the ACE2 and PDB6LU7 proteins were strongly inhibited by 10 out of 24 compounds accounting for 70.9% in the TA. The most powerful anti-coronavirus activity is expressed in this order: Terpineol (TA2)≈Guaiol (TA5)≈Linalool (TA19)>Cineol (TA1)>β-Selinenol (TA3)>α-Eudesmol (TA4)>γ-Eudesmol (TA7). Interestingly, the synergistic interactions of these 10 substances of the TA exhibit excellent inhibition into the ACE2 and PDB6LU7 proteins.

This oil is similar in composition as the full spectrum CBG extract, and also suggests an entourage effect is present.

It is also hypothesized that COVID-19 patients are potentially vulnerable to a significant disease-drug interaction, and therefore, suitable dosing guidelines with therapeutic drug monitoring should be implemented to assure optimal clinical outcomes.

El-Ghiaty, Mahmoud A., Sherif M. Shoieb, and Ayman O S El-Kadi. "Cytochrome P450-mediated drug interactions in COVID-19 patients: Current findings and possible mechanisms." Medical hypotheses 144 (2020): 110033.

COVID-19 drugs, the patients may also be on therapeutics for comorbidities; especially epidemiological studies have indicated that individuals with hypertension, hyperglycemia, and obesity are more vulnerable to COVID-19 than the average population. This complicates the drug-disease interaction profile of the patients as both the investigational drugs (e.g., remdesivir (as a substrate for CYP2C8, CYP2D6, and CYP3A4 as well as an inhibitor of CYP3A4), dexamethasone, affecting CYP3A4, and 2B6 metabolism) and the agents for comorbidities can be affected by compromised CYP-mediated hepatic metabolism which affects the hepatic clearance of xenobiotics. Overall, it is imperative that healthcare professionals pay attention to the COVID-19 and CYP-driven drug metabolism interactions with the goal to adjust the dose or discontinue the affected drugs as appropriate.

CYP activity (usually in the liver but can also be present in other organs including kidneys, lung and brain) are modulated in an isoform-specific manner by SARS-CoV-2 infection.

There are less potential drug-drug interactions with a *Panakeia* extract to be concerned with for these considerations.

Phytocannabinoids

The term "phyto-cannabinoids" includes, but is not limited to, cannabinoids from *Cannabis* and N-alkylamides from *Echinacea*. The term "terpenes" includes, but is not limited to, pinene, limonene, α-terpinene, terpinen-4-ol, carvacrol, carvone, 1,8-cineole, p-cymene, fenchone, β-myrcene, cannaflavin A, cannaflavin B, nerolidol, phytol and squalene. The term "terpenoids" includes, but is not limited to, cannabinoids, limonene oxide, pulegone-1,2 epoxide, salviorin A, hyperforin, and pyrethrins. As used herein, the term "lipids" includes, but is not limited to, of olive oil, sesame oil, coconut oil, vegetable oil, milk, butter, liposomes, glycerin, polyethylene glycol, ethyl acetate, d-limonene, butylene glycol, propylene glycol, ethylhexyl palmitate. N-alkylamides includes, but is not limited to, dodeca-2E,4E,8Z,10Z-tetraenoic acid isobutylamide and dodeca-2E,4E-dienoic acid isobutylamide.

Cannabinoids from *Cannabis* are not the only lipid based exogenous compounds interacting with the endocannabinoid system. In the last few years, other plants have been found to produce cannabinoid-like compounds and several non-traditional cannabinoid plant natural products have been reported to act as cannabinoid receptor ligands. Consequently as "phyto-cannabinoid" is described any plant-derived natural product capable of either directly interacting with cannabinoid receptors or sharing chemical similarity with cannabinoids or both. (Gertsch et al., 2010).

Among phyto-cannabinoids different from traditional *Cannabis* cannabinoids, that have been reported to interact with the endocannabinoid system, unsaturated fatty acid N-alkylamides (N-alkylamides) from the medicinal plant *Echinacea*, a species of herbaceous perennial plant in the family Asteraceae, have been demonstrated to bind to the CB2 receptor more strongly than the endogenous cannabinoids (Raduner et al., 2006 and Woelkart et al., 2005). The interaction of N-alkylamides with the endocannabinoid system has been proven to modulate induced immune response. Other constituents from *Echinacea purpurea* act as weak CB1 antagonists (Hohmann et al., 2011).

Bitter acid humulone, a terpenoid contained in *Humulus lupulus* (hops) of the same Cannabinaceae family, is thought responsible for sedative effect. Humulone is subject to degradation in about 12 weeks at room temperature (Darby, 2015). Interestingly in 2017, Isodiol, a biotech company claimed it has extracted CBD from modified strains of hops.

Hyperforin is also a terpenoid produced by St. John's wort (*Hypericum perforatum*). Cannabinoids, bitter acids and hyperforin are polyketides with terpenoid building blocks and are lipophilic due to their terpenoid moiety (Osburn and Lanzotti, 2009).

Pyrethrins are terpenoids produced by *Chrysanthemum* genus plants. Pyrethrins can be found in *Cannabis* plant material and extracts as pyrethrins are used in the formulation of natural pesticides for *Cannabis* protection. Interestingly, in 2017, Devitt-Lee et al. reported the possibility that pyrethrins may be endogenously synthesized by *Cannabis*, hence they could become an additional component of *Cannabis* extractable phyto-complex.

Among plants producing cannabinoid-like compounds, Helichrysum umbraculigerum, a South-African species of perennial is also a major producer of CBG (Bohlmann et al., 1979). Other plants containing cannabinoids-like compounds are the Chinese *Rhododendron* and liverwort Radula Marginata in New Zealand (Toyota et al., 2002).

Herbolea Patented Process

Herbolea has provided a process useful for an enzyme assisted lipid-based extraction of lipophilic cannabinoids and/or terpenes/terpenoids from plant material, such as hemp, *Cannabis*, hops, *Echinacea, Salvia dinivorum, Chrysanthemum, Helichrysum* and *Hypericum* biomass.

Plant Species

The process may also be used on plant material derived from the Cannabinaceae genus of plants, that encompass the species *Cannabis* and *Humulus lupulus*, the *Echinacea* genus of plants, that encompass the species *E. purpurea, E. angustifolia, E. pallida*, the *Chrysanthemum* genus, that encompass the species *Tanacetum cinerariifolium* and *Chrysanthemum coccineum*, and/or *Salvia divinorium* and others.

Herbolea Biotech SRL has a patent-protected extraction system technology, see U.S. Pat. No. 10,973,864 and WO2021037343A1, utilizing a solvent-less (utilizing highly stable and standardized extracts with a longer shelf-life as compared to the use of highly flammable solvents during any production steps vs. $CO_2$ or ethanol extracts) method of obtaining cannabinoids from wet material to form a full spectrum lipid extract (oil tincture or full spectrum distillate) with over 90% efficiency. This process is federally compliant, offering full cannabinoid preservation with a more highly efficient terpene preservation (2.5× more compared to drying) technique. This one-step process that doesn't require drying, excessive energy use, costly solvents, nor skilled labor to operate, and delivers safer, 100% organic products that replicate *Cannabis* plant material's unique and delicate phyto-complexes. It uses a large batch (if scaled, using 100 kg of plant flower) process, taking 4 hours, to ensure consistency.

Stage 1 Herbolea Extraction Process Synopsis
 a. Thus, in an aspect, provided herein is a process for producing a lipid-soluble extract from plant material containing phytocannabinoids and terpenes/terpenoids, comprising the steps of (a) comminuting the plant material;
(b) mixing the comminuted plant material with enzymes to form a mixture to which water and lipids are optionally added;
(c) agitating the mixture at a temperature range of 1 to 80° C.; and
(d) separating the mixture into a lipid phase, an aqueous phase, and a solid phase; wherein the lipid phase comprises the lipid-soluble extract. See, U.S. Pat. No. 10,973,864 B2.

The process may be carried out by proceeding with steps a. and b. only, preserving the mixture resulting from step b. and proceeding with the addition of lipids and separation step d. subsequently, with or without agitation of the mixture.

The separation step d. can be carried out after one or more days, even in a different laboratory or facility. The lipids can be vegetable oils and/or glycerin and/or any other green (made from renewable sources) and/or food grade solvents.

Enzymes

The enzyme may be one or more enzymes independently selected from the group consisting of cellulase, beta-glucosidase, hemicellulase, xylanase, glucanase, β-glucanase, pectinase, amylase, alpha-amylase, phospholipase, beta-mannanase, arabinanase, phytase and protease. In an embodiment, the enzyme is cellulose. In another embodiment, the enzyme is beta-glucosidase. In another embodiment, the enzyme is hemicellulase. In another embodiment, the enzyme is xylanase. In yet another embodiment, the enzyme is glucanase. In yet another embodiment, the enzyme is pectinase. In still another embodiment, the enzyme is amylase. In yet another embodiment, the enzyme is phospholipase. In yet another embodiment, the enzyme is arabinanase. In still another embodiment, the enzyme is phytase. In a further embodiment, the enzyme is protease. The enzyme may be a mix or a cocktail of cellulase, β-glucanase, pectinase, β-mannanase, alpha-amylase and protease; wherein the amount of enzyme is 3% of the weight of plant material; and the pH of the mixture is adjusted to pH 5.6 with monohydrate citric acid. The amount of enzyme is in the range of from 0.2%, 0.5% to 10% of the weight of plant material. The pH of the mixture may be 3-10.

Solubilized Carrier Oil

The lipid may be one or more lipids independently selected from the group consisting of olive oil, sunflower, oil, coconut oil, sesame oil, vegetable oil, milk, butter, liposomes and hemp seed oil, black seed oil, and/or other green and/or food grade solvents such as glycerin, polyethylene glycol, ethyl acetate, d-limonene, butylene glycol, propylene glycol, ethylhexyl palmitate and/or with the addition of lecithin. In an embodiment, the lipid is olive oil. In another embodiment, the lipid is coconut oil. In another embodiment, the lipid is sesame oil. In another embodiment, the lipid is vegetable oil. In yet another embodiment, the lipid is milk. In a further embodiment, the lipid is butter. In a further embodiment, the lipid is black seed oil.

Black seed oil, derived from the Nigella *sativa* plant, contains 15 amino acids, including essential amino acids (histidine, isoleucine, leucine, lysine, methionine, phenylalanine, threonine, and tryptophan), as well as arginine (improve circulation, immunity and metabolism); Thymoquinone (TQ), Thymol (both antifunal effects) and, Thymohydroquinone (THQ, potent natural acetylcholinesterase (AChE) inhibitors, which can improve cognition). It has a wide array of benefits for both internal and external use. The primary uses of black seed oil include reducing inflammation, fighting bacteria and damaging free radicals, supporting optimal immune system, lessen allergic reactions, respiratory conditions (including asthma, cough, bronchitis, emphysema, flu or other viral upper respiratory infections and congestion), gut (including gas, colic, diarrhea, dysentery, constipation, and hemorrhoids) and liver function and healing, regulating blood sugar (with partial regeneration of pancreatic beta-cells), lowering lipid levels, and lowering blood pressure, and speeding the healing process for wounds and skin conditions, and possibly anti-cancer effects.

Hemp seed oil or whole seeds that are expressed or extracted from seeds contain 0% THC and trace levels of CBD, but 0% CBD if derived from *Panakeia* (may contain a small amount of CBGA or CBG). It has a high content of three polyunsaturated fatty acid esters: linoleic acid, alpha-linolenic acid, and gamma-linolenic acid, which can improve the lipid profile to reduce cardiovascular and cerebrovascular disease, and can help lower blood pressure Additionally, its ratio of omega-6 (linoleic acid) to omega-3 (alpha-linolenic acid) fatty acids is 3:1, which a favorable ratio in humans. Gamma-linoleic acid (GLA) present in hemp seed oil has been shown to reduce inflammation such as irritable bowel syndrome (IBS), rheumatoid arthritis (RA), and multiple sclerosis (MS). It may reduce symptoms of menstrual cramps and improve recovery of muscles after exercise. If taken while pregnant, it supports healthy fetal brain and eye development and may also help prevent maternal depression. If applied topically, it improves symptoms of atopic dermatitis, also known as eczema and may be useful for cradle cap, psoriasis, and acne. *Panakeia* (hemp) seed oil will contain 0% THC, 0% CBD with trace CBGA. It is anticipated that hemp seed oil with enhance absorption of the *Panakeia* extract.

One tablespoon (15 milliliters) of hemp seed oil contains: Calories: 125; Total fat: 14 grams; Saturated fatty acids: 1 gram; Monounsaturated fatty acids: 2 grams; Polyunsaturated fatty acids: 11 grams (75-80%). Protein: 7 grams (15%, of which approximately 65% of the protein in hemp seeds is made up of the globulin protein Edestin and is found only in hemp seed. Edestin aids digestion, is relatively phosphorus-free and considered the backbone of the cell's DNA. The other one third of hemp seed protein is Albumin, another high quality globulin protein similar to that found in egg whites; contains all of the essential amino acids with high levels arginine). Rich antioxidants especially Vitamin E, also carotene (precursor to Vitamin A), phytosterols, phospholipids and a number of minerals including calcium, magnesium, sulfur, potassium, phosphorus, along with modest amounts of iron and zinc; denatured by heating above 150° C.

Sunflower oil is pressed from the seeds of the sunflower. In foods, sunflower oil is used as a cooking oil. Sunflower oil is also used as medicine. Sunflower oil is most commonly used for constipation and lowering "bad" LDL cholesterol and preventing heart disease. Sunflower oil may be applied directly to the skin for poorly healing wounds, skin injuries, psoriasis, and arthritis; and as a massage oil. Some critics suggest it could be trigger arthritis flare-ups due to its omega-6 fatty acids content. However, there has been a traditional use of sunflower (*Helianthus annuus*) preparations for anti-inflammatory and analgesic applications. Kappa opioid receptor ligands (termed as helianorphins) derived from a cyclic sunflower peptide scaffold, which can be found in seeds, has recently been used for the treatment of chronic visceral abdominal pain in mice.

Muratspahić, Edin, Nataša Tomašević, Johannes Koehbach, Leopold Duerrauer, Seid Hadžić, Joel Castro, Gudrun Schober et al. "Design of a Stable Cyclic Peptide Analgesic Derived from Sunflower Seeds that Targets the κ-Opioid Receptor for the Treatment of Chronic Abdominal Pain." Journal of medicinal chemistry 64, no. 13 (2021): 9042-9055.

Clove (*Syzygium aromaticum*) oil which primarily contains eugenol is colorless to light yellow and has a strong, spicy aroma. It is produced by distilling the dried flower buds that are collected from the clove tree. Other parts of the tree, such as the stem and leaves, may also be used as an antimicrobial, especially for yeast (*Candida albicans*) to treat athlete's foot, oral thrush, and vaginal yeast infections. It also helps kill bacteria, with antimicrobial properties and use it as a mild spray disinfectant. It may be used as a pain reliever for conditions such as toothache (preventing dental erosion to prevent cavities and relieve oral pain) and muscle pain as a topical anesthetic, used for digestive upset and has been used to relieve respiratory conditions like cough (as an expectorant and helps in expelling mucus from the respiratory passage and reduces inflammation) and asthma. Eugenol treatment reduced LPS-induced lung inflammation, improving lung function. Our results suggest that eugenol exhibits in vivo anti-inflammatory action in LPS-induced lung injury. Topically, it may be used for chronic itching and anal fissures. Clove oil in vitro seems to be effective at killing cancer cells or stopping them from growing. Clove oil can cause skin irritation or allergic reactions in some people. It is suggested to be avoided with anticoagulants, monoamine oxidase inhibitors (MAOIs), selective serotonin reuptake inhibitors (SSRIs). Specific health conditions to avoid using clove oil include recent major surgery, peptic ulcers, bleeding disorder, such as hemophilia. www.healthline.com/health/clove-essential-oil.

In 2020, it was demonstrated that clove essential oil, and the major compound of the essential oil, eugenol, improved diabetes-induced erectile dysfunction in rats, and clove oil caused corpus cavernosus relaxation via K+ channels independently NO signaling pathway, from phosphodiesterase inhibition, which may be useful in diabetic men with erectile dysfunction.

Yilmaz-Oral, D., Onder, A., Gur, S., Carbonell-Barrachina, Á. A., Kaya-Sezginer, E., Oztekin, C. V., & Zor, M. (2020). The beneficial effect of clove essential oil and its major component, eugenol, on erectile function in diabetic rats. Andrologia. doi:10.1111/and.13606

The essential clove oil inhibited α-amylase (EC50=88.9 ml/L) and α-glucosidase (EC50=71.94 ml/L) activities in a dose-dependent manner. The total phenolic and flavonoid contents of the essential clove oil were 12.95 mg/g and 6.62 mg/g respectively, with the presence of α-pinene, β-pinene, neral, geranial, gamma terpinene, cis-ocimene, allo ocimene, 1,8-cineole, linalool, borneol, myrcene and pinene-2-ol in significant amounts. Furthermore, the essential oils exhibited antioxidant activities as typified by hydroxyl (OH) and nitric oxide (NO)] radicals scavenging and $Fe^{2+}$-chelating abilities. The inhibition of α-amylase and α-glucosidase activities, inhibition of pro-oxidant induced lipid peroxidation in rat pancreas and antioxidant activities could be possible mechanisms for the use of the essential oil in the management and prevention of oxidative stress induced type-2 diabetes.

Oboh, Ganiyu, Ifeoluwa A. Akinbola, Ayokunle O. Ademosun, David M. Sanni, Oluwatoyin V. Odubanjo, Tosin A. Olasehinde, and Sunday I. Oyeleye. "Essential oil from clove bud (*Eugenia aromatica* Kuntze) inhibit key enzymes relevant to the management of type-2 diabetes and some pro-oxidant induced lipid peroxidation in rats pancreas in vitro." Journal of oleo science (2015): ess14274.

Treatment with clove (*Syzygium aromaticum*) flower bud causes dose dependent biphasic effect on male reproductive indices in P mice; lower dose of *Syzygium* appears stimulatory and may have androgenic effects Mishra, Raghav Kumar, and Shio Kumar Singh. "Reproductive effects of lipid soluble components of *Syzygium aromaticum* flower bud in male mice." Journal of Ayurveda and integrative medicine 4, no. 2 (2013): 94.

Eugenol, a methoxyphenol component of clove oil, suppresses cyclooxygenase-2 expression, while eugenol dimers prevent nuclear factor-B (NF-B) activation and inflammatory cytokine expression in lipopolysaccharide-stimulated (LPS) macrophages. Eugenol treatment reduced LPS-induced lung inflammation, improving lung function. Our results suggest that eugenol exhibits in vivo anti-inflammatory action in LPS-induced lung injury. Magalhães, Clarissa B., Douglas R. Riva, Leonardo J. DePaula, Aline Brando-Lima, Vera Lúcia G. Koatz, José Henrique Leal-Cardoso, Walter A. Zin, and Débora S. Faffe. "In vivo anti-inflammatory action of eugenol on lipopolysaccharide-induced lung injury." Journal of Applied Physiology 108, no. 4 (2010): 845-851.

Phosphodiesterases are a class of 11 isoenzymes that are able to cleave the phosphodiester bond in either cyclic adenosine monophosphate (cAMP) or cyclic guanosine monophosphate (cGMP) to yield 50-cyclic nucleotides. Thus they are responsible for controlling cellular concentration of cAMP and cGMP by hydrolyzing them to 50-AMP and 50-GMP influencing many physiological functions such as cardiac contractility, smooth muscle relaxation, platelet aggregation, visual response, fluid homeostasis, and immune responses.

PDE1 isozymes are present in the central nervous system, heart, kidney, lung, and smooth muscle. PDE1 inhibitors are possible therapeutic targets in dementia and memory loss. PDE2 is expressed in adrenal gland, heart, lung, liver, and platelets. Disease targets for PDE2 inhibitors are sepsis and acute respiratory distress syndrome, which may include COVID-19. PDE3 has higher affinity for cAMP than cGMP. It is mainly expressed in the vasculature, the airways, liver, platelets, adipose tissue, and inflammatory cells. PDE3 inhibitors have been identified as a potential therapeutic target in cardiovascular disease and asthma and inhibit platelet aggregation and induce lipolysis. PDE4, a cAMP PDE, is the predominant isoenzyme in the majority of inflammatory cells. It is expressed in the airways smooth muscle, brain, cardiovascular tissues, and kidney so its disease targets are allergic rhinitis, psoriasis, multiple sclerosis, depression, Alzheimer's disease, schizophrenia, memory loss, cancer, and dermatitis. PDE5, a cGMP-specific PDE, is expressed in lung, platelets, and vascular smooth muscle. PDE5 inhibitors are able to induce vascular smooth muscle relaxation. Therefore, PDE5 inhibitors are possible therapeutic targets in cardiovascular disease, pulmonary hypertension, female sexual dysfunction, premature ejaculation, stroke, leukemia, and renal failure. PDE6 is highly concentrated in the retina. It is most abundant in the internal membranes of retinal photoreceptors, where it reduces cytoplasmic levels of cGMP in rod and cone outer segments in response to light having an essential role in visual function. Since the catalytic sites of PDE5 and PDE6 is similar with respect to drug binding, most PDE5 inhibitors inhibit PDE6 with similar potency and thus cause visual disturbances. PDE7 is a cAMP-specific PDE expressed widely in immune and pro-inflammatory cells. Drugs inhibiting PDE7 have potential to be proposed as novel anti-inflammatory drugs. PDE8 is a family of cAMP-specific enzymes and plays important roles in many biological processes, including T-cell activation, testosterone production, adrenocortical hyperplasia, and thyroid function. PDE9 is highly specific for cGMP and its high expression has been detected in various tissues, including brain, kidney, spleen, prostate, colon, and intestine and may be applied for treatment of Alzheimer's disease. PDE10 shows a dual activity on hydrolysis of both cAMP and cGMP and is highly expressed in brain striatum. The PDE10 inhibitor, papaverine, is effective in improving executive function deficits associated with schizophrenia, and therefore inhibition of PDE10 may represent an approach to treatment of psychosis. PDE11A is a dual-substrate PDE, acting on both cAMP and cGMP. There is evidence for PDE11 expression in skeletal muscle, prostate, testis and salivary glands. The function of PDE11 remains largely unknown, but growing evidence points to a possible role in male reproduction.

Phosphodiesterase inhibitors (PDEIs) are a class of drugs such as caffeine, theophylline and sildenafil that are widely used because of their various pharmacological properties including cardiotonic, vasodilator, smooth muscle relaxant, antidepressant, antithrombotic, bronchodilator, anti-inflammatory and enhancer of cognitive function and can be used as therapeutic agents for various diseases such as dementia, depression, schizophrenia, congestive heart failure, asthma, chronic obstructive pulmonary disease, diabetes, rheumatoid arthritis, multiple sclerosis, Crohn's disease, erectile dysfunction in men, and persistent pulmonary hypertension of the newborn. Some pharmacologically active substances that come from plants demonstrate PDEI activity. They mainly belong to alkaloids, flavonoids, and saponins.

Rahimi, R., Ghiasi, S., Azimi, H., Fakhari, S., & Abdollahi, M. (2010). A review of the herbal phosphodiesterase inhibitors; Future perspective of new drugs. Cytokine, 49(2), 123-129. doi:10.1016/j.cyto.2009.11.005

Essential oils, as their name implies, are volatile in steam. They differ entirely in both chemical and physical properties from fixed oils. They are secreted in oil cells, in secretion ducts or cavities or in glandular hairs. They are found in plants belonged to different families. Different pharmacological properties have been reported from essential oils mainly antimicrobial, carminative, and antispasmodic activities Lavender does play an important role in aromatherapy and herbal medicine, commonly used in fragrances and shampoos to help purify the skin, but there are other ways to use it. Its essential oils may have some health benefits including. antiseptic and anti-inflammatory properties, which can help to heal minor burns and bug bites. A 2017 laboratory found that topical lavender oil exhibited antibacterial properties in human cells, and in another study it was effective in combating antifungal-resistant infections by destroying the membranes of fungal cells. The oil killed or reduced the strength of several potentially dangerous species, including *Escherichia coli* and *Staphylococcus aureus*. The medicinal benefits of using lavender are suggestive that Silexan (a lavender-oil preparation available in 80-milligram gelatin capsules) had anxiolytic effects, within 2 weeks. Research from 1998, has shown that topical lavender can promote hair growth by up to 44 percent after 7 months of treatment for alopecia areata. In a more recent study, researchers found that applying lavender oil to the backs of mice helped to promote hair growth over the course of 4 weeks. Aromatherapy with *Lavandula angustifolia* essential oil might reduce symptoms of pain in children after the removal of the tonsils, alleviate premenstrual emotional symptoms and to treat anxiety for its calming effect, prior to dental appointments. Other studies support its use in insomnia, depression, and restlessness, and wounds, with possible evidence to improve high blood pressure, gastrointestinal symptoms (lavender tea can help digestive issues such as vomiting, nausea, intestinal gas, upset stomach, and abdominal swelling), menstrual pain, eczema, headaches, sprains, toothaches, and sores, among other conditions. It is important always to dilute essential oils in a carrier oil, such as almond or jojoba oil. Lavender essential oil, in contrast to the plant form, is toxic when swallowed. There are possible topical allergic reactions, and a study published in the New England Journal of Medicine (NEJM) revealed that repeated use of lavender oil on the skin might trigger prepubertal gynecomastia, a condition that causes enlarged breast tissue in boys before puberty. The safety of taking lavender during pregnancy or while breast-feeding has also not been confirmed.

What are the health benefits and risks of lavender?www-.medicalnewstoday.com/articles/265922 #benefits An aqueous extract of *Cordyceps sinensis*, an edible mushroom growing in Himalayan regions may be considered for promoting tolerance to high altitudes. It has been demonstrated to have a protective effect of hypoxia-induced oxidative stress in lung epithelium cells by attenuating hypoxia induced reactive oxygen species (ROS) generation, oxidation of lipids (by inhibited the hypoxia-induced lipid peroxidation), and proteins (by inhibited the formation of protein carbonyls levels) and maintained antioxidant status (increased reduced glutathione-GSH levels) via induction of antioxidant gene HO1 (heme oxygenase-1), MT (metallothionein), and Nrf2 (nuclear factor erythroid-derived 2-like 2) by maintaining higher cellular Nrf2, hypoxia inducible factor-1 (HIF1) and lowering nuclear factor kappa B (NFκB) levels. NFκB activates genes particularly involved in the inflammatory response, as well as in modulating the cellular response to oxidative injury, and plays an important role in the innate and adaptive immunity and cellular survival through the induction of genetic networks. At the same time decrease in NFκB levels resulted in lower expression of proinflammatory cytokines like tumor necrosis factor-α (TNFα) and increased expression of anti-inflammatory cytokine transforming growth factor beta (TGFβ). The high amount of phenols, flavonoids, nucleosides (adenosine), nucleobases (adenine and uracil), and polysaccharides found in *Cordyceps sinensis* absorb and neutralize free radicals, quench singlet and triplet oxygen, or decompose peroxides.

This fungus appears to also lower blood glucose and plasma insulin, and improves glucose metabolism by enhancing insulin sensitivity. *Cordyceps sinensis* has previously been investigated in animal and in vitro studies for antiaging effects, activity on sexual function, and immune modulation, among other potential uses. In a prior clinical study of elderly patients with chronic fatigue, results indicated that most of the subjects treated with *Cordyceps sinensis* pure mycelium reported a significant clinical improvement in the areas of fatigue, cold intolerance, dizziness, frequent nocturia, tinnitus, hyposexuality, and amnesia.

Singh, Mrinalini, Rajkumar Tulsawani, Praveen Koganti, Amitabh Chauhan, Manimaran Manickam, and Kshipra Misra. "*Cordyceps sinensis* increases hypoxia tolerance by inducing heme oxygenase-1 and metallothionein via Nrf2 activation in human lung epithelial cells." BioMed Research International 2013 (2013).

Boiling Points of Phytochemicals
  Boiling points, which can affect extraction specifications:
Cannabinoids:
  CBGA 180° C.
  CBG 105° C.
  THC-9 157° C.
  CBN 185° C. (THC-9 degradation product)
  CBD 160-180° C. (may be synthesized to THC-8 175-178° C.)
  CBDA 120-130° C.
  CBN 185° C.
  CBC 220° C.
  THCV<220° C.
Terpenes:
  β-myrcene 136.23 168° C.
  β-caryophyllene 204.35 160° C.
  alpha-humulene 106° C. trans-245.3° C.
  d-Limonene 136.23 176° C.
  Linalool 154.25 198° C.
  pulegone 152.23
  1,8-cineole 154.25
  α-pinene 136.23 155° C.
  α-terpineol 154.25
  erpineol-4-ol 154.25
  p-cymene 134.22
  eucolyptal 176
  Butylated hydroxytoluene 265° C.
Flavonoids:
  apigenin 270.24
  quercetin 302.23
  cannaflavin A No data
  β-sitosterol 414.71
  (Data from: comptox.epa.gov/dashboard).
  Different variables such as run time or pressure can be adjusted to compensate for products that are heat sensitive.

REFERENCES

Each reference cited or mentioned herein is expressly incorporated herein by reference in its entirety.

See, WO2020252396A1; WO2020171713A1; WO2021047491A1; CN110878010A; RU2073670C1; FI95369C; FI95369B; WO2021141955A1; WO/2020/249184; US20190262304A1; KR0183396B1; U.S. Ser. No. 11/026,915B2; EP0445781A1; WO2016118540A1; EP0445781B1; US20160206610A1; IL97426A; U.S. Pat. Nos. 5,013,837A; 4,973,587A; CA2036307C; KR100191258B1; AU643757B2; HU211967A9; IL110447A; CA2035711A1; EP0444451A2; IE72953B1; U.S. Pat. No. 5,068,234A; JP3157179B2; IL97313A; U.S. Pat. Nos. 5,607,933A; 5,817,651A; AU638795B2; CA3089490A1; HU208132B; U.S. Ser. No. 11/034,639B2; IE910700A1; EP3746419A1; WO2019145552A1; HU215125B; US20190201809A1; AU2019211188A1; ES2801005T3; EP3247371B1; IE910492A1; EP3556376A1; AU2016210070A1; RU2052457C1; U.S. Pat. No. 9,765,000B2; CA2977421A1; AU2021203749A1; US20160214920A1; BR112017015536A2; U.S. Ser. No. 10/155,708B2; WO2016116628A1; US20180000879A1; EP3247371A1; U.S. Ser. No. 10/207,199B2; U.S. Ser. No. 10/864,458B2; U.S. Ser. No. 10/207,198B2; US20180162828A1; US20180222879A1; PT96871B; US20190134532A1; US20210112743A1; US20200405685A1; U.S. Ser. No. 10/117,891B2; US20170027978A1; U.S. Pat. No. 6,949,582B1; US20190030062A1; U.S. Ser. No. 10/933,082B2; US20070032544A1; US20180042975A1; US20200390711A1; US20210236575A1; US20200084989A1; US20200299216A1; US20130059018A1; US20100292345A1; USPP32725P2; US20200246406A1; US20050266108A1; US20080031977A1; US20180222879A1; US20140039043A1; US20100168448A1; US20150265720A1; US20190201809A1; US20180243259A1; US20210196670A1; US20180221304A1; U.S. Ser. No. 10/207,199B2; U.S. Ser. No. 10/207,198B2; U.S. Ser. No. 10/596,159B2; US20200372993A1; US20180162828A1; U.S. Ser. No. 10/555,906B2; US20190270691A1; US20210100862A1; U.S. Ser. No. 11/034,639B2; US20200345686A1; US20200181631A1; US20210205236A1; US20200261406A1; US20200071285A1; US20210196774A1; US20180228788A1; US20200222359A1; US20140107192A1; US20200030282A1; US20210121794A1; US20190307719A1; USPP31917P3; US20180193403A1; US20190167749A1; US20190382326A1; US20100249223A1; US20190382325A1; US20140378539A9; US20150126754A1; U.S. Pat. No. 9,895,342B2; US20180344661A1; USPP31752P3; USPP31707P3; US20190276420A1; USPP31918P3; USPP31874P3; US20200121606A1; USPP31724P3; U.S. Pat. No. 9,044,390B1; U.S. Ser. No. 10/709,748B2; USPP32473P3; US20210186870A1; US20200338151A1; US20190216870A1; U.S. Pat. No. 7,807,711B2; U.S. Pat. No. 9,532,593B2; US20150297653A1; U.S. Pat. No. 9,980,996B2; US20200261407A1; U.S. Pat. No. 6,403,126B1; US20180263952A1; US20190307825A1; US20200383371A1; US20200399194A1; U.S. Ser. No. 10/604,464B2; US20190022158A1; U.S. Ser. No. 10/064,905B1; US20180078504A1; US20210204503A1; U.S. Ser. No. 11/078,145B2; US20190010107A1; US20190194585A1; US20210236955A1; US20190314327A1; US20200025728A1; US20110021617A1; US20150181925A1; US20190307826A1; US20200398184A1; US20190085347A1; US20200188323A1; US20190254326A1; US20170172201A1; U.S. Ser. No. 10/675,264B2; US20190374552A1; US20200179269A1; US20070077660A1; US20210128518A1; US20200286597A1; US20210068444A1; US20200170950A1; US20180369192A1; US20200222361A1; US20190216869A1; US20200255389A1; U.S. Ser. No. 10/709,747B2; US20180360894A1; US20200338150A1; U.S. Ser. No. 10/052,339B2; U.S. Pat. No. 9,955,716B1; US20200163931A1; US20190307720A1; US20210003488A1; US20190153460A1; US20200316015A1; US20180193399A1; US20210236459A1; US20200170944A1; U.S. Ser. No. 10/588,974B2; US20210038513A1; US20210177013A1; US20210045434A1; US20190338301A1; US20210059975A1; US20100239693A1; US20190134123A1; US20170333505A1; U.S. Ser. No. 10/973,255B2; US20190161763A1; US20180193304A1; US20210068450A1; US20210128450A1; US20200121637A1; US20170189373A1; US20170361525A1; US20140377382A1; US20210212981A1; U.S. Ser. No. 10/117,883B2; US20170319607A1; U.S. Ser. No. 10/722,490B2; U.S. Ser. No. 10/378,020B2; US20150265636A1; US20190010110A1; U.S. Pat. No. 9,833,408B1; US20190153461A1; US20150057342A1; US20190133966A1; U.S. Ser. No. 10/843,991B2;

US20190374502A1; US20190390408A1; US20190192993A1; US20180344684A1; US20200108082A1; US20200254041A1; US20180344663A1; U.S. Pat. No. 8,846,409B2; US20150265637A1; US20200108045A1; US20190183010P1; US20210251946A1; US20210220272A1; US20200190002A1; US20200281890A1; U.S. Ser. No. 10/821,147B2; US20200138737A1; US20180360896A1; US20200289459A1; USPP33332P3; US20190030101A1; US20210177800A1; US20210039013A1; U.S. Pat. No. 9,827,281B2; US20190269865A1; US20200352216A1; US20160161459A1; US20160360721A1; US20190076349A1; US20180042845A1; US20200197521A1; US20180344860A1; US20190224142A1; US20210219597A1; US20210238561A1; US20190134125A1; US20200282062A1; US20210251948A1; U.S. Ser. No. 10/743,568B2; US20180064772A1; US20190183004P1; US20140271940A1; US20210093561A1; US20200276324A1; US20200215136A1; US20190117778A1; US20200330378A1; US20200048215A1; US20210137833A1; U.S. Ser. No. US20180064645A1; U.S. Ser. No. 10/456,357B2; 10/392,635B2; U.S. Ser. No. 10/369,178B2; US20210212946A1; US20210052545A1; US20200022925A1; U.S. Ser. No. 11/027,218B2; US20170157343A1; US20190261657A1; US20140343136A1; US20210244653A1; US20200101034A1; U.S. Ser. No. 10/118,006B2; US20200017889A1; US20210038560A1; US20200246404A1; US20210069170A1; US20210092972A1; U.S. Pat. No. 9,827,282B2; US20200078332A1; US20180071210A1; US20170021025A1; U.S. Ser. No. 10/675,314B2; US20210145851A1; U.S. Ser. No. 10/729,706B2; US20170143664A1; US20190275268A1; US20170127727A1; US20190167583A1; US20180344786A1; US20170312261A1; US20200297948A1; US20190350949A1; US20170020942A1; US20180078593A1; US20190328884A1; US20190240191A1; US20170021026A1; US20090035396A1; U.S. Ser. No. US20180360757A1; US20190059960A1; 10/576,157B2; US20180352848A1; US20210038666A1; US20210093552A1; US20200037638A1; U.S. Pat. No. US20200038421A1; U.S. Ser. No. 10/596,211B2; 9,839,241B2; US20190366231A1; US20150231108A1; US20200022945A1; US20140287068A1; U.S. Ser. No. US20190365667A1; US20180043115A1; 10/822,320B2; U.S. Ser. No. 10/653,787B2; US20210059949A1; US20190060220A1; US20200330537A1; U.S. Pat. No. 9,822,384B2; US20170056368A1; U.S. Ser. No. 10/617,834B2; US20210220324A1; US20210137877A1; U.S. Ser. No. US20160151328A1; US20190000795A1; 10/172,897B2; U.S. Ser. No. 10/258,580B2; US20200138072A1; US20190151771A1; US20170202170A1; US20200222543A1; US20200078333A1; U.S. Ser. No. 11/084,770B2; US20210220323A1; US20200115306A1; U.S. Pat. No. US20150086653A1; US20190060252A1; 9,585,867B2; U.S. Ser. No. 10/669,248B2; U.S. Ser. No. US20190307695A1; US20190029993A1; 10/688,190B2; US20180021438A1; US20180125980A1; US20190030044A1; U.S. Pat. No. 8,790,719B2; U.S. Ser. U.S. Pat. No. 9,421,187B2; U.S. Ser. No. 10/993,977B2; No. 10/272,051B2; U.S. Pat. No. 9,675,654B2; US20200290988A1; U.S. Ser. No. 10/918,686B2; U.S. Ser. US20190060251A1; U.S. Pat. No. 9,815,810B1; No. 10/954,534B2; US20200230185A1; U.S. Ser. No. US20190134532A1; U.S. Ser. No. 10/239,808B1; 10/189,762B1; US20200323936A1; US20190183914A1; US20190231737A1; US20180199531A1; U.S. Pat. No. USPP33162P3; U.S. Ser. No. 10/093,949B2; 7,700,368B2; US20200016095A1; US20160214920A1; US20200039908A1; US20190321330A1; U.S. Ser. No. US20210106637A1; U.S. Pat. No. 8,481,085B2; U.S. Ser. 10/799,546B1; US20210106929A1; U.S. Ser. No. 10/842, No. 10/441,552B2; US20150203434A1; 786B2; U.S. Pat. No. 9,642,317B2; U.S. Ser. No. 11/040, US20100222437A1; US20160184259A1; U.S. Ser. No. 017B2; U.S. Pat. No. 9,035,130B2; U.S. Ser. No. 10/582, 10/864,458B2; US20190060250A1; US20200188325A1; 676B2; US20200048214A1; US20210093652A1; US20210023045A1; US20200108046A1; U.S. Pat. No. US20170020941A1; U.S. Ser. No. 10/676,453B1; 9,765,000B2; US20210212961A1; US20200253919A1; US20170368021A1; U.S. Ser. No. 10/064,950B2; U.S. Ser. U.S. Ser. No. 10/946,054B1; US20180000879A1; No. 10/842,773B2; U.S. Pat. No. 9,370,164B2; U.S. Ser. US20190254213P1; U.S. Ser. No. 10/155,708B2; No. 10/792,318B2; U.S. Ser. No. 10/406,186B2; US20160235661A1; US20180110753A1; U.S. Ser. No. US20200054701A1; US20190033210A1; 10/959,978B2; USPP33000P3; US20200068919A1; US20200368639A1; U.S. Ser. No. 10/098,867B2; U.S. Ser. USPP27475P2; US20190008823A1; U.S. Ser. No. 10/206, No. 10/502,750B2; US20180143212A1; 888B2; US20200261404A1; US20190183007P1; U.S. Ser. US20200191480A1; US20150359188A1; No. 10/857,107B2; US20160374958A1; US20200367548A1; US20180074045A1; US20200330339A1; US20190183003P1; U.S. Ser. No. US20200094003A1; US20180064055A1; 11/058,646B2; USPP31535P3; U.S. Ser. No. 10/543,190B2; US20190183853A1; U.S. Ser. No. 10/806,707B2; US20180221333A1; U.S. Pat. No. 9,844,530B1; US20170266153A1; US20200071732A1; U.S. Pat. No. US20210154252A1; US20190183006P1; 9,095,554B2; US20140221469A1; US20210030824A1; US20160166498A1; US20210128522A1; U.S. Pat. No. US20190030103A1; US20160010126A1; 9,814,695B2; US20190111093A1; US20210236687A1; US20210023156A1; U.S. Ser. No. 10/940,173B2; U.S. Ser. US20160136128A1; US20190321306A1; U.S. Ser. No. No. 10/441,617B2; U.S. Pat. No. 9,827,322B2; U.S. Ser. 10/092,538B2; U.S. Ser. No. 11/000,486B2; No. 10/905,730B2; US20200376156A1; US20190183008P1; US20190209487A1; US20210000791A1; U.S. Ser. No. 10/702,565B2; US20160220593A1; US20160345477P1; U.S. Ser. No. US20210069271A1; US20200170283A1; 10/172,786B2; US20210059978A1; US20190175523A1; US20160324091A1; US20210136974P1; US20190183005P1; US20190069675A1; US20170112801A1; US20190177294A1; US20200179426A1; US20180344790A1; US20200138736A1; U.S. Ser. No. 10/458,908B2; US20200196504P1; US20210100746A1; US20190328807A1; U.S. Ser. No. 11/040,932B2; US20110098348A1; US20190183009P1; US20200000766A1; US20150342922A1;

US20200390721A1; US20200222828A1; US20160309774A1; U.S. Ser. No. 10/231,948B2; U.S. Ser. No. 10/568,865B2; U.S. Ser. No. 10/849,876B2; U.S. Ser. No. 10/624,872B1; US20140298511A1; US20170340562A9; US20180073043A1; US20190125779A1; U.S. Ser. No. 10/897,915B2; US20180371507A1; US20200215137A1; US20140228438A1; US20150366154A1; U.S. Ser. No. 10/639,339B2; US20190142888A1; U.S. Ser. No. 10/835,839B1; U.S. Ser. No. 11/091,455B2; U.S. Ser. No. 10/709,670B2; US20180147141A1; US20200085959A1; US20160346339A1; US20180214790A1; US20210038493A1; US20180264059A1; US20190125660A1; U.S. Ser. No. 10/596,147B1; U.S. Ser. No. 10/780,075B1; U.S. Ser. No. 10/745,644B1; US20180110730A1; U.S. Ser. No. 10/668,044B2; US20190010106A1; US20190230882A1; US20180339973A1; US20210106556A1; US20210106635A1; US20210197156A1; US20190232194A1; U.S. Ser. No. 10/507,404B2; US20180369191A1; U.S. Ser. No. 10/092,611B1; US20210085638A1; U.S. Ser. No. 11/026,881B2; US20190015346A1; US20200046836A1; US20180133272A1; U.S. Ser. No. 10/792,584B1; US20170339907A1; U.S. Ser. No. 11/000,818B1; US20200246405A1; US20180297726A1; U.S. Ser. No. 10/894,780B1; US20210046111A1; US20200405686A1; U.S. Ser. No. 10/737,198B2; US20200254104A1; U.S. Ser. No. 10/525,093B2; U.S. Ser. No. 10/238,705B2; US20210228536A1; US20190038995A1; US20160074451A1; US20180338930A1; U.S. Ser. No. 10/420,809B2; US20200360337A1; U.S. Ser. No. 10/588,979B1; US20190091144A1; U.S. Ser. No. 10/849,852B2; U.S. Ser. No. 10/765,965B1; U.S. Ser. No. 10/246,431B2; U.S. Pat. No. 9,675,656B2; U.S. Ser. No. 10/912,807B1; US20200206126A1; U.S. Ser. No. 10/830,780B2; US20210015836A1; US20180147247A1; U.S. Ser. No. 10/624,940B2; US20200165219A1; US20180161285A1; US20210230645A1; US20160324776A1; U.S. Pat. No. 9,956,498B1; US20210100755A1; US20170274030A1; US20200038366A1; US20170348277A1; U.S. Pat. No. 9,730,911B2; U.S. Pat. No. 9,802,880B2; US20200383935A1; U.S. Ser. No. 10/296,714B2; US20200339528A1; US20200060305A1; US20170119728A1; US20190321426A1; US20200316016A1; U.S. Ser. No. 10/059,684B2; US20150374770A1; U.S. Pat. No. 9,649,349B1; US20200398183A1; US20200197359A1; US20160106705A1; US20160000843A1; US20160326130A1; U.S. Ser. No. 10/864,189B2; US20190209633A1; U.S. Pat. No. 9,744,200B1; U.S. Ser. No. 10/092,852B2; US20150297654A1; US20170360745A1; U.S. Ser. No. 10/499,584B2; U.S. Pat. No. 9,937,147B2; US20200297690A1; US20200000765A1; US20210106533A1; US20180284145A1; US20210245073A1; US20210106532A1; U.S. Ser. No. 10/751,300B2; US20100204312A1; U.S. Pat. No. 9,084,771B2; US20180021247A1; US20200179342A1; US20200288659A1; U.S. Ser. No. 10/555,928B2; US20210251949A1; U.S. Pat. No. 9,186,386B2; US20200147034A1; U.S. Pat. No. 9,962,341B2; US20210078967A1; US20120004251A1; U.S. Ser. No. 11/026,915B2; U.S. Pat. No. 9,956,173B1; U.S. Ser. No. 10/799,467B2; US20200068899A1; U.S. Pat. No. 9,526,792B1; US20190134121A1; US20160335543A1; U.S. Ser. No. 10/632,432B2; US20210093690A1; U.S. Ser. No. 10/980,773B2; US20200352191A1; US20140065243A1; US20200254038A1; U.S. Pat. No. 9,125,859B2; US20210169795A1; U.S. Ser. No. 10/569,189B1; US20190241537A1; US20200219167A1; US20190133992A1; US20200172503A1; US20150320720A1; US20190105619A1; US20210100741A1; US20210162318A1; US20200215026A1; US20180036278A1; US20200197466A1; US20200406205A1; US20160039591A1; US20180282250A1; US20200306665A1; US20200390267A1; US20210045311A1; US20150320698A1; US20170042791A1; US20190262304A1; US20200390838A1; US20210128519A1; U.S. Ser. No. 10/976,293B2; US20200046675A1; U.S. Pat. No. 9,956,174B1; U.S. Pat. No. 9,950,976B1; U.S. Ser. No. 10/954,209B1; U.S. Ser. No. 10/568,863B2; U.S. Ser. No. 10/757,945B2; US20150150844A1; US20200038305A1; U.S. Ser. No. 10/975,395B2; US20210170302A1; US20200010786A1; US20180280459A1; US20120046351A1; US20200254407A1; U.S. Ser. No. 10/736,869B2; US20200352172A1; US20200261824A1; US20210069103A1; US20190167740A1; US20050061314A1; U.S. Ser. No. 10/561,694B2; U.S. Ser. No. 10/751,380B2; U.S. Ser. No. 10/757,944B2; U.S. Ser. No. 10/568,920B2; US20080017191A1; U.S. Pat. No. 9,655,910B2; US20200254040A1; U.S. Pat. No. 8,980,941B2; US20200122052A1; U.S. Ser. No. 10/894,224B2; U.S. Ser. No. 10/780,442B2; US20200254039A1; US20190090527A1; US20210057073A1; US20170143642A1; U.S. Ser. No. 10/028,987B1; US20200008428A1; US20210121416A1; US20210093559A1; U.S. Ser. No. 10/028,919B2; US20210252087A1; US20200329658A1; US20200188298A1; US20210059935A1; US20170000744A1; US20200330424A1; US20120046352A1; U.S. Ser. No. 10/729,665B2; US20200170994A1; US20210046041A1; US20210186893A1; US20200390739A1; US20180237368A1; US20200237679A1; U.S. Ser. No. 11/078,502B2; US20210106555A1; US20200239916A1; US20200397743A1; US20200375907A1; US20200360292A1; US20180296493A1; US20180376644P1; US20200171083A1; US20210128521A1; US20180264121A1; US20200276155A1; US20210145043A1; US20210130755A1; U.S. Ser. No. 10/596,124B2; US20190091198A1; US20200188301A1; US20170265494A1; US20190358197A1; US20200330379A1; U.S. Ser. No. 10/981,856B1; US20200408740A1; US20200069567A1; US20210228513A1; U.S. Ser. No. 10/226,433B2; US20140243405A1; USPP30434P3; US20190060381A1; US20200108027A1; US20200268817A1; US20210121403A1; US20210212929A1; US20200107510A1; US20200054702A1; U.S. Ser. No. 10/597,348B1; US20190030165A1; US20200330425A1; US20210254083A1; US20190177674A1; US20180078523A1; US20150181924A1; US20170212049A9; US20210093539A1; US20160250270A1; US20210236573A1; US20200030979A1; US20200253921A1; US20190100731A1; US20210000166A1; U.S. Ser. No. 10/368,502B2; U.S. Ser. No. 10/907,163B1; US20210045943A1; US20170304217A1;

US20200038367A1; US20200022946A1; U.S. Ser. No. 11/077,086B2; US20200165641A1; US20190183850A1; US20200108101A1; U.S. Ser. No. 10/451,480B2; U.S. Pat. No. 9,867,859B2; US20180000727A1; U.S. Pat. No. 9,597,279B2; US20170045450A1; U.S. Ser. No. 10/702,495B2; US20200361841A1; U.S. Pat. No. 9,259,449B2; US20200146999A1; USPP30668P3; US20190226912A1; US20210251950A1; US20120095088A1; US20210071186A1; US20170273937A1; US20190374501A1; US20200188812A1; US20200253922A1; US20210128658A1; US20210045933A1; U.S. Pat. No. 9,937,146B2; US20150245991A1; US20210100861A1; US20150190442A1; US20210038805A1; US20120043242A1; US20200093075A1; U.S. Ser. No. 11/076,539B2; US20190090402P1; US20200323162A1; US20190090438A1; US20210177924A1; US20160015683A1; U.S. Ser. No. 10/517,911B2; US20210077422A1; U.S. Ser. No. 10/675,252B2; US20210038558A1; US20170020943A1; US20210219512A1; U.S. Ser. No. 11/083,211B2; U.S. Ser. No. 10/933,016B2; US20200030281A1; US20200046722A1; US20200188347A1; US20200329601P1; US20130280343A1; US20190037909A1; US20190060225A1; U.S. Pat. No. 8,343,553B2; U.S. Ser. No. 10/724,048B2; US20200108018A1; US20210228502A1; US20200215022A1; US20160376211A1; U.S. Ser. No. 10/864,239B1; US20150324942A1; US20210077389A1; US20200108019A1; U.S. Ser. No. 10/155,176B1; US20210219511A1; US20180284402A1; US20180300457A1; USPP33182P3; U.S. Pat. No. 8,673,368B2; U.S. Ser. No. 10/980,743B2; US20200323164A1; US20180071246A1; US20210220282A1; US20210000789A1; U.S. Ser. No. 10/202,322B2; US20210170301A1; U.S. Ser. No. 11/077,150B2; US20210254030A1; US20210100771A1; US20210145910A1; US20210032650A1; US20210189287A1; US20200261405A1; US20180334692A1; U.S. Ser. No. 10/526,306B2; US20120263804A1; U.S. Ser. No. 10/413,523B2; U.S. Ser. No. 10/512,856B1; US20200323163A1; US20160228385A1; US20180311184A1; US20170333503A1; US20130209483A1; U.S. Ser. No. 10/308,626B1; U.S. Pat. No. 9,254,272B2; US20200345684A1; US20200030250A1; US20200170962A1; US20160184237A1; US20150324534A1; US20190282502A1; US20190352662A1; US20210212983A1; US20210136973P1; US20190221298A1; US20180344662A1; US20180170846A1; US20170362195A1; US20210040512A1; US20190256486A1; US20200215024A1; U.S. Ser. No. 10/980,772B2; US20200061004A1; U.S. Pat. No. 9,809,521B2; US20210213373A1; U.S. Ser. No. 10/864,172B2; US20190314325A1; U.S. Ser. No. 10/709,088B2; US20190192422A1; US20180344676A1; US20080103193A1; U.S. Pat. No. 9,844,518B2; U.S. Ser. No. 10/765,713B2; US20200061136A1; US20160228787A1; US20200188461A1; US20190255014A1; U.S. Ser. No. 11/026,985B2; US20170348276A1; US20210055050A1; US20180295804A1; US20200017900A1; U.S. Ser. No. 10/837,031B2; US20210046017A1; U.S. Pat. No. 9,205,063B2; U.S. Ser. No. 10/898,463B2; US20200330423A1; U.S. Ser. No. 11/007,238B2; US20210205191A1; US20180228854A1; US20200164012A1; US20190298683A1; U.S. Ser. No. 10/512,615B1; US20200199055A1; US20180035689A1; US20190321425A1; U.S. Ser. No. 10/973,864B2; US20190119694A1; US20210169823A1; US20190105298A1; U.S. Ser. No. 10/933,013B1; US20200079751A1; US20180333446A1; US20200334737A1; US20200283807A1; US20200085740A1; US20180289665A1; U.S. Ser. No. 11/046,664B2; U.S. Pat. No. 9,937,218B2; US20180360770A1; US20200093876A1; U.S. Ser. No. 10/851,077B2; US20200061021A1; US20200061023A1; U.S. Ser. No. 10/610,512B2; US20200108044A1; US20180098552A1; US20170283837A1; US20190022229A1; US20170020944A1; U.S. Ser. No. 10/793,498B2; US20210053902A1; US20190241536A1; U.S. Pat. No. 9,937,219B2; U.S. Ser. No. 10/851,076B2; US20200345657A1; US20170049830A1; U.S. Ser. No. 10/773,184B2; US20210228534A1; US20210008139A1; U.S. Ser. No. 10/799,812B2; US20210023316A1; US20200268708A1; US20210093724A1; US20150105455A1; US20210008025A1; U.S. Pat. No. 9,333,229B2; U.S. Ser. No. 11/040,295B2; U.S. Pat. No. 9,888,703B2; US20210196775A1; U.S. Pat. No. 9,918,961B2; U.S. Ser. No. 10/561,634B2; U.S. Ser. No. 10/583,160B2; US20170112161A1; US20190062144A1; US20160044934A1; U.S. Ser. No. 10/328,216B2; U.S. Ser. No. 10/925,853B2; US20210154596A1; U.S. Ser. No. 10/538,790B2; US20150136158A1; U.S. Ser. No. 10/543,176B2; US20200375918A1; US20210107884A1; US20210016202A1; U.S. Ser. No. 10/405,560B2; US20170232210A1; US20190314739A1; U.S. Ser. No. 10/960,322B2; US20170095518A1; US20180099236A1; USPP33210P3; U.S. Ser. No. 10/512,614B2; US20200181050A1; US20200163932A1; US20190083622A1; US20200147035A1; U.S. Pat. No. 9,565,865B2; U.S. Ser. No. 10/716,819B2; US20180193393A1; US20190030170A1; US20060167283A1; U.S. Ser. No. 10/046,018B2; US20170209409A1; U.S. Pat. No. 9,017,737B2; US20200190428A1; US20180141277A1; US20200155635A1; USPP33211P3; US20160256410A1; US20200245666A1; US20190142788A1; U.S. Pat. No. 9,981,203B2; U.S. Ser. No. 10/172,809B2; US20190358195A1; US20200001200A1; USPP33212P3; US20210008004A1; US20110038958A1; US20200188349A1; US20210022305A1; US20160184258A1; U.S. Ser. No. 10/413,521B2; US20100210860A1; US20210236954A1; U.S. Ser. No. 10/548,931B1; US20210023022A1; US20200222829A1; U.S. Ser. No. 10/319,475B1; US20160256435A1; US20200289654A1; US20210113490A1; US20190282643A1; US20210008026A1; US20170021029A1; US20200155469A1; US20150057341A1; US20200002306A1; US20190331656A1; U.S. Ser. No. 10/279,000B1; US20200022948A1; U.S. Ser. No. 10/617,722B2; U.S. Ser. No. 10/328,111B2; US20180325861A1; US20160171164A1; U.S. Ser. No. 10/155,018B1; U.S. Ser. No. 10/688,191B2; US20200315957A1; US20180258439A1; U.S. Pat. No. 9,326,967B2; US20210205235A1; U.S. Pat. No. 8,324,408B2; US20170266128A1; U.S. Ser. No. 11/085,047B2; US20200054245A1; US20180039741A1; US20180353558A1; US20180233558A1; US20210207154A1; US20190201463A1; US20180360739A1; U.S. Ser. No. 10/668,130B2; U.S. Ser. No. 11/007,170B2; US20190388384A1;

US20180318237A1; U.S. Pat. No. 9,849,108B2; US20050042172A1; US20180016203A1; U.S. Pat. No. 9,907,823B1; US20210052753A1; US20190117617A1; US20040049059A1; US20200402662A1; US20190224327A1; U.S. Ser. No. 10/103,225B2; US20190231833A1; US20170367386A1; US20150152018A1; US20180280473A1; US20140314757A1; US20200283283A1; US20190060300A1; US20210023044A1; US20200165544A1; U.S. Pat. No. 9,732,009B2; US20210101856A1; US20180236017A1; US20210069198A1; US20200172459A1; US20210235728A1; US20210023053A1; U.S. Ser. No. 10/807,931B2; U.S. Ser. No. 10/517,848B2; US20180318361A1; US20210015740A1; US20210186860A1; U.S. Ser. No. 10/934,554B2; U.S. Ser. No. 10/787,675B2; US20210177748A1; US20160211693A1; US20200323791A1; US20210188798A1; US20200281889A1; US20210238117A1; US20210146274A1; U.S. Ser. No. 11/072,568B2; U.S. Ser. No. 10/961,174B2; US20200289458A1; US20190110981A1; US20200079715A1; US20210084971A1; US20210144947A1; U.S. Pat. No. 9,474,725B1; US20200155629A1; US20210008138A1; US20200020449A1; U.S. Ser. No. 10/258,601B1; U.S. Ser. No. 10/870,632B2; US20190046499A1; U.S. Ser. No. 10/307,392B2; U.S. Ser. No. 11/013,685B2; US20140248379A1; US20200069776A1; US20180318529A1; US20190124864A1; US20150038567A1; US20200100433A1; U.S. Ser. No. 11/028,345B2; US20200061138A1; US20210177914A1; U.S. Ser. No. 10/512,629B1; U.S. Ser. No. 10/966,953B2; US20210017145A1; US20210213083A1; US20200237658A1; U.S. Ser. No. 10/220,063B2; US20200138773A1; U.S. Ser. No. 10/821,084B2; U.S. Pat. No. 8,895,078B2; US20190365702A1; US20200009107A1; US20190231711A1; US20190142851A1; U.S. Ser. No. 10/842,772B1; U.S. Pat. No. 9,358,259B2; U.S. Ser. No. 10/946,306B1; US20200237660A1; US20210244703A1; US20200078427A1; US20180221396A1; U.S. Ser. No. 10/991,463B2; US20210212950A1; U.S. Pat. No. 9,376,367B2; US20200172841A1; US20200078297A1; U.S. Ser. No. 11/020,355B2; US20200375938A1; US20200398182A1; US20210121435A1; US20160279183A1; US20200239428A1; U.S. Ser. No. 10/555,927B2; US20200237659A1; US20210093529A1; U.S. Ser. No. 10/933,073B2; US20210244078A1; US20200324063A1; US20210193318A1; US20190077782A1; US20120107300A1; US20200022386A1; US20180077967A1; US20210193281A1; US20190192794A1; US20190336472A1; U.S. Ser. No. 11/071,761B2; U.S. Pat. No. 8,034,843B2; US20210251976A1; U.S. Ser. No. 10/716,766B2; US20210106540A1; US20200078316A1; US20190038853A1; US20200237714A1; US20200230267A1; U.S. Ser. No. 10/933,017B2; US20210162143A1; US20160088809A1; US20200375886A1; US20170060907A1; US20210142876A1; US20200276118A1; US20130251824A1; US20210193280A1; U.S. Ser. No. 10/654,823B2; US20120059062A1; US20200315256A1; US20100286098A1; US20200276116A1; US20200128864A1; US20200325091A1; US20200237661A1; US20200206151A1; US20210241918A1; US20200276115A1; US20200390697A1; U.S. Ser. No. 10/981,850B2; U.S. Ser. No. 10/799,450B2; US20050165088A1; US20200009109A1; US20160338974A1; US20200406206A1; US20190160393A1; US20180169035A1; US20200276117A1; US20210085671A1; US20200273578A1; US20200237662A1; US20210189444A1; US20190224118A1; US20210193282A1; US20210079314A1; US20210113489A1; US20190343760A1; US20160038437A1; US20200214996A1; U.S. Ser. No. 10/195,159B2; US20200229510A1; US20170079933A1; US20200276119A1; U.S. Ser. No. 10/383,816B2; US20180224411A1; US20200000111A1; U.S. Ser. No. 10/987,321B2; US20210186418A1; US20040147767A1; U.S. Pat. No. 9,034,395B2; US20210251917A1; US20210220292A1; U.S. Ser. No. 10/188,628B1; US20210251157A1; US20150361469A1; US20190275095A1; U.S. Ser. No. 10/865,157B2; US20210186081A1; US20210163387A1; US20190083387A1; US20200237666A1; US20210154169A1; US20210015759A1; U.S. Ser. No. 10/765,658B2; U.S. Ser. No. 10/835,501B2; US20160166786A1; US20190214145A1; US20200131146A1; U.S. Ser. No. 10/695,316B2; US20200157017A1; US20170059480A1; US20160300289A1; US20200269156A1; US20180264122A1; US20140302121A1; US20210235758A1; US20180271827A1; US20210000899A1; US20190224141A1; US20180140787A1; US20210030697A1; US20180128843A1; US20190070124A1; US20190257746A1; U.S. Ser. No. 10/384,985B2; US20200197329A1; U.S. Pat. No. 9,526,715B1; US20160256411A1; U.S. Ser. No. 11/077,089B2; US20210000759A1; US20180127327A1; U.S. Ser. No. 10/756,180B2; U.S. Ser. No. 10/857,482B1; US20200123511A1; U.S. Pat. No. 8,758,826B2; US20100119606A1; U.S. Ser. No. 10/309,894B2; US20210130250A1; US20170234897A1; U.S. Pat. No. 7,622,140B2; U.S. Ser. No. 10/881,637B2; US20180230499A1; U.S. Pat. No. 9,555,019B2; US20170291120A1; U.S. Ser. No. 10/813,963B2; US20200048664A1; US20130337477A1; US20200211688A1; US20210177043A1; US20210045457A1; US20200197464A1; US20200237840A1; U.S. Ser. No. 10/813,889B2; US20190367953A1; US20200397842A1; U.S. Pat. No. 9,861,609B2; US20160355853A1; US20170135984A1; U.S. Ser. No. 10/214,753B2; US20160355854A1; US20170247650A1; U.S. Ser. No. 10/632,064B2; US20130011484A1; US20210196669A1; US20200138772A1; U.S. Ser. No. 10/265,295B2; U.S. Pat. No. 9,972,680B2; US20160018424A1; US20170152530A1; US20170368022A1; US20180271924A1; U.S. Ser. No. 10/634,689B2; U.S. Ser. No. 10/625,175B2; U.S. Ser. No. 10/084,044B2; US20210251918A1; US20190382807A1; US20210008027A1; US20200069618A1; U.S. Pat. No. 9,359,625B2; U.S. Pat. No. 9,839,612B2; US20190192429A1; US20160367479A1; US20200292564A1; US20170368020A1; US20210147770A1; US20170159080A1; US20210212381A1; US20180069078A1; US20210196637A1; U.S. Ser. No. 11/035,010B2; U.S. Ser. No. 10/472,652B2; US20190078168A1; US20170020945A1; US20190083902A1;

US20200138774A1; US20130334045A1; U.S. Ser. No. 10/081,818B2; US20210244924A1; U.S. Ser. No. 10/596,486B2; US20210177739A1; U.S. Pat. No. 9,974,739B2; US20200268646A1; US20210047583A1; US20200375882A1; US20190008845A1; US20200290791A1; U.S. Ser. No. 10/617,974B2; US20160310443A1; US20210235716A1; US20210030779A1; US20190035891A1; US20190185946A1; U.S. Pat. No. 9,308,175B2; U.S. Ser. No. 10/568,864B2; US20150132400A1; US20210177037A1; US20160367522A1; US20190321355A1; US20180233559A1; US20210177044A1; US20100008985A1; US20190366230A1; US20190183848A1; U.S. Ser. No. 10/374,036B2; US20200061195A1; U.S. Ser. No. 10/795,976B2; US20180117161A1; U.S. Ser. No. 10/381,440B2; US20210196629A1; U.S. Ser. No. 10/408,786B2; US20200352199A1; U.S. Ser. No. 11/013,715B2; US20210015786A1; US20200008442A1; U.S. Ser. No. 10/336,978B2; US20190035890A1; US20200246722A1; U.S. Ser. No. 10/894,952B2; US20200270623A1; US20210177978A1; US20030021752A1; US20200291434A1; US20170336341A1; US20210212984A1; US20190305084A1; US20210023005A1; US20210000742A1; US20190355472A1; US20200197462A1; US20180116240A1; US20180346866A1; US20200323773A1; US20200345816A1; US20170266397A1; US20200253923A1; US20210163438A1; US20190316144A1; US20200046639A1; US20190015382A1; U.S. Pat. No. 9,879,292B2; US20200138885A1; US20190382708A1; US20090318526A1; US20200121616A1; US20200178572A1; US20200254271A1; US20210131953A1; US20200352901A1; US20190275270A1; US20190225975A1; US20210236457A1; US20170172977A1; US20160331913A1; US20200376241A1; U.S. Ser. No. 10/471,223B2; US20200069896A1; US20200340026A1; US20180343812A1; US20200297025A1; US20200193861A1; US20170112855A1; US20160340629A1; U.S. Ser. No. 10/704,066B2; US20200101041A1; U.S. Pat. No. 9,394,510B2; US20180092392A1; US20200035121A1; US20180344686A1; US20210235752A1; US20170298399A1; US20210153566A1; U.S. Ser. No. 10/820,624B2; US20180320209A1; US20160264917A1; U.S. Ser. No. 10/777,091B2; US20200035120A1; U.S. Ser. No. 10/633,681B2; US20190382814A1; US20180155748A1; U.S. Ser. No. 10/897,925B2; US20180179564A1; US20210236458A1; US20160053220A1; U.S. Ser. No. 10/080,736B2; US20190328699A1; U.S. Pat. No. 9,833,461B2; US20200063171A1; US20200193862A1; US20210051995A1; US20200086228A1; US20200051455A1; U.S. Pat. No. 9,854,828B2; US20180071654A1; U.S. Pat. No. 9,587,212B2; U.S. Ser. No. 10/966,924B2; US20200268681A1; US20210137137A1; US20200405657A1; U.S. Ser. No. 10/787,674B2; US20180311180A1; US20170312474A1; US20210251947A1; US20180296498A1; U.S. Pat. No. 9,512,391B2; U.S. Ser. No. 10/982,243B2; US20200146996A1; U.S. Ser. No. 10/486,083B2; U.S. Ser. No. 10/435,727B2; US20210153565A1; US20170360861A1; US20160088870A1; US20210040492A1; US20180311181A1; U.S. Ser. No. 10/988,785B1; US20210177041A1; U.S. Ser. No. 11/052,055B2; US20200206185A1; US20200305265A1; US20200370073A1; US20190336521A1; US20200237622A1; US20180280637A1; US20170252300A1; US20160298151A1; US20200085739A1; US20170233778A1; U.S. Ser. No. 11/028,417B1; US20190038663A1; US20200063170A1; U.S. Ser. No. 10/383,892B2; US20180000857A1; US20190281871A1; US20210153569A1; US20160331720A1; US20200360239A1; U.S. Ser. No. 10/143,706B2; U.S. Ser. No. 10/537,592B2; US20160243460A1; US20200120987A1; US20210145077A1; US20210161833A1; US20200281278A1; US20210007407A1; US20210153568A1; US20210059307A1; US20160157524A1; US20210189402A1; US20200398180A1; U.S. Ser. No. 10/512,282B2; US20200375940A1; US20200035118A1; US20200138730A1; U.S. Ser. No. 11/017,689B2; US20190046598A1; US20200229411A1; US20210228497A1; US20190246591A1; US20210082307A1; US20210085666A1; US20150313868A1; US20210071209A1; US20210177036A1; US20210030777A1; US20190254969A1; US20190046440A1; US20180311205A1; US20180043114A1; US20200035119A1; U.S. Ser. No. 10/878,717B2; US20210089946A1; US20200345585A1; U.S. Ser. No. 10/350,165B2; US20190380388A1; US20200330382A1; U.S. Ser. No. 10/548,840B2; US20180344954A1; US20190076355A1; US20210015746A1; US20180093054A1; US20210236456A1; US20190085279A1; US20170136196A1; US20190054176A1; US20210177754A1; US20200352249A1; US20210065860A1; US20200315253A1; US20210045998A1; US20200069605A1; US20210161201A1; U.S. Ser. No. 10/080,851B2; US20190192810A1; US20210145036A1; US20200253948A1; US20140357708A1; US20190247358A1; US20200253947A1; US20200016092A1; US20200069604A1; US20190314326A1; US20210085596A1; US20200046007A1; US20190247325A1; US20210169759A1; U.S. Ser. No. 10/738,268B2; US20180184705A1; U.S. Ser. No. 10/974,165B2; US20170266127A1; U.S. Ser. No. 10/542,770B2; US20210030768A1; U.S. Ser. No. 10/751,299B2; US20200405980A1; U.S. Ser. No. 10/595,555B2; US20200196656A1; US20210177042A1; US20200069606A1; US20210211867A1; US20100029739A1; U.S. Ser. No. 10/695,301B2; US20200047082A1; US20180353461A1; US20210169125A1; US20190070396A1; US20200146361A1; US20210154420A1; US20210251276A1; US20210169806A1; U.S. Ser. No. 10/871,467B2; US20210145841A1; US20200163900A1; US20210244686A1; US20210196644A1; US20210219622A1; US20210177738A1; US20170224841A1; US20200383331A1; US20210177740A1; US20190376929A1; US20210219589A1; US20200093755A1; US20210169820A1; US20180137125A1; US20200316151A1; US20210169791A1; US20210236433A1; US20210169790A1; US20210077411A1; US20210204590A1; U.S. Ser. No. 10/945,953B1; US20210213091A1; US20210172091A1; U.S. Ser. No. 10/927,477B2; US20170224842A1;

US20210169816A1; US20200340145A1; US20210177038A1; US20190314296A1; US20210219573A1; US20090068143A1; US20210145764A1; US20200261387A1; US20200224231A1; US20210045452A1; US20210244684A1; U.S. Ser. No. 10/966,946B2; U.S. Pat. No. 8,410,064B2; US20210128534A1; US20210009548A1; U.S. Ser. No. 10/888,666B2; US20210016020A1; US20190364968A1; U.S. Ser. No. 10/888,665B2; US20190364957A1; US20210085887A1; US20190364969A1; US20190369127A1; U.S. Ser. No. 10/301,242B2; US20210085888A1; US20200396961A1; US20200206415A1; US20200206430A1; US20180362429A1; US20210219608A1; US20210153562A1; US20190373679A1; US20210205224A1; US20210046261A1; US20200215047A1; US20190358169A1; US20190300888A1; U.S. Ser. No. 10/563,211B2; US20200172917A1; U.S. Ser. No. 10/975,379B2; US20110092583A1; US20210038559A1; U.S. Pat. No. 9,265,724B2; US20200069638A1; US20200069581A1; US20210177858A1; US20200329775A1; US20200289768A1; US20190247299A1; U.S. Ser. No. 10/265,292B2; US20110281885A1; US20080153835A1; U.S. Pat. No. 7,279,493B2; U.S. Pat. No. 7,799,786B2; US20040106625A1; US20100210686A1; U.S. Pat. No. 8,349,842B2; US20060199824A1; U.S. Pat. No. 7,572,812B2; US20200170272A1; US20210195908A9; US20110206816A1; US20160081975A1; US20040127501A1; US20200306463A1; US20160370337A1; U.S. Ser. No. 11/046,978B2; US20190352679A1; US20100004254A1; US20120004217A1; US20140142112A1; US20120015954A1; U.S. Pat. No. 8,008,300B2; U.S. Pat. No. 9,434,721B2; U.S. Pat. No. 7,582,635B2; U.S. Pat. No. 8,604,037B2; U.S. Pat. No. 8,536,177B2; US20040186111A1; US20160081927A1; U.S. Ser. No. 10/016,363B2; US20180098962A1; US20160081976A1; U.S. Pat. No. 9,861,611B2; U.S. Ser. No. 10/285,971B2; US20210115513A1; U.S. Ser. No. 11/078,247B2; US20190241633A1; US20180126003A1; US20210252122A1; US20210205428A1; and US20190192691A1.

Alam, Safaet, Md Sarker, Moklesur Rahman, Sadia Afrin, Fahmida Tasnim Richi, Chao Zhao, Jin-Rong Zhou, and Isa Naina Mohamed. "Traditional Herbal Medicines, Bioactive Metabolites, and Plant Products Against COVID-19: Update on Clinical Trials and Mechanism of Actions." *Frontiers in Pharmacology* 12 (2021): 1248.

Alexander S P H, Mathie A, Peters J A. Guide to Receptors and Channels (GRAC), 4th edition. Br J Pharmacol. 2009; 158(Suppl 1):S1-S254.

Anand P, Thomas S G, Kunnumakkara A B, Sundaram C, Harikumar K B, Sung B, et al. Biological activities of curcumin and its analogues (Congeners) made by man and Mother Nature. Biochem Pharmacol. 2008; 76:S1590-S1611.

Arnold, William R., Austin T. Weigle, and Aditi Das. "Crosstalk of cannabinoid and endocannabinoid metabolism is mediated via human cardiac CYP2J2." *Journal of inorganic biochemistry* 184 (2018): 88-99.

Banni S, Di Marzo V. Effect of dietary fat on endocannabinoids and related mediators: Consequences on energy homeostasis, inflammation and mood. Mol Nutr Food Res. 2009; 54:S82-S92.

Bisht K, Wagner K H, Bulmer A C. Curcumin, resveratrol and flavonoids as anti-inflammatory, cyto- and DNA-protective dietary compounds. Toxicology. 2009 (doi: 10.1016/j.tox.2009.11.008).

Bolognini D, Costa B, Maione S, Comelli F, Marini P, Di Marzo V, et al. The plant cannabinoid Δ9-tetrahydrocannabivarin can decrease signs of inflammation and inflammatory pain in mice. Br J Pharmacol. 2010; 160:677-687.

Boocock D J, Patel K R, Faust G E, Normolle D P, Marczylo T H, Crowell J A, et al. Quantitation of trans-resveratrol and detection of its metabolites in human plasma and urine by high performance liquid chromatography. J Chromatogr B Analyt Technol Biomed Life Sci. 2007; 848:S182-S187.

Borrelli F, Fasolino I, Romano B, et al. Beneficial effect of the non-psychotropic plant cannabinoid cannabigerol on experimental inflammatory bowel disease. Biochemical Pharmacology. 2013; 85(9):1306-1316.

Capasso R, Borrelli F, Cascio M G, Aviello G, Huben K, Zjawiony J K, et al. Inhibitory effect of salvinorin A, from *Salvia divinorum*, on ileitis-induced hypermotility: crosstalk between kappa-opioid and cannabinoid CB(1) receptors. Br J Pharmacol. 2008; 155:S681-S689.

Carvalho, Renata K., Monica L. Andersen, and Renata Mazaro-Costa. "The effects of cannabidiol on male reproductive system: A literature review." *Journal of Applied Toxicology* 40, no. 1(2020): 132-150.

Chen, N.; Zhou, M.; Dong, X.; Qu, J.; Gong, F.; Han, Y. et al. Epidemiological and clinical characteristics of 99 cases of 2019 novel coronavirus pneumonia in Wuhan, China: a descriptive study. Lancet 2020, 395(10223), 507-513.

Chicca A, Raduner S, Pellati F, Strompen T, Altmann K H, Schoop R, et al. Synergistic immunomopharmacological effects of N-alkylamides in *Echinacea purpurea* herbal extracts. Int Immunopharmacol. 2009; 9:5850-5858.

Colasanti B K. A comparison of the ocular and central effects of tetrahydrocannabinol and cannabigerol. Journal of Ocular Pharmacology and Therapeutics. 1990; 6(4): 259-269.

Coronaviridae Study Group of the International Committee on Taxonomy of V The species severe acute respiratory syndrome-related coronavirus: classifying 2019-nCoV and naming it SARS-CoV-2. Nat Microbiol 2020, 5(4), 536-544.

De Petrocellis L, Di Marzo V. Non-CB(1), Non-CB(2) receptors for endocannabinoids, plant cannabinoids, and synthetic cannabimimetics: focus on G-protein-coupled receptors and transient receptor potential channels. J Neuroimmune Pharmacol. 2010; 5:103-121.

Deb, Subrata, and Scott Arrighi. "Potential effects of COVID-19 on cytochrome P450-mediated drug metabolism and disposition in infected patients." *European Journal of Drug Metabolism and Pharmacokinetics* (2021): 1-19.

Di Marzo V, Bisogno T, Petrocellis L. Endocannabinoids and related compounds: walking back and forth between plant natural products and animal physiology. Chem Biol. 2007; 14:5741-5756.

Di Marzo V, Sepe N, De Petrocellis L, Berger A, Crozier G, Fride E, et al. Trick or treat from food endocannabinoids. Nature. 1998; 396:S636-S637.

Di Marzo V. Targeting the endocannabinoid system: to enhance or reduce? Nat Rev Drug Discov. 2008; 7:S438-S455.

Di Tomaso E, Beltramo M, Piomelli D. Brain cannabinoids in chocolate. Nature. 1996; 382:S677-S678.

Drosten, C.; Gunther, S.; Preiser, W.; Van der Werf, S.; Brodt, H. R.; Becker, S.; Rabenau, H.; Panning, M.; Kolesnikova, L.; Fouchier, R. A.; Berger, A.; Burguiere, A. M.; Cinatl, J.; Eickmann, M.; Escriou, N.; Grywna, K.; Kramme, S.; Manuguerra, J. C.; Muller, S.; Rickerts, V.; Sturmer, M.; Vieth, S.; Klenk, H. D.; Osterhaus, A. D.; Schmitz, H.; Doerr, H. W. Identification of a novel coronavirus in patients with severe acute respiratory syndrome. N. Engl. J. Med 2003, 348, 1967-1976.

DuPont M S, Day A J, Bennett R N, Mellon F A, Kroon P A. Absorption of kaempferol from endive, a source of kaempferol-3-glucuronide, in humans. Eur J Clin Nutr. 2004; 58:S947-S954.

Ethan B Russo, Carrie Cuttler, Ziva D Cooper, Amanda Stueber, Venetia L Whiteley, Michelle Sexton, Survey of Patients Employing Cannabigerol-Predominant *Cannabis* Preparations: Perceived Medical Effects, Adverse Events, and Withdrawal Symptoms, *Cannabis* Cannabinoid Res, 2021 Sep. 27. doi: 10.1089/can.2021.0058.PMID: 34569849 DOI: 10.1089/can.2021.0058

Farha M A, El-Halfawy O M, Gale R T, et al. Uncovering the hidden antibiotic potential of *Cannabis*. ACS Infect Dis. 2020; 6(3):338-346.

Fichna J, Schicho R, Andrews C N, Bashashati M, Klompus M, McKay D M, et al. Salvinorin A inhibits colonic transit and neurogenic ion transport in mice by activating kappa-opioid and cannabinoid receptors. Neurogastroenterol Motil. 2009; 21:51326-Se128.

Garcea G, Jones D J, Singh R, Dennison A R, Farmer P B, Sharma R A, et al. Detection of curcumin and its metabolites in hepatic tissue and portal blood of patients following oral administration. Br J Cancer. 2004; 90:S1011-S1015.

Gertsch J, Leonti M, Raduner S, Racz I, Chen J Z, Xie X Q, et al. Beta-caryophyllene is a dietary cannabinoid. Proc Natl Acad Sci USA. 2008; 105:S9099-S9104.

Gertsch J, Raduner S, Altmann K H. New natural noncannabinoid ligands for cannabinoid type-2 (CB2) receptors. J Recept Signal Transduct Res. 2006; 26:5709-5730.

Gertsch J. Anti-inflammatory cannabinoids in diet: towards a better understanding of CB(2) receptor action? Commun Integr Biol. 2008; 1:S26-S28.

Gertsch J. How scientific is the science in ethnopharmacology: historical perspectives and epistemiological problems. J Ethnopharmacol. 2009; 122:S177-S183.

Gertsch, Jürg, Roger G. Pertwee, and Vincenzo Di Marzo. "Phytocannabinoids beyond the *Cannabis* plant-do they exist?." British journal of pharmacology 160, no. 3 (2010): 523-529.

Huang, C.; Wang, Y.; Li, X.; Ren, L.; Zhao, J.; Hu, Y.; et al. Clinical features of patients infected with 2019 novel coronavirus in Wuhan, China. Lancet 2020, 395(10223), 497-506.

Huff, Hannah C., Archit Vasan, Pritam Roy, Aayush Kaul, Emad Tajkhorshid, and Aditi Das. "Differential Interactions of Selected Phytocannabinoids with Human CYP2D6 Polymorphisms." *Biochemistry* 60, no. 37 (2021): 2749-2760.

Hui, D. S.; I Azhar, E.; Madani, T. A.; Ntoumi, F.; Kock, R.; Dar, O.; Ippolito, G.; Mchugh, T. D.; Memish, Z. A.; Drosten, C.; Zumla, A.; Petersen, E. The continuing 2019-nCoV epidemic threat of novel coronaviruses to global health The latest 2019 novel coronavirus outbreak in Wuhan, China. Int J of Infec Dis 2020, 91, 264-266.

Huynh Thi Phuong Loan, Nguyen Thi Thanh Hai, Dr. Le Trung Hieu, Prof. Tran Thai Hoa, Dr. Bui Thi Phuong Thuy, Prof. Duong Tuan Quang, Dr. Nguyen Thanh Triet, Evaluation of the Inhibitory Activities of COVID-19 of *Melaleuca cajuputi* Oil Using Docking Simulation, ChemistrySelect 2020, 5, 6312-6320, chemistry-europe-.onlinelibrary.wiley.com/doi/10.1002/slct.202000822.

Izgelov, Dvora, Abraham J. Domb, and Amnon Hoffman. "The effect of piperine on oral absorption of cannabidiol following acute vs. chronic administration." *European Journal of Pharmaceutical Sciences* 148 (2020): 105313.

King A R, Dotsey E Y, Lodola A, Jung K M, Ghomian A, Qiu Y, et al. Discovery of potent and reversible monoacylglycerol lipase inhibitors. Chem Biol. 2009; 16:1045-1052.

Kogan, Natalya M., Yarden Lavi, Louise M. Topping, Richard Williams, Fiona E. McCann, Zhanna Yekhtin, Marc Feldmann, Ruth Gallily, and Raphael Mechoulam. "Novel CBG Derivatives Can Reduce Inflammation, Pain and Obesity." *Molecules* 26, no. 18 (2021): 5601.

Korte G, Dreiseitel A, Schreier P, Oehme A, Locher A, Goeran H, et al. An examination of anthocyanins' and anthocyanidins' affinity for cannabinoid receptors. J Med Food. 2009; 12:S1407-51410.

Korte G, Dreiseitel A, Schreier P, Oehme A, Locher S, Geiger S, et al. Tea catechins' affinity for human cannabinoid receptors. Phytomedicine. 2010; 17:519-522.

Ksiazek, T. G.; Erdman, D.; Goldsmith, C. S.; Zaki, S. R.; Peret, T.; Emery, S.; Tong, S.; Urbani, C.; Comer, J. A.; Lim, W.; Rollin, P. E.; Dowell, S. F.; Ling, A. E.; Humphrey, C. D.; Shieh, W. J.; Guarner, J.; Paddock, C. D.; Rota, P.; Fields, B.; DeRisi, J.; Yang, J. Y.; Cox, N.; Hughes, J. M.; LeDuc, J. W.; Bellini, W. J.; Anderson, L. J. A novel coronavirus associated with severe acute respiratory syndrome. N. Engl. J. Med 2003, 348, 1953-1966.

Landis-Piwowar K R, Dou Q P. Polyphenols: biological activities, molecular targets, and the effect of methylation. Curr Mol Pharmacol. 2008; 1:S233-S243.

Lenoir, Camille, Jean Terrier, Yvonne Gloor, François Curtin, Victoria Rollason, Jules Alexandre Desmeules, Youssef Daali, Jean-Luc Reny, and Caroline Flora Samer. "Impact of SARS-CoV-2 Infection (COVID-19) on Cytochromes P450 Activity Assessed by the Geneva Cocktail." *Clinical Pharmacology & Therapeutics* 110, no. 5 (2021): 1358-1367.

Leonti M, Casu L, Raduner S, Cottiglia F, Floris C, Altmann K-H, et al. Falcarinol is a covalent cannabinoid CB1 receptor antagonist and induces pro-allergic effects in skin. Biochem Pharmacol. 2010 doi: 10.1016/j.bcp.2010.02.015 accepted.

Malabadi, Ravindra B., Neelambika T. Meti, and Raju K. Chalannavar. "Role of herbal medicine for controlling coronavirus (SARS-CoV-2) disease (COVID-19)." *International Journal of Research and Scientific Innovations* 8, no. 2 (2021): 135-165.

Malabadi, Ravindra B., P. Kolkar, T. Meti, and K. Chalannavar. "Traditional Herbal Folk Medicine Used For Controlling Corona Virus (SARS-COV-2) DISEASE (COVID-19)." *International Journal of Innovation Scientific Research and Review.* 2021i 3, no. 7: 1507-1517.

Maor Y, Morowitz M, Gallily R, Mechoulam R (2005) Cannabigerol-dimethyl heptyl (CBG-DMH), a synthetic cannabinoid with hypotensive and vasorelaxant properties. Presented at the symposium of the International Cannabinoid Research Society, Clearwater, FL, June 2005

Markuu, P. Sleep research in 2020: COVID-19-related sleep disorders. The Lancet Neurology 2021, 20(1), 15-17.

Maurelli S, Bisogno T, De Petrocellis L, Di Luccia A, Marino G, Di Marzo V. Two novel classes of neuroactive fatty acid amides are substrates for mouse neuroblastoma 'anandamide amidohydrolase. FEBS Lett. 1995; 377:S82-S86.

Mechoulam R. Interview with Prof. Raphael Mechoulam, codiscoverer of THC. Interview by Stanley Einstein. Int J Addict. 1986; 21:5579-5587.

Millar, Sophie Anne, Ryan Francis Maguire, Andrew Stephen Yates, and Saoirse Elizabeth O'Sullivan. "Towards better delivery of cannabidiol (CBD)." *Pharmaceuticals* 13, no. 9 (2020): 219.

Nachnani, Rahul, Wesley M. Raup-Konsavage, and Kent E. Vrana. "The Pharmacological Case for Cannabigerol." Journal of Pharmacology and Experimental Therapeutics 376, no. 2 (2021): 204-212.

Nadolska, Krystyna, and Roman Goś. "Possibilities of applying cannabinoids' in the treatment of glaucoma." *Klinika oczna* 110, no. 7-9 (2008): 314-317.

Nakano, Yukako, Masataka Tajima, Erika Sugiyama, Vilasinee Hirunpanich Sato, and Hitoshi Sato. "Development of a novel nanoemulsion formulation to improve intestinal absorption of cannabidiol." Medical *Cannabis* and Cannabinoids 2, no. 1 (2019): 35-42.

Nelson, Kathryn M., Jonathan Bisson, Gurpreet Singh, James G. Graham, Shao-Nong Chen, J. Brent Friesen, Jayme L. Dahlin, Matthias Niemitz, Michael A. Walters, and Guido F. Pauli. "The essential medicinal chemistry of cannabidiol (CBD)." *Journal of medicinal chemistry* 63, no. 21(2020): 12137-12155.

Nguyen, Long Chi, Dongbo Yang, Vlad Nicolaescu, Thomas Best, Shaonong Chen, J. Brent Friesen, Nir Drayman et al. "Cannabidiol inhibits SARS-CoV-2 replication and promotes the host innate immune response." *bioRxiv* (2021).

Oesch S, Gertsch J. *Cannabis* receptor ligands as potential anticancer agents—high hopes for new therapies? J Pharm Pharmacol. 2009; 61:5839-5853.

Orrego-González E, Londoño-Tobón L, Ardila-González J, Polania-Tovar D, Valencia-Cárdenas A, Velez-Van Meerbeke A. Cannabinoid effects on experimental colorectal cancer models reduce aberrant crypt foci (Acf) and tumor volume: a systematic review. Evidence-Based Complementary and Alternative Medicine. 2020; 2020:1-13.

O'Sullivan S E. Cannabinoids go nuclear: evidence for activation of peroxisome proliferator-activated receptors. Br J Pharmacol. 2007; 152:576-582.

Pagano E, Montanaro V, Di Girolamo A, Pistone A, Altieri V, Zjawiony J K, Izzo A A, Capasso R. Effect of Non-psychotropic Plant-derived Cannabinoids on Bladder Contractility: Focus on Cannabigerol. Nat Prod Commun. 2015 June; 10(6):1009-12. PMID: 26197538.

Paland, Nicole, Antonina Pechkovsky, Miran Aswad, Haya Hamza, Tania Popov, Eduardo Shahar, and Igal Louria-Hayon. "The Immunopathology of COVID-19 and the *Cannabis* Paradigm." *Frontiers in Immunology* 12 (2021): 327.

Peiris, J. S.; Lai, S. T.; Poon, L. L.; Guan, Y.; Yam, L. Y.; Lim, W.; Nicholls, J.; Yee, W. K.; Yan, W. W.; Cheung, M. T.; Cheng, V. C.; Chan, K. H.; Tsang, D. N.; Yung, R. W.; Ng, T. K.; Yuen. K. Y. Coronavirus as a possible cause of severe acute respiratory syndrome. Lancet 2003, 361, 1319-1325.

Pertwee R G. Cannabinoid pharmacology: the first 66 years. Br J Pharmacol. 2006; 147:S163-S171.

Pertwee R G. Emerging strategies for exploiting cannabinoid receptor agonists as medicines. Br J Pharmacol. 2009; 156:S397-S411.

Pertwee R G. Receptors targeted by synthetic cannabinoid receptor agonists and antagonists. Curr Med Chem. 2010; 17:1360-1381.

Pertwee R G. The therapeutic potential of drugs that target cannabinoid receptors or modulate the tissue levels or actions of endocannabinoids. AAPS J. 2005; 7:E625-E654.

Pieracci, Ylenia, Roberta Ascrizzi, Valentina Terreni, Luisa Pistelli, Guido Flamini, Laura Bassolino, Flavia Fulvio, Massimo Montanari, and Roberta Paris. "Essential Oil of *Cannabis sativa* L: Comparison of Yield and Chemical Composition of 11 Hemp Genotypes." Molecules 26, no. 13 (2021): 4080;

Prather P L, Seely K A, Levi M S. Notice of retraction. J Pharmacol Exp Ther. 2009; 331:1147.

Raduner S, Majewska A, Chen J Z, Xie X Q, Hamon J, Faller B, et al. Alkylamides from *Echinacea* are a new class of cannabinomimetics. Cannabinoid type-2 receptor-dependent and -independent immunomodulatory effects. J Biol Chem. 2006; 281:S14192-S1S206.

Radwan, Mohamed M., Suman Chandra, Shahbaz Gul, and Mahmoud A. ElSohly. "Cannabinoids, Phenolics, Terpenes and Alkaloids of *Cannabis*." Molecules 26, no. 9 (2021): 2774.

Ramirez, Cristina Lujan, Maria Alejandra Fanovich, and Maria Sandra Churio. "Cannabinoids: extraction methods, analysis, and physicochemical characterization." In Studies in natural products chemistry, vol. 61, pp. 143-173. Elsevier, 2019.

Rios J L. Effects of triterpenes on the immune system. J Ethnopharmacol. 2010; 128:1-14.

Rock, E. M., Goodwin, J. M., Limebeer, C. L. et al. Interaction between non-psychotropic cannabinoids in marihuana: effect of cannabigerol (CBG) on the anti-nausea or anti-emetic effects of cannabidiol (CBD) in rats and shrews. Psychopharmacology 215, 505-512 (2011). doi.org/10.1007/s00213-010-2157-4

Rollinger J M, Schuster D, Danzl B, Schwaiger S, Markt P, Schmidtke M, et al. In silico fishing for rationalized ligand discovery exemplified on constituents of *Ruta graveolens*. Planta Med. 2009; 75:S195-5204.

Ross R A. The enigmatic pharmacology of GPR55. Trends Pharmacol Sci. 2009; 30:S156-5163.

Salvinorin A, a diterpene in *Salvia* divinorum, produces CB1-mediated effects in the gastrointestinal tract of rodents. Salvinorin A primarily acts as a kappa-opioid receptor agonist and is inactive as a ligand for CB1 and CB2 (Capasso et al., 2008); it may interact with a putative CB1-kappa-opioid receptor heterodimer (Fichna et al., 2012).

Seegehalli M. Anil, Nurit Shalev, Ajjampura C. Vinayaka, Stalin Nadarajan, Dvora Namdar, Eduard Belausov, Irit Shoval, Karthik Ananth Mani, Guy Mechrez & Hinanit Koltai *Cannabis* compounds exhibit anti-inflammatory activity in vitro in COVID-19-related inflammation in lung epithelial cells and pro-inflammatory activity in macrophages, Nature Research, (2021) 11:1462 doi.org/10.1038/s41598-021-81049-2

Seely K A, Levi M S, Prather P L. The dietary polyphenols trans-resveratrol and curcumin selectively bind human CB1 cannabinoid receptors with nanomolar affinities and function as antagonists/inverse agonists. J Pharmacol Exp Ther. 2009; 330:S31-S39.

Sharifian-Dorche, M.; Huot, P.; Osherov, M. et al. Neurological complications of coronavirus infection; a comparative review and lessons learned during the COVID-19 pandemic. J Neurol Sci 2020, 417, 117085.

Shrestha R, Kim S C, Dyer J M, Dixon R A, Chapman K D. Plant fatty acid (ethanol) amide hydrolases. Biochim Biophys Acta. 2006; 1761:S324-S334.

Slomski A. Trials Test Mushrooms and Herbs as Anti-COVID-19 Agents. *JAMA*. Published online Nov. 3, 2021. doi:10.1001/jama.2021.19388

Spelman K, Iiams-Hauser K, Cech N B, Taylor E W, Smirnoff N, Wenner C A. Role for PPARgamma in IL-2 inhibition in T cells by *Echinacea*-derived undeca-2E-ene-8,10-diynoic acid isobutylamide. Int Immunopharmacol. 2009; 9:S1260-S1264.

Tagne, Alex Mabou, Yannick Fotio, Lin Lin, Erica Squire, Faizy Ahmed, Tarif Ibne Rashid, Elnaz Karimian Azari, and Daniele Piomelli. "Palmitoylethanolamide and hemp oil extract exert synergistic anti-nociceptive effects in mouse models of acute and chronic pain." Pharmacological research 167 (2021): 105545.

Thors L, Alajakku K, Fowler C J. The 'specific' tyrosine kinase inhibitor genistein inhibits the enzymic hydrolysis of anandamide: implications for anandamide uptake. Br J Pharmacol. 2007; 150:5951-5960.

Thors L, Belghiti M, Fowler C J. Inhibition of fatty acid amide hydrolase by kaempferol and related naturally occurring flavonoids. Br J Pharmacol. 2008; 155:5244-5252.

Tiwari, Anshuly, Kakasaheb R. Mahadik, and Satish Y. Gabhe. "Piperine: A comprehensive review of methods of isolation, purification, and biological properties." Medicine in Drug Discovery 7 (2020): 100027.

*Trametes versicolor* (mushroom, often has algae symbiosis), *Fomitopsis officinalis* (mushroom), modified Qing Fei PaiDu Tang (herbal) are currently undergoing clinical trials in US for prevention, as adjunctive treatment/symptoms control, or to facilitate recovery of Covid-19.

US Plant Patent number US PP32,725 P2: The *Panakeia* Plant.

Valdeolivas S, Navarrete C, Cantarero I, Bellido M L, Munoz E, Sagredo O. Neuroprotective properties of cannabigerol in huntington's disease: studies in r6/2 mice and 3-nitropropionate-lesioned mice. Neurotherapeutics. 2015; 12(1):185-199.

Varatharaj, A.; Thomas, N.; Ellul, M. A.; Davies, N. W. S.; Pollak, T. A.; Tenorio, E. L.; Sultan, M.; Easton, A.; Breen, G.; Zandi, M.; Coles, J. P.; Manji, H.; Al-Shahi Salman, R.; Menon, D. K.; Nicholson, T. R.; Benjamin, L. A.; Carson, A.; Smith, C.; Turner, M. R.; Solomon, T.; Kneen, R.; Pett, S. L.; Galea, I.; Thomas, R. H.; Michael, B. D.; CoroNerve Study Group. Neurological and neuropsychiatric complications of COVID-19 in 153 patients: a U K-wide surveillance study. Lancet Psychiatry 2020, 7(10), 875-882.

Wang, Bo, Anna Kovalchuk, Dongping Li, Rocio Rodriguez-Juarez, Yaroslav Ilnytskyy, Igor Kovalchuk and Olga Kovalchuk, "In search of preventive strategies: novel high-CBD *Cannabis sativa* extracts modulate ACE2 expression in COVID-19 gateway tissues" 22 Nov. 2020, Aging-US. DOI: 10.18632/aging.202225

Webster, R. G. Wet markets—a continuing source of severe acute respiratory syndrome and influenza? Lancet 2004, 363, 234-236.

Woelkart K, Dittrich P, Beubler E, Pinl F, Schoop R, Suter A, et al. Pharmacokinetics of the main alkamides after administration of three different *Echinacea purpurea* preparations in humans. Planta Med. 2008; 74:5651-5656.

Woo, P. C.; Lau, S. K.; Yuen, K. Infectious diseases emerging from Chinese wet-markets: zoonotic origins of severe respiratory viral infections. Curr. Opin. Infect. Dis 2006, 19, 401-407.

Yin H, Chu A, Li W, Wang B, Shelton F, Otero F, et al. Lipid G protein-coupled receptor ligand identification using beta-arrestin PathHunter assay. J Biol Chem. 2009; 284: S12328-S12338.

Zendulka, Ondrej, Gabriela Dovrtelová, Kristýna Nosková, Miroslav Turjap, Alexandra Sulcová, Lumir Hanus, and Jan Jurica. "Cannabinoids and cytochrome P450 interactions." *Current drug metabolism* 17, no. 3 (2016): 206-226

Zhang, Lihua, Xin Zheng, Xueke Bai, Qing Wang, Bowang Chen, Haibo Wang, Jiapeng Lu et al. "Association between Use of Qingfei Paidu Tang and Mortality in Hospitalized Patients with COVID-19: A national retrospective registry study." *Phytomedicine* 85 (2021): 153531.

Zhou, F.; Yu, T.; Du, R.; Fan, G.; Liu, Y.; Liu, Z. et al. Clinical course and risk factors for mortality of adult inpatients with COVID-19 in Wuhan, China: a retrospective cohort study.

Zimmer A, Racz I, Klauke A L, Markert A, Gertsch J. Beta-caryophyllene, a phytocannabinoid acting on CB2 receptors. 2009. IACM 5th Conference on cannabinoids in medicine, 2-3. October, Cologne, Germany.

SUMMARY OF THE INVENTION

A cannabinoid composition, comprising at least 5% cannabigerol, in combination with *Cannabis* terpenes, substantially without cannabidiol, tetrahydrocannabinol, and solvent residue, identified as *Panakeia* full spectrum oil, through a novel *Panakeia* plant with a patented extraction process that does not require an isolated product (CBG) as the critical foundation (without using an expensive solvent which can result in contamination of the product). The parameters of extraction through the Herbolea process, or equivalent are specified to account for the lower boiling point of CBG (compared to CBD).

The full spectrum extract from the *Panakeia* plant has been designated as Bazelet Health Systems, Inc.'s proprietary Plant-based EndoCannabinoid System Activating compound (PECSA™ "original") which is comprised of the naturally occurring cannabinoids and other non-cannabinoid components that are co-extracted with the at least one CBGA (and to a lesser extent, CBGVA) or decarboxylated derivative-type compound (CBG, and to a lesser extent CBGV), (the "Product"). In other PECSA™ iterations, the *Panakeia* "full spectrum" CBG extract is concentrated, with other additive, substitutions or deletions, or combined with other natural ingredients to enhance effect, absorption and flavor, to form the novel proprietary food product. In one embodiment. The PECSA™ extract will contain primarily CBGA, or converted in some proportion to CBG, or be enriched from products from the *Panakeia*™ plant including higher concentrations of CBG. In other words, the extract contains a greater proportion of the total cannabinoid content of CBG as compared to the cannabinoid composition from which the extract was prepared primarily by purifying the plant extract further after extraction to select specifically for CBG (through patented methods for the exact extraction parameters for optimization of product yield). The therapeutic effects of PECSA™ are due to the combined ingredients as a synergistic or entourage effect, with CBGA/CBG as the primary ingredients. Although they are similar compounds, CBGA (an acid) and CBG, may have different therapeutic applications and benefits than if they were administered as an individual component.

The full spectrum oil that will be standardized from the Panakeia™ plant (PECSA™ original) is enriched by distillation and has been determined to contain CBGA (up to 99%, based on batch analysis which is concentrated during extraction); it can contain CBG, with conversion to CBGA to equivalent CBG by 0.877 by heating.

With additional extraction procedures, isolated or substantially pure cannabigerols will be substantially free of other cannabinoids and other non-cannabinoid components such as terpenes.

This Product can then be modified with additional additives that can improve bioavailability, e.g., piperine, a component of white pepper and black pepper.

Cordyceps sinensis extract, combined with Panakeia extract, mutually enhances the beneficial effects as an antioxidant, which may be clinically applicable in circulatory and respiratory disturbances.

Co-administration of dietary lipids or pharmaceutical lipid excipients has the potential to substantially increase the bioavailability to orally administered Cannabis and Cannabis-based medicines by 2.5-3-fold. Sesame oil, which is mostly composed of long-chain triglycerides (LCT) has been used. Glycocholate has also been used. The carrier oil may include Panakeia™ or any hemp seed derived The bioavailability will be enhanced with product emulsification, co-crystals, solid salts using maleic acid or nanoparticles This Product can be modified with additional additions that can enhance the beneficial effect including Echinacea, PEA, Melaleuca cajuputi Oil, resveratrol or liverwort; cannabidiol (CBD) which has additional endocannabinoid binding, etc.

Proportions of CBD (isolated or full spectrum) may be added into the Panakeia™ extract for additional benefit and/or synergy as another variation.

This Product can also be modified with additional additives with other natural plant products that enhance other mechanism of effect, including fungi, algae.

This Product can also be modified with additional additives including Lactobacillus to facilitate gut health for oral ingestion.

This Product can be modified with deletions of certain terpenes, for example, Guaiol (pro-anxiety and stimulant) which can improve the odor, taste or flavor of the patented product. Specific terpenes may be removed by affinity binding to bound to specific receptors, antibodies, affibodies, adnectins, affimers, affitins, anticalins, atrimers, fynomers, armadillo repeat protein molecules, Kunitz domain inhibitor molecules, knottins, designed ankyrin repeat proteins, etc.

Non-specific or less specific affinity separation may be employed, both to remove specific terpenes or families of terpenes (i.e., β-myrcene), or to concentrate the desired terpenes, such as resin bears, polysaccharide and modified polysaccharide gels (e.g., Sepharose, alginates), and other known separation techniques.

This Product can be further modified with deletions of certain terpenes, phytoestrogens (apigenin) or other Cannabis plant containing compounds that can potentially result in adverse events, side effects and intolerance. For example, apigenin may be selectively reduced by affinity separation techniques, based on its binding to estrogen receptors, or other specific binding biomolecules such as antigen-binding fragments (Fab) or other known separation techniques.

This Product can be further modified with deletions of Chlorophyll.

This Product can be used as an additive to other food and beverages that enhance the nutritional value include inhalant (vaporized or aerosolized), alcoholic or nonalcoholic beverages, snacks, tinctures, topical applications, chewables, chocolates, coffee, toppings and spices, sweeteners, cakes, popcorn and desserts.

This Product for vaporizing will be optimized for the resin oil, burn temperature, rise time and quantity taken, taking into account therapeutic dosing and its intervals of administration and safety of the carrier products into the alveoli.

This Product has intended mechanism of effect that can enhance the care and treatment of Covid-19 particularly with effects on the respiratory tract, which is a serious disease associated with morbidity that has substantial impact on day-to-day functioning.

CBG is classified as one of the major cannabinoids, as a phenolic (acid based) terpene oil, which is then combined with several plant derived additives to enhance effect, absorption and flavor, to form the novel proprietary food product, PECSA™ (the Bazelet Health System company's proprietary Plant-based EndoCannabinoid System Activating compound).

There is a hypothesized "entourage" effect of the combination of all cannabinoids (with or without THC) taken as a "spectrum" of ingredients has a greater effect that each individual cannabinoid alone for a therapeutic response. In addition, the route of administration as well as the dose intervals, may contribute to the clinical effect, such that vaporized CBG potentially may have minimal psychotropic properties (predictably, topical use would have a negligible effect) in some preparations, due to a more rapid onset and shorter duration of effect. The most notable benefit of Cannabis in any form is its safety, with no reports of lethal overdose with any of the cannabinoids.

The technology may be used to co-extract other botanical additives (hops, mint, Echinacea, etc.) which allows for unique formulations which provide full spectrum biologic agents, in natural proportions (with possible modifications by selective addition of components, and selective removal of undesired components), as well as the capacity to process other botanicals as stand-alone products.

Standardization of Panakeia Extract

In order to standardize the full spectrum CBG product, which has natural variability due to the species variation, growing conditions, harvesting, post-harvest conditions and drying, etc., a target mixture may be defined, and additional botanicals added to the Cannabis, or the complementary botanical extracts added to the extracted product. In either case, an assay is performed of the Panakeia material, to determine its CBG potency, terpene profile, and other target components. A database is then accessed, using linear programming, to cost efficiently find available botanical materials that, when extracted, will complement the Panakeia extract to achieve the target profile. In some cases, purified terpenes and terpenoids may be added to the extract, though preferably the product represents a raw extract from combined botanicals or combined extracts of raw botanicals. Greenhouse cultivation may be used as an effective means of maintaining standardization in some of the patent application claims.

An oil, concentrate, or extract is a product derived from Cannabis flower (or other botanicals) that is processed into a concentrated form, but each type of Cannabis oil is unique.

*Cannabis* oils are efficient, with less product required to achieve the desired effect. Extracts are refined. Essential oils and cannabinoids are separated from plant material to create a smooth *Panakeia* oil (full spectrum CBG, which includes other *Cannabis* terpenes and flavonoids), which are products that are formulated as a tincture (sublingual), capsule form (oral), topical or vaporizer (inhaled). A tincture is a liquid concentrate procured through alcohol extraction, which pulls out many of the plant's beneficial cannabinoids.

Live resin and other products labeled "live" (like live rosin) are concentrates that have been extracted before the *Cannabis* plant has been dried or cured. Terpenes, the aromatic compounds that give *Cannabis* its flavor, are so volatile, they're known to dissipate even at room temperature. Working with a freshly harvested plant gives extractors the best chance of capturing robust terpenes and flavors. To preserve these fragile terpene profiles, extractors may freeze and store freshly cut *Cannabis* until it's ready to be extracted.

A *Cannabis* concentrate can either be full spectrum, containing a vast array of complex combinations of cannabinoids and terpenes in the natural ratio, or an isolate, which is a precise formulation of a single ingredient in crystalline or powdered form. The terpene fraction, acts as a naturally occurring solvent. Over time, the solid cannabinoid molecules separate from the liquid terpenes and leave behind rigid cannabinoid structures that look similar to quartz. Sauce, sometimes called "terp sauce" or "the terpene fraction," refers to a runny, terpene-rich concentrate. As cannabinoids and terpenes separate from one another, extractors are left with solid cannabinoid compounds and a watery mixture of the aromatic terpenes. Sometimes sauce products are labeled with the acronym HTFSE, short for high-terpene full-spectrum extract. That means it's a terpene-rich concentrate that still maintains a well-rounded cannabinoid profile. While hemp oil is federally legal (<0.3% THC), and is widely advertised online, and hemp Panekia™ oil contains full spectrum CBG (but not THC or CBD), whereas *Cannabis* (indica)-derived CBD is only available at a state dispensary and is federally illegal. The terpene content and specific molecules may be adjusted to provide a fragrance and flavor that is appealing, and not overwhelming to the consumer.

A raw or crude extract may still contain many terpenes, fats, and lipids. However, it can be further refined by distillation. Good, clean distillate usually tests up to 90% or higher in total cannabinoids. Pure distillate is virtually flavorless and is popularly used as a base ingredient for other *Cannabis* products like edibles and topical applications.

*Cannabis* wax is a soft, opaque concentrate that can vary in appearance, texture, and color, as determined by heat, moisture, chemical composition, and purging process. Many waxes are the result of agitating a raw extract into a whipped, aerated consistency.

The extracted oil may be tested by a laboratory for certification that this plant product is free from pathogen heavy metal or organic chemical contamination. Testing for contaminants is typically performed by a certified laboratory using liquid or gas chromatography with mass spectroscopy, and the final product includes but is not limited to those analytes listed below and their acceptable limits as primarily determined by the New York State Department of Health.

Analytes: *E. coli, Pseudomonas* (for products to be vaporized), *Salmonella* species, *Enterococcus* species, Bile tolerant gram negative bacteria (specifically including *Klebsiella* species), *Clostridium botulinum, Aspergillus* species, *Mucor* species, *Penicillium* species, Thermophilic Actinomycetes species, Aflatoxins B1, B2, G1, G2, Ochratoxin A, Antimony, Arsenic, Cadmium, Chromium, Copper, Lead, Nickel, Zinc, Manganese (not mandated by NYS), Mercury, any pesticide used during production of the hemp product (Azadirachtin, Myclobutanil, Piperonyl butoxide, and Pyrethrin Mix: Cinerin I, Jasmolin I, Pyrethrin I), or any growth regulator (Indole-3-butyric acid (IBA)) used during production of the hemp product. For heavy metals, testing will be done at both the growing (flower) and processing (oil) stages.

Additional additives to enhance absorption, improve biologic effect and work synergistically with full spectrum CBG may include black and white pepper.

A number of natural biologic additives are contemplated, including fungi, algae, and plant derived oils.

The integration of Algae, Fungi, and other beneficial soil microorganisms in tandem with *Cannabis sativa* L. may be useful.

The invention is safe, effective, and affordable, and healthy ingredient that can be incorporated into a wide range of foods, beverages, cosmetics, medicines, drugs and OTC products. PECSA can enhance the efficacy of other Active Pharmaceutical Ingredients, Drugs, foods and beverages. Other applications include inhalants.

The CBG oil or extract may be administered with an absorption enhancer, such as black pepper (*Piper Nigrum*) containing (E)-β-caryophyllene [(E)-BCP](www.ncbi.nlm.nih.gov/pmc/articles/PMC2449371/) and piperine, and/or white pepper.

It is therefore an object to provide a method of treating a human severe acute respiratory coronavirus infection, comprising administering a pharmaceutically acceptable full spectrum extract of a plant of genus *Cannabis* comprising at least 5% by weight cannabigerol, *Cannabis* terpenes, and *Cannabis* flavonoids, to a person having the human severe acute respiratory coronavirus infection.

It is also an object to provide a method of treating a human severe acute respiratory coronavirus infection, comprising administering a pharmaceutically acceptable cannabinoid formulation, comprising cannabigerol, in combination with limonene, linalool, pinene, humulene, β-caryophylline, bisabolene, terpinolene, myrcene, and substantially without cannabidiol and tetrahydrocannabinol, to a person having the human severe acute respiratory coronavirus infection.

It is a further object to provide a full spectrum extract of a plant of genus *Cannabis* comprising at least 5% by weight cannabigerol, *Cannabis* terpenes, and *Cannabis* flavonoids, substantially without cannabidiol, tetrahydrocannabinol, and extraction solvent residue.

The cannabinoid composition may be provided in a pharmaceutically acceptable inhalable formulation for efficacious prophylaxis or treatment of respiratory coronavirus infection in humans.

It is another object to provide a cannabinoid composition, comprising: cannabigerol, in combination with limonene, linalool, pinene, humulene, β-caryophylline, bisabolene, terpinolene, myrcene, and substantially without cannabidiol and tetrahydrocannabinol; at least one enhancer selected from the group consisting of curcumin, resveratrol, quercitin, and piperine; and at least one N-alkylamide.

It is also an object to provide a full spectrum cannabinoid formulation, comprising: an extract of *Cannabis* plant comprising at least 7% by weight cannabigerol and cannibigerolic acid, with natural *Cannabis* terpenes and flavonoids comprising components having a boiling point of less than 125 C, and lacking detectable cannabidiol and tetrahydrocannabinol, and substantially without extraction solvent residual.

The composition may further comprise at least one absorption enhancer selected from the group consisting of curcumin, resveratrol, quercitin, and piperine.

The composition may further comprise at least one N-alkylamide.

The cannabinoid composition may be provided in a pharmaceutically acceptable formulation for efficacious down regulation of Transmembrane Serine Protease 2 (TMPRSS2) expression in lung cells.

The cannabinoid composition may be provided in a pharmaceutically acceptable formulation for efficacious down regulation of angiotensin-converting enzyme 2 (ACE2) expression in lung cells.

The cannabinoid composition may be provided in a pharmaceutically acceptable formulation for efficacious reduction of interleukin (IL)-6.

The cannabinoid composition may be provided in a pharmaceutically acceptable formulation for efficacious reduction of interleukin (IL)-8.

The cannabinoid composition may be provided in a pharmaceutically acceptable formulation for efficacious reduction of interleukin (IL)-1β.

The cannabinoid composition may be provided in a pharmaceutically acceptable formulation for efficacious reduction of TNF-α.

The cannabinoid composition may be provided in a pharmaceutically acceptable formulation for efficacious reduction of IFN-γ.

The cannabinoid composition may be provided in a pharmaceutically acceptable formulation for efficacious reduction of PPARγ.

The cannabinoid composition may be provided in a pharmaceutically acceptable formulation for efficacious reduction of pro-inflammatory cytokines in lung tissue in response to SARS-Cov2 infection.

The cannabinoid composition may be provided in a pharmaceutically acceptable inhalant formulation.

The cannabinoid composition or formulation may further comprise *Cordyceps sinensis* extract.

It is also an object to provide a method of processing an extract of a plant of genus *Cannabis* comprising contacting the extract with a separate phase having phytoestrogen binding molecules, to thereby sequester the phytoestrogens in the separate phase and form a phytoestrogen-depleted extract. The extract may be a full spectrum extract, and the phytoestrogen-depleted extract is substantially a full spectrum extract depleted of phytoestrogens. The extract may comprise at least 5% by weight cannabigerol. The extract may be a full spectrum extract, and the phytoestrogen-depleted extract is substantially a full spectrum extract depleted of phytoestrogens.

It is a further object to provide a method of processing an extract of a plant of genus *Cannabis* comprising contacting the extract with a separate phase having a biomolecular receptor or high-affinity binding peptide for a cannabinoid, terpene or flavonoid component, to thereby sequester the cannabinoid, terpene or flavonoid component bound to the biomolecular receptor or high-affinity binding peptide in the separate phase and form a depleted extract.

It is also an object to provide a method of treating or preventing a human having severe acute respiratory syndrome (SARS) resulting from a coronavirus infection (COVID), comprising administering a pharmaceutically acceptable full spectrum or broad spectrum extract of a plant of genus *Cannabis* comprising at least 5% by weight of at least one of cannabigerol, cannabigerol acid, cannabigerovarin, and cannabigerovarin acid; together with *Cannabis* terpenes and *Cannabis* flavonoids, to a person having the human severe acute respiratory syndrome.

It is a further object to provide a full or broad spectrum extract of a plant of genus *Cannabis* comprising: at least 5% by weight of a cannabinoid selected from the group consisting of at least one of cannabigerol, cannabigerol acid, cannabigerovarin, and cannabigerovarin acid, predominantly in an acid form; *Cannabis* terpenes; and *Cannabis* flavonoids; substantially without cannabidiol, tetrahydrocannabinol.

It is a still further object to provide a cannabinoid composition, comprising: at least one of cannabigerol, cannabigerol acid, cannabigerovarin, and cannabigerovarin acid, substantially without cannabidiol and tetrahydrocannabinol; and at least one endocannabinoid.

The depleted extract may be substantially without cannabidiol, tetrahydrocannabinol, and extraction solvent residue.

It is another object to provide a *Cannabis* extract, having affinity depletion of phytoestrogen components or other receptor or high affinity binding peptide specific components.

BRIEF DESCRIPTION OF THE DRAWINGS

FIG. 1 shows a biochemical pathway for synthesis of cannabigerol.

FIG. 2 shows biochemical pathways for synthesis of other cannabinoids from cannabigerol.

FIG. 3 shows biochemical pathways for synthesis of various terpenes.

DETAILED DESCRIPTION OF THE PREFERRED EMBODIMENTS

The full spectrum extract from the *Panakeia* plant with any additional modifications, including adding or deleting natural ingredients, changing concentrations has been designated as Bazelet Health Systems, Inc. proprietary Plant-based EndoCannabinoid System Activating compound (PECSA™) which is comprises all of the naturally occurring cannabinoids and other non-cannabinoid components that are co-extracted with the at least one CBGA (and to a lesser extent, CBGVA) or decarboxylated derivative-type compound (CBG, and to a lesser extent CBGV). In other PECSA™ iterations, the *Panakeia*™ "full spectrum" CBG extract is concentrated, with other additive, substitutions or deletions, or combined with other natural ingredients to enhance effect, absorption and flavor, to form the novel proprietary food product. In one embodiment. The PECSA™ extract will contain primarily CBGA, or converted in some proportion to CBG, or be enriched from products from the *Panakeia*™ plant including higher concentrations of CBG. In other words, the extract contains a greater proportion of the total cannabinoid content as CBG as compared to the cannabinoid composition from which the extract was prepared primarily by purifying the plant extract further after extraction to select specifically for CBG (through patented methods for the exact extraction parameters for optimization of product yield). The therapeutic effects of PECSA™ are due to the combined ingredients as a synergistic or entourage effect, with CBGA/CBG as the primary ingredients. Although they are similar compounds, CBGA (an acid) and CBG, may have different therapeutic applications and benefits than if they were administered as an individual component.

Conditions for which Panakeia full spectrum extract and/or PECSA™ may improve the management of serious diseases or conditions associated with morbidity that has substantial impact on day-to-day functioning: pain (somatic-musculoskeletal, visceral, neuropathic and nociceptive), mood, anxiety, PTSD and sleep disorders, neurodegenerative disease (including dementias, Huntington and Parkinson disease), ischemic disease, brain injury (including acquired) or damage, age related inflammatory or autoimmune disease, cachexia, nausea and vomiting, glaucoma, movement disorders, rheumatoid arthritis, bone disease and osteoporosis, asthma, allergy, psoriasis, Inflammatory bowel disease (Crohn's disease), systemic lupus erythematosus, hypertension, diabetes, neurogenic bladder dysfunction, cancer, nephritis and renal ischemia, pelvic pain (including endometriosis), periodontal disease and gingivitis, skin conditions (including acne and eczema) as well as respiratory illness (i.e. Covid-19).

The PECSA™ full spectrum extract (with additional modification, including additives or deletions) may be provided in dosage forms, e.g., oral unit dosage forms, providing a CBG/CBGA content up to 1200 mg/day, and may be used for the management of many serious conditions or diseases as discussed above.

Panakeia™ Extraction (Herbolea Process, or Equivalent)

Herbolea Biotech SRL also has an enzyme-assisted lipid-based extraction technology, see U.S. Pat. No. 10,973,864. The method for preparing a cannabinoid concentrate comprises of the following steps: providing a lipid extract containing cannabinoid acids of at least 20% by weight percent on total cannabinoids weight.

In an exemplary process, to extract the phytocannabinoids or terpenes containing plant material such as hemp or Cannabis can be fresh (preferred) or dried. The Cannabis flower is first milled and comminuted involving a micronization step of the plant material occurs is to reduce particle sizes and increase the surface of material reacting in the following step. All parts of the plant, such as stems (with high lignin content) and buds are usually trimmed, and it can be discarded recycled for organic fertilizer. Ideally, a well harvested sativa L will have more abundant flowers, with less hemp seeds, and an average plant weight is 450 gm (wet) or 295 gm (dry). Milling can be performed on wet or dried material.

Distilled water is added (if the plant biomass is too dry), along with enzymes (usually cellulose) and carrier oil (often sunflower) are added to the plant material to form a homogeneous mixture or slurry; temperature (usually <55 C) and pH (usually 4.5). It is then mixed with hydrolyzing enzymes (5-8%, based on the plant appearance, with lower amount if the plant has robust flowers), with higher concentrations required to dissolve the plant matrix, using cellulitic enzymes (primarily cellulase, hemicellulase, etc.) are added to the plant material to form an aqueous slurry. Conditions might vary according to the specific enzyme or enzymatic cocktail used to dissolve the plant material including lignin and chlorophyll. The mixture may be agitated through stirring or other agitation methods for at least 30 min to let the enzymes degrade the plant material. Ultrasound/sonication or microwaves or steam explosion may be used before or after adding enzymes to the mixture to reduce the time necessary to achieve plant material dissolution and high cannabinoids lipid-extraction yield. Water to plant ratio is critical to achieve plant material degradation through enzymatic activity; newly harvested plant material can also be used directly, avoiding pre-drying step during which degradation and/or losses of phytocannabinoids and terpenes, especially monoterpenes, can occur; in such case, little to no water can be used. Lipids can be added to the mixture any time without significantly modifying enzymatic activity; a suitable lipids-to-plant material ratio to obtain high phytocannabinoid content and high extraction yield (at least 70%, or more preferably at least 90%). The mixture obtained is then separated via density separation (i.e., centrifugation usually 2300 rotations per minute-rpm for 30 seconds) or pressing (French press) and/or filtration to recover a lipid fraction highly enriched with cannabinoids and waxes free. In case of lipid extract obtained from Cannabis, the extract can be optionally heated at higher temperatures to decarboxylate acid form cannabinoids (mainly CBGA) to the desired extent.

The use of enzymes drastically enhances the lipid-based extraction of phytocannabinoids and terpenes/terpenoids, including volatile monoterpenes, allowing for a significant reduction of the lipid solvent-to-plant material ratio (i.e., 10-15 times compared to traditional Romano-Hazekamp method), while still achieving a high cannabinoids extraction yield (i.e., 90%), hence the possibility to safely and directly obtain a waxes-free lipid extract, having a phytocannabinoid and terpene content appropriate for and compatible with therapeutic applications dosage, where the terpene fingerprint of the plant material is faithfully reproduced (the proportion of cannabinoids, terpenes and other phytochemicals is preserved, so CBGA remain the predominant contents). Furthermore, it has also been found that the use of enzymes dramatically increases the stability of phytocannabinoids and terpenes/terpenoids in the extract, allowing to achieve a shelf-life appropriate for and compatible with pharmaceutical applications with no addition of preservatives. In this step cannabinoids and terpenes are released. The pH of the mixture can be adjusted for optimal enzymatic activity (i.e., pH=4.5). Temperature is set in the range of 30-55° C.

In addition to that, the solid fraction generated by the process shows a phytocannabinoids content significantly reduced. In the case of hemp seeds (if using Panakeia™, low concentrations of CBGA, and if using standard hemp plants, low concentrations of CBGA, CBD or CBDA, but also contain a protein rich "cake"), the cannabinoids content was greatly reduced compared to mechanical expeller, therefore making the protein-rich solid fraction compliant with safety guidelines for feed and food product applications. Panakeia™ hemp seed, if utilized for the carrier oil may be derived with specific plants harvested for the seed yield and have a different terpene distribution. The extraction process may include the entire Panakeia™ plant biomass; or the Panakeia™ seeds separated and the seed oil extracted with an oil yield of about 25%.

A nonpolar solvent (usually water) is then added to facilitate the extraction and direct infusion, and the carrier oil helps solubilize the active ingredients (cannabinoids and terpenes), which yields a full spectrum extract, (if scaled for 100 kg oil which is >90% efficient), known as bioherbolysis. This allows higher efficiency without concentrating at first step, giving subsequent flexibility to further concentrate at higher levels of CBGA spectrum. The mixture is then placed in a centrifuge in which the slurry is centrifuged at high speeds (>4000 rpm, usually 4500 rpm). The lightest phase contains non-polar compounds (cannabinoids 25%, terpenes 0.1%) solubilized in oil, followed by a higher density aqueous phase containing water soluble compounds (including carbohydrates), and then these fractions are separated using an ultra-filtration technique.

Hydrocan Process

Herbolea also developed a solvent-less extraction technology. See, WO2021037343A1.

The oil extract (of lightest density) is then distilled with specific temperature (maximum evaporation temperatures are between 120° C. to 260° C.) and vacuum specifications (minimum pressures of 0.001-0.04 millibarr-mbar, usually 0.023 mbar), and separating from said vacuum distillation a distillate containing the cannabinoid concentrate to form a cannabinoid acid solid distillate known as Hydrocan (without terpenes or other phytochemicals), which can be in cake form. This distillate is then mixed and pH balanced with an aqueous solution and filtered, in which a decolorized cannabinoids product (almost 10× the concentration of the full spectrum lipid extract) are selectively extracted with >90% efficiency, known as Distillac (if scaled for 10.1 Kg Concentrate of CBGA). It can be further filtered (using polishing and charcoal) to reduce pathogens (bacteria, algae and fungi) as well as produce pure crystallized (<80% efficiency) CBGA. This also contains other cannabinoids, but not THCA, THCVA, THC, THCV, CBDA, CBDVA, CBD, CBDV. CBGA, in powder form, predictably has a longer shelf life than decarboxylated CBG, if stored at room temperature or below, no light exposure and vacuum packed. It can then be converted to CBG and combined with other phytochemicals for the full spectrum Panakeia™ extract or PECSA™ based products based on subsequent distillations to incorporate or eliminate any terpenes, which can enhance the taste, odor or flavor.

A preferred protocol for all of the extraction of the full spectrum CBGA/CBG product are based on patented extraction from Herbolea, though modified for the present application to Panakeia.

The lipid extract containing cannabinoids may be obtained by putting in contact with a biological material containing cannabinoids with liquid paraffin, which can selectively extract cannabinoids in their acid forms more efficiently than neutral forms. Therefore, if liquid paraffin is utilized to obtain a lipid extract, it is possible to obtain a distillate, having a higher purity, even if the cannabinoids in the starting biological material have gone through partial decarboxylation. Where decarboxylation is not a primary concern, the paraffin is not necessary.

The method may also be described by obtaining the lipid extract containing cannabinoids from a plant material containing cannabinoids by means of the steps of: a. comminuting a biological material containing cannabinoids; b. mixing the comminuted plant material with enzymes to form a mixture to which water and lipids or solvents are optionally added; c. agitating the mixture at a temperature range of 1 to 80° C.; and d. separating the mixture into a lipid phase, an aqueous phase, and a solid phase; wherein the lipid phase comprises the lipid extract.

Enzymes may also be used to process the plant material, including one or more enzymes independently selected from the group consisting of Oxidoreductases, Transferases, Hydrolases, Lyases, Isomerases, and Ligases, cellulase, hemicellulase, xylanase, glucanase, β-glucanase, pectinase, glucuronyltransferase, lipase, amylase, alpha-amylase, beta-amylase, phospholipase, arabanase, galacto-mannanase, β-mannanase, protease and phytase. In an embodiment, said enzyme is cellulase. In another embodiment, said enzyme is beta-glucosidase. In another embodiment, said enzyme is hemicellulase. In another embodiment, said enzyme is xylanase. In yet another embodiment, said enzyme is glucanase. In yet another embodiment, said enzyme is pectinase. In still another embodiment, said enzyme is amylase. In yet another embodiment, said enzyme is lipase or phospholipase. In still another embodiment, said enzyme is glucuronosyltransferase or alcohol dehydrogenase. In yet another embodiment, said enzyme is arabinanase. In still another embodiment, said enzyme is phytase. In a further embodiment, said enzyme is protease. Preferably, said enzyme is a mix or a cocktail of cellulase, β-glucanase, pectinase, β-mannanase, alpha-amylase and protease; wherein the amount of enzyme is 3% of the weight of plant material; and the pH of the mixture is adjusted to pH 5.6 with monohydrate citric acid.

Preferably, the cannabinoid concentrate comprises less than 1 ppm of organic solvent selected from a group consisting of Acetone, Benzene, Butane, Chloroform, Cyclohexane, Dichloromethane, Ethanol, Ethyl Acetate, Ethylbenzene, Heptane, Hexane, Isobutane, Isopropanol, Methanol, Pentane, Propane, Toluene, m-Xylene, o-Xylene, p-Xyleneheptane or a mixture thereof.

Cannabis Plant Harvesting

The "Panakeia" Cannabis sativa L. plant is cultivated from a seed, and the seedling is grown in a climate-controlled environment with temperature ranges from 45-100° F., and humidity that ranges from 20-100%, with sunlight or simulated sunlight for >18 hours per day, and with fertilized soil that is pesticide and herbicide free. Cannabis sativa L. rapidly sequesters carbon and bolsters soil systems. It is estimated that an average Panekeia™ plant weighs 450 gm (wet), with a required growing surface area of 2 ft$^2$ for indoor growing environments and outdoor growing environments of 2,000-3,500 plants per acre are estimated.

Current studies have shown the mineral accumulating capabilities of Cannabis sativa L. as a "cover crop" and its potential as a promising method of bioremediation. Cannabis sativa L. taproot and root-ball, aids in the structuring of soils and retention of water which prevents desertification, while bolstering soil systems and aiding in the global effort to reduce carbon emissions and creating habitat for the evolution and expansion of complex soil food webs. This makes Panakeia™ Cannabis sativa L. safe for use in water conservation, harvesting and improving soil structure. A "hemp seed cake" has shown to be optimal for livestock feed, increasing overall health, quality of meat and reducing methane off gassing by 10%. Oil seeds contain 25-35% lipids with unique and perfectly balanced fatty acid profiles, characterized by an over 80% amount of polyunsaturated fatty acids, with the essential fatty acids of ratio (omega 3/omega 6 as 1:4), as suggested for optimal human nutrition.

The biomass produced in these areas will be the future industrial feedstock of the globe. High in alpha cellulose, hemi cellulose and lignin, micronized hemp herd can be utilized for its multifaceted attributes and applications including fabrication of unique graphene-like nanomaterial, or as a building material, "hempcrete", consisting of two major compounds (Hemp shiv, and a Lime-based binder for good thermal and insulation properties.

Typically, the Cannabis plants are traditionally hung upside down to dry from a "clothes line" while blocking most of the light with a sensor monitored climate controlled: 70° F.±10, humidity: 50%±5 and good air flow, using a fan (although this may lower humidity, but one needs to avoid over-drying). There may be optimization for altitude. For smaller components, an herb dryer has been used to set any loose buds or smaller branches on. As the Cannabis dries, the CBGA found in the kiefs and buds may spontaneously convert to CBG. The buds that are dried too quickly will experience a more significant decomposition, with less concentration of cannabinoids than those that are allowed to dry more slowly.

Curing is essentially a continuation of the drying process, but in a slower, controlled environment—such as in sealed mason jars—and occurs for up to two months. Meaning, once the *Cannabis* is dry, it may still need time for CBGA spontaneous conversion. Proper curing stops the degradation process before volatile compounds like terpenes and cannabinoids evaporate or transform into less favorable compounds. Additionally, cannabinoid synthesis (the process of creating those valuable chemicals) continues to take place even after harvest. During the curing process, bacteria work to break down the chlorophyll in the plant material. Chlorophyll is what makes the plants nice and green in color, but also contributes to a harsh smoking experience. The containers are stored in a dark, temperate place, with occasional burping to allow oxygen into the jar and release moisture or other off-gassing substances.

An oil, concentrate, or extract is any product derived from *Cannabis* flower that is processed into a concentrated form, but each type of *Cannabis* oil is unique. *Cannabis* oils are efficient, with less product required to achieve the desired experience. Extracts are refined. Essential oils and cannabinoids are separated from plant material to create a smooth *Cannabis* full spectrum oil, which are products that are sold as a tincture (sublingual), capsule form (oral), topical or vaporizer (inhaled). A tincture is a liquid concentrate procured through alcohol extraction, which pulls out many of the plant's beneficial cannabinoids.

Other Cannabinoid Extraction Processes (can be Applied to *Panakeia*™)

Various processes to extract phytocannabinoids and/or terpenes/terpenoids have been developed. The following major extraction processes are known:

Cold pressing for producing hemp seed oil. Hemp seed oil is rich in nutrients and is a good addition to any diet, but only contains small amounts of cannabinoids (<2%, in the case of industrial hemp), as it is made from just the seeds of the plant. Hemp seed oil can certainly be added to CBD supplements as a base for these products. However, cold pressing is not useful to produce an oil high in cannabinoids, as cannabinoids are mostly contained in the stalks and buds that cannot be directly processed by a normal press or expeller.

The Rick Simpson Method for *Cannabis* Oil is a popular extraction method for extracting CBD oil, which uses petroleum or naphtha as solvents. This method, although efficient in extracting the active compounds from the *Cannabis* plant (mostly done with plants high in THC), usually leads to products that have a lower concentration of terpenoids and other cannabinoids such as CBD, while effectively yielding higher concentrations of THC. The main drawback of such method is that residuals from the solvents may remain and potentially interfere with one's immune function as described by Romano and Hazekamp ("*Cannabis* Oil: chemical evaluation of an upcoming *Cannabis*-based medicine", 2013).

Extraction with ethanol can be used for extracting the full range of cannabinoids from the *Cannabis* plant, and it is safer than the Rick Simpson method. On the other hand, ethanol has a low selectivity, and it extracts undesired chlorophyll and waxes, so the final product has an unpleasant taste. Chlorophyll can be removed by filtering the extract, but this additional step also removes a significant proportion of the cannabinoids, therefore leading to less potent extract. Furthermore, stability of cannabinoids as well as N-alkylamides in ethanol extracts is low (Citti et al., 2015 and Spelman, 2009).

Extraction with Sonication/ultrasonic waves: C. Da Porto, (Ultrasound-assisted extraction of volatile compounds from industrial *Cannabis sativa* L. inflorescences, 2014) describes procedures for extracting THC and terpenes from hemp by using ultrasonic waves. The use of ultrasonic increased the extraction of THC, but after 15 min of treatment the overall efficiency of extraction was still not satisfactory.

Super Critical $CO_2$ extraction (U.S. Pat. No. 9,186,386 B2, U.S. Pat. No. 6,403,126 B1) can be an efficient method to obtain a highly enriched cannabinoids oil (>60%). At such level of concentration, the product is not directly consumed but it is diluted with vegetable oils such as olive oil to reach 3-5%. The method uses safe solvents, but it requires complex equipment and expertise, is energy demanding, and the product obtained is very expensive. Additionally, it requires the initial *Cannabis* material to be dried, adding a step that is time consuming and has negative effects on important compounds such as volatile monoterpenes. Furthermore, the process itself is subject to significant losses in terms of monoterpenes extraction yield, hindering the entourage effect of the extracts. Additionally, it has high selectivity for toxic components which might be present in pesticides, therefore a risk associated to their presence in concentrated form in the final product might be present. Moreover, the product of SC—$CO_2$ extraction may have a significantly different chemotypic fingerprint from that of *Cannabis* flower (Sexton, 2017). Finally, the stability of cannabinoids extracted with $CO_2$ diluted in olive oil is inferior to that obtained with their direct extraction in olive oil as described by Cannazza ("Medicinal *Cannabis*: Principal cannabinoids concentration and their stability evaluated by a high-performance liquid chromatography coupled with diode array and quadrupole time of flight mass spectrometry method", 2016).

Winterization may be performed after supercritical fluid extraction and encompasses the use of ethanol or butane at low temperatures (U.S. Pat. No. 9,186,386 B2, U.S. Pat. No. 6,403,126 B1). Such process presents several drawbacks such as the high investment required, the need for highly skilled technicians to utilize complex equipment, the use of flammable and harmful organic solvents to winterize the crude extract, the high energy consumption. It is very challenging to completely remove organic solvents used in combination with $CO_2$ during the extraction step or to remove chlorophyll in the winterization step. The technical challenge to overcome has led policymakers to set content limits for organic solvents, some of which are known cancerogenic compounds, as high as 5,000 ppm (source Health Canada). Additionally, supercritical $CO_2$ has high selectivity for toxic components which might be present in pesticides, therefore a risk associated to their presence in concentrated form in the final product might be present. Furthermore, as heat is required to dry the biomass and remove the solvents as well as it is generated through the $CO_2$ extraction step, it is very difficult to well preserve heat-sensitive acidic forms that can decarboxylate. The cannabinoids content achieved with such process is not sufficiently high to go directly into a crystallization step. An intermediate distillation step is often required. Finally, supercritical $CO_2$ cannot extract with the same efficiency acidic forms of cannabinoids due to higher molecular weight compared to the neutral forms. All these aspects make the whole process not an ideal option to extract and concentrate acidic forms of cannabinoids. In the vaping sector, for instance, the possibility to utilize concentrates having a high content of CBDA instead of CBD is helpful to avoid the formation of crystals in the vaping cartridges.

A more recent alternative technique is represented by cryogenic-ethanol, a process in which a biomass that has been previously dried is extracted at very low temperatures (−40° C.) to avoid extraction of chlorophyll and waxes into the solvent. The cannabinoids-enriched ethanol solution is then evaporated to recover the solvent. Such activity is energy intensive, and it can be very time consuming, considering the large volumes of solvents to be evaporated (up to 20 times biomass weight). Furthermore, the use of organic solvents inherently results in safety, health and environmental issues.

As to the cannabinoid isolates, today CBFD crystals are obtained from concentrates generated with one of the techniques earlier described by means of purification steps, such as distillation followed by chromatography, and then a crystallization step by means of eptane or exane (GB 2393182, WO2016153347A1). Chromatography is required to eliminate impurities before entering the crystallization step, especially if the starting biomass contain low level of cannabinoids such as hemp. Chromatography can be a very time consuming and costly process and presents some limitations in scaling up. Furthermore, chromatographic purification methods such as flash chromatography can have a high environmental impact since they typically involve large quantities of harmful or toxic solvents run at high flow rates.

Extraction with microwaves. Koturevic et al. (A rapid method for the extraction of cannabinoids from *Cannabis sativa* using microwave heating technique, 2014) described the possibility to use microwaves to assist the extraction of cannabinoids by organic solvents. Few organizations such as New Brunswick Innovation Research Chair in Medical Technologies (NBIRC), Radient Technologies and Scientus Pharma announced partnerships with *Cannabis* producers to develop microwaves-assisted cannabinoids extraction methods. Technical data are still limited, nevertheless technical limitations might derive from the step of separation of solvent from plant material, the recovery of solvent that remains adsorbed in the vegetable matrix, the ratio solvent to plant material and, finally, the possibility to reach high concentration in extracts in case non-volatile solvents are used (i.e., vegetable oils).

Romano-Hazekamp method is based on the extraction of cannabinoids from pre-heated, dried *Cannabis* inflorescences using vegetable oils (i.e., olive oil) as solvents. The method can be used for extracting the full range of cannabinoids from the *Cannabis* plant and it has the advantage of being very safe for consumption. Furthermore, it is considered the most sustainable process from an environmental point of view. (*Cannabis* Oil: chemical evaluation of an upcoming *Cannabis*-based medicine, Luigi L Romano, Arno Hazekamp, 2013). The drawbacks of this simple and increasingly popular method are that in order to achieve a satisfactory cannabinoids extraction yield, the extraction with vegetable oils has to take place at 98° C. for a prolonged time (1-2 h) and the quantity of oil to be added as solvent to the plant material is from 4 to 10 times the quantity of plant material, accordingly the level of cannabinoids content in the oil achievable is less than 1%, and more than 50% of volatile mono-terpenes is lost due to prolonged high temperature treatment. Finally, the stability of cannabinoids in the vegetable oil is very low, with a degradation in just two weeks of over 15% and over 20% for storage at 4° C. and ambient temperature respectively, as described by Pacifici ("Evaluation of cannabinoids concentration and stability in standardized preparations of *Cannabis* oil by ultra-high performance liquid chromatography tandem mass spectrometry", 2017).

WO 2018/130682 relates to an enzyme-assisted lipid-based extraction method for obtaining a lipid-soluble extract containing phytocannabinoids and/or terpenoids and/or terpenes. WO201 5070167 describes a method to purify cannabinoids by (i) contacting plant matter containing cannabinoids with a vegetable oil, (ii) heat the obtained lipid extract to fully decarboxylate the cannabinoids, (iii) distillate the decarboxylated cannabinoids.

Steam distilling and hydro-distillation are traditional methods for monoterpenes extraction. Steam distilling involves suspending a basket of herb above a vessel of boiling water. The steam passes through the perforated basket and penetrates the plant material. Only volatile compounds such as monoterpenes are soluble in the steam. Hydrodistillation is similar to steam distilling except that the herb is placed directly in the boiling water. The methods are not suitable for non-volatile substances such as cannabinoids or heavier terpene compounds.

Another "standard" CBD extraction process, which can also be used for *Panakeia*, but would likely convert CBGA into CBG during the process. However, if alternative hemp plants are processed with CBDA/CBD content including small amounts of TCHA/THC (<0.3%) were used, this could convert to CBD and THC, respectively, but this process cannot insure that at some point in the extraction/purification/concentration process that THC content will remain <0.3% in all steps, per Federal requirements:

step 1 comprises heating chopped *Cannabis* (2-3 mm) at 100-150° C. for sufficient time to allow decarboxylation.

(a) step 2 comprises $CO_2$ extraction using:

(b) a coarse powder (the particles are passed through a 3 mm mesh);

(c) a packing density of 0.3; and (d) super-critical conditions of 600 bar at 35° C. for 4 hours, although other combinations of temp and pressure ranging from 10-35° C. and 60-600 bar (both super critical and sub critical conditions) could, it is acknowledged, be used; and step 3 comprises conducting an ethanolic precipitation at −20° C. for 24 hours and removing the waxy material by filtration.

1 Biomass goes into knife crusher with milling (0.2 mm) of product.

2 Placed in Malaxer with T=55 C, pH=5, with distilled water, citric acid, enzymes and carrier oil to form slurry.

3 Placed in Decanter at T=40-55 C for separation, lipid cake extracted.

3 Placed in Clarifier Raw lipid extracts at T=40-55 C to form full spectrum oil.

An alternate process to increase hemp-CBD or *Panakeia* concentration is:

In mixing reactor, Full spectrum oil mixed with NaOH, water.

Placed in Centrifugal separator (6 cubic meters per hour), 60 meter head, to separate out alkaline water, discarding exhausted oil.

Alkaline water placed in static mixer for recovery using HCl, for acid solution for flocculation.

Acidic water further diluted with distilled neutral water, and filtrated with vibrating screen.

Maximum degradation of CBD when samples were stored at 37° C. for 30 days with average values up to 20%.

The effect of light was lower, but still significant with averages values up to 15% degradation after 30 days.

More commonly the *Panakeia* plant yield is approx. 6-8% total CBG which has no detectable THC or CBD by LC/MS certified lab.

Based on this analysis, there was no detectable other cannabinoids.

Terpene analysis by Molecular Science Corp:
trans-Caryophyllene 0.14 mg/g
Caryophyllene Oxide 0.03 mg/g
alpha-Humulene 0.03 mg/g
Eucalyptol 0.01 mg/g
cis-Nerolidol 0.01 mg/g
Limonene 0.01 mg/g
a-Pinene 0.01 mg/g
Borneol 0.01 mg/g A sample analysis performed by Crest Lab on recently harvested *Panakeia* reveals: water content 11.7%, with CBGA 6.8%, CBG 0.1%, without detectable THCA, THC, THCV, CBDA, CBD, CBDV, CBC, CBN, heavy metals, pesticides, mycotoxins, below threshold aerobic bacteria, fungi and yeast, bile tolerant gram negative, *E. coli, Salmonella*.

A sample analysis from Americanna Laboratories using a "dry" Panekeia 81,000 mg flower reveals 5.4% moisture, with 6.52% total of available CBG (based on detected CBGA=7.22% which converting by a factor of 0.877 to CBG, in addition to pure CBG=0.192%).

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A method of treating arthritis in a human in need thereof consisting essentially of administering to the human in need thereof:
   a) a *cannabis* extract which consists essentially of at least 5% of at least one of cannabigerol, cannabigerol acid, cannabigerovarin, and cannabigerovarin acid, wherein the *cannabis* extract lacks cannabidiol, cannabidolic acid, tetrahydrocannabinol, tetrahydrocannabinolic acid, cannabidivarin, cannabidivarin acid, tetrahydrocannabivarin, and tetrahydrocannabivarin acid;
   b) resveratrol;
   c) at least one of echinaea N-alkylamide and piperine; and
   d) eugenol.

2. The method according to claim 1, wherein the *cannabis* extract is from *Cannabis sativa*.

3. The method according to claim 1, wherein the resveratrol is trans-resveratrol.

4. The method according to claim 1, further consisting essentially of administering curcumin.

5. The method according to claim 1, further consisting essentially of administering quercetin.

6. The method according to claim 1, wherein the *echinacea* N-alkylamine is administered.

7. The method according to claim 1, wherein the piperine is administered.

8. The method according to claim 1, wherein both the *echinacea* N-alkylamine and the piperine are administered.

9. The method according to claim 1, wherein the *cannabis* extract consists essentially of at least 6.8% by weight cannibigerolic acid, with natural *cannabis* terpenes and flavonoids having a boiling point of less than 125° C.

10. A method of treating arthritis in a human in need thereof consisting essentially of administering to the human in need thereof:
    a *cannabis* extract which consists essentially of at least 5% of at least one of cannabigerol and cannabigerolic acid;
    resveratrol;
    at least one of echinaea N-alkylamide and piperine; and
    eugenol,
    wherein the *cannabis* extract lacks cannabidiol, cannabidolic acid, tetrahydrocannabinol, tetrahydrocannabinolic acid, cannabidivarin, cannabidivarin acid, tetrahydrocannabivarin, and tetrahydrocannabivarin acid.

11. The method according to claim 10, further consisting essentially of administering at least one of curcumin and quercetin.

12. The method according to claim 10, wherein the *echinacea* N-alkylamine is administered.

13. The method according to claim 10, wherein the piperine is administered.

14. The method according to claim 10, wherein both the *echinacea* N-alkylamine and the piperine are administered.

15. The method of claim 10, further consisting essentially of administering curcumin and quercetin.

16. The method according to claim 10, wherein the *cannabis* extract consists essentially of at least 6.8% by weight cannibigerolic acid, with natural *cannabis* terpene and flavonoid components having a boiling point of less than 125° C.

17. A method of treating arthritis in a human in need thereof consisting essentially of administering to the human in need thereof:
    a) a *cannabis* extract which consists essentially of at least 6.8% of cannabigerolic acid, wherein the *cannabis* extract lacks cannabidiol, cannabidolic acid, tetrahydrocannabinol, tetrahydrocannabinolic acid, cannabidivarin, cannabidivarin acid, tetrahydrocannabivarin, and tetrahydrocannabivarin acid;
    b) resveratrol;
    c) an *echinacea* N-alkylamide; and
    d) eugenol.

18. The method according to claim 17, further consisting essentially of administering at least one of curcumin and quercetin.

* * * * *